US008765955B2

(12) United States Patent
Deng et al.

(10) Patent No.: US 8,765,955 B2
(45) Date of Patent: Jul. 1, 2014

(54) ASYMMETRIC ALDOL ADDITIONS USING BIFUNCTIONAL CINCHONA-ALKALOID-BASED CATALYSTS

(75) Inventors: Li Deng, Newton, MA (US); Hongming Li, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 11/442,667

(22) Filed: May 26, 2006

(65) Prior Publication Data
US 2007/0112199 A1 May 17, 2007

Related U.S. Application Data

(63) Continuation-in-part of application No. 11/140,574, filed on May 27, 2005.

(60) Provisional application No. 60/576,754, filed on Jun. 3, 2004, provisional application No. 60/592,500, filed on Jul. 30, 2004, provisional application No. 60/741,639, filed on Dec. 1, 2005, provisional application No. 60/742,102, filed on Dec. 2, 2005.

(51) Int. Cl.
C07D 453/04 (2006.01)
(52) U.S. Cl.
USPC .......................................................... 546/134
(58) Field of Classification Search
USPC .......................................................... 546/134
See application file for complete search history.

(56) References Cited

U.S. PATENT DOCUMENTS

| 1,720,462 | A | * | 7/1929 | Blagden | 546/134 |
| 2,072,004 | A | * | 2/1937 | Lutz | 510/262 |
| 2,377,814 | A | * | 6/1945 | Schnider | 562/526 |
| 2005/0043353 | A1 | | 2/2005 | Deng et al. | |

FOREIGN PATENT DOCUMENTS

| JP | 2002-080444 A | 3/2002 |
| WO | WO-91/16322 A2 | 10/1991 |
| WO | WO-02-05953 A2 | 1/2002 |
| WO | WO-03/011799 A1 | 2/2003 |
| WO | WO-03/018549 A2 | 3/2003 |
| WO | WO-2005/121137 | 12/2005 |

OTHER PUBLICATIONS

Czerwenka, et. al. "Direct High-Performance Liquid Chromatographic Separation of Peptide Enantiomers: Study on Chiral Recognition by Systematic Evaluation of the Influence of Structural Features of the Chiral Selectors on Enantioselectivity" Analytical Chemistry 2002, 74, 5658-5666.*
Deady, L. W. "A cinchonidine derivative for photoaffinity labelling of proteins" Journal of Labelled Compounds and Radiopharmaceuticals 2000, 43, 977-981.*
Cowman et. al. "Synthesis and Activity of Some Antimalarial Bisquinolinemethanols" Australian Journal of Chemistry 1997, 50, 1091-1096.*
Dorwald F. A. Side Reactions in Organic Synthesis, 2005, Wiley: VCH, Weinheim p. IX of Preface.*
Dorwald F. A. Side Reactions in Organic Synthesis, 2005, Wiley: VCH, Weinheim p. IX of Preface p. 1-15.*
Li, H. et al., "Enantioselective Nitroaldol Reaction of α-Ketoesters Catalyzed by Cinchona Alkaloids", J. Am. Chem. Soc., 128:732-733 (2006).
Misumi, Y, et al., "High Pressure Mediated Asymmetric Henry Reaction of Nitromethane with Carbonyl Compounds Catalyzed by Cinchona Alkaloids", *Heterocycles*, 56:599-605 (2002).
Song, J. et al., "The Mannich Reaction of Malonates with Simple Imines Catalyzed by Bifunctional Cinchona Alkaloids: Enantioselective Synthesis of β-Amino Acids," *J. Am. Chem. Soc.*, 128:6048-6049 (2006).
Wang, Y. et al., "Dual-Function Cinchona Alkaloid Catalysis: Catalytic Asymmetric Tandem Conjugate Addition—Protonation for the Direct Creation of Nonadjacent Stereocenters", *J. Am. Chem. Soc.*, 128:3928-3930 (2006).
Blaser, H.U. et al., "Heterogeneous Enantioselective Hydropgenation of Ethyl Pyruvate Catalyzed by Cinchona-Meodified Pt Catalysts: Effect of Modifier Structure," J. Am. Chem. Soc. 122:12675-12682 (2000).
Brunner, H. et al., "Enantioselective Catalysis. Part 133: Conformational Analysis of Amides of 9-amino(9-deoxy)epicinchonine," Tetrahedron: Asymmetry 11:1501-1512 (2000).
Brunner, H. et al., "Enantioselective Catalysis 98. Preparation of 9-Amino(9-deoxy)cinchona Alkaloids," Tetrahedron: Asymmetry 6(7):1699-1702 (1995).
Lohray, B.B. et al., "A Mechanistically Designed Cinchona Alkaloid Ligand in the Osmium Catalyzed Asymmetric Dihydroxylation of Alkenes," Indian Journal of Chemistry, 416:1226-1233 (2002).
Barnes, D. M. et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram", J. Am. Chem. Soc., 124:13097-13105 (2002).
Berner, O. M. et al., "Asymmetric Michael Additions to Nitroalkenes", Eur. J. Org. Chem., 1877-1894 (2002).
Brunner, H. et al., "α-Amino Acid Derivatives by Enantioselective Decarboxylation", XP-002399850 Eur. J. Org. Cehm. 2854-2862 (2003).
Brunner, H. et al., "Asymmetric Catalysis, CIII[1]: Enantioselective Michael Addition of 1,3-Dicarbonyl Compounds to Conjugated Nitroalkenes", Monatshefte für Chemie, 127:1063-1072 (1996).
Brunner, H. et al., "Asymmetric Catalysis, 131 Naproxen Derivatives by Enantioselective Decarboxylation", XP-002399851 Eur. J. Org. Chem. 2119-2133 (2000).

(Continued)

Primary Examiner — David K O Dell
(74) Attorney, Agent, or Firm — Dana M. Gordon; Foley Hoag LLP

(57) ABSTRACT

One aspect of the present invention relates to asymmetric catalytic nitroaldol (Henry) reactions with ketones as the electrophilic component. In one embodiment, the present invention relates to asymmetric nitroaldol reactions with α-keto esters catalyzed by a new C6'-OH cinchona alkaloid catalyst. In certain embodiments, this reaction is operationally simple and affords high enantioselectivity as well as good to excellent yield for an exceptionally broad range of α-keto esters.

16 Claims, 11 Drawing Sheets

(56) References Cited

OTHER PUBLICATIONS

Calter, M. A., "Catalytic, Asymmetric Dimerization of Methylketene", J. Org. Chem., 61:8006-8007 (1996).
Li, B.-J. et al., "Asymmetic Michael Addition of Arylthiols to α,β-Unsaturated Carbonyl Compounds Catalyzed by Bifunctional Organocatalysts", XP-002399853 Synlett 4: 0603-0606 (2005).
Chen, Y, et al., "Asymmetric Alcoholysis of Cyclic Anhydrides", Chem. Rev., 103:2965-2983 (2003).
Cortez, G. S. et al., "Bicyclic β-Lactones via Intramolecular NCAL Reactions with Cinchona Alkaloids: Effect of the C9-Substituent on Enantioselectivity and Catalyst Conformation", Synthesis, 11:1731-1736 (2001).
Cortez, G. S. et al., "Intramolecular, Nucleophile-Catalyzed Aldol-Lactonization (NCAL) Reactions: Catalytic, Asymmetric Synthesis of Bicyclic β-Lactones", J. Am. Chem. Soc., 123:7945-7946 (2001).
France, S. et al., "Nucleophilic Chiral Amines as Catalysts in Asymmetric Synthesis", Chem. Rev., 103:2985-3012 (2003).
Gröger, H., "The Development of New Monometallic Bifunctional Catalysts with Lewis acid and Lewis Base Properties, and their Application in Asymmetric Cyanation Reactions", Chem. Eur. J., 7(24):5247-5251 (2001).
Hiemstra, H. et al., "Addition of Aromatic Thiols to Conjugated Cycloalkenones, Catalyzed by Chiral β-Hydroxy Amines. A Mechanistic Study on Homogeneous Catalytic Asymmetric Synthesis", J. Am. Chem. Soc., 103:417-430 (1981).
Iwabuchi, Y. et al., "Chiral Amine-Catalyzed Asymmetric Baylis-Hillman Reaction: A Reliable Route to Highly Enantiomerically Enriched (a-Methylene-β-hydroxy)esters", J. Am. Chem. Soc., 121:10219-10220 (1999).
Ji, J. et al., "Catalytic Enantioselective Conjugate Addition of 1,3-Dicarbonyl Compounds to Nitroalkenes", J. Am. Chem. Soc., 121:10215-10216 (1999).
Kawahara, S. et al., "β-Isocupreidine-Catalyzed Asymmetric Baylis-Hillman Reaction of Imines", Organic Letters, 5(17):3103-3105 (2003).
Li, H. et al., "Organocatalytic enantioselective Michael addition of thioacetic acid to enones", XP-002399859 Tetrahedron Letters 47: 3145-3148 (2006).
Li, H. et al., "Stereocontrolled Creation of Adjacent Quaternary and Tertiary Stereocenters by a Catalytic Conjugate Addition", XP-002344994, Angew Chem. Int. Ed. 44: 105-108 (2005).
Li, H. et al., "Catalytic Enantioselective C-C Bond Forming Conjugate Additional with Vinyl Sulfones", J. Am. Chem. Soc., 127:8948-8949 (2005).
Li, H. et al., "Highly Enantioselective Conjugate Addition of Malonate and β-Ketoester to Nitroalkenes: Asymmetric C-C Bond Formation with New Bifunctional Organic Catalysts Based on Cinchona Alkaloids", J. Am. Chem. Soc., 126:9906-9907 (2004).
List, B., "Asymmetric Aminocatalysis", Synlett, 11:1675-1686 (2001).
List, B., "Proline-catalyzed asymmetric reactions", Tetrahedron, 58:5573-5590 (2002).
Liu, T.Y. et al., "Enantioselective construction of Quaternary carbon centre catalysed by bifunctional organocatalyst", XP-002399858 Org. Biomol. Chem. 4: 2097-2099 (2006).
Liu, X. et al., "Highly Enantioselective Amination of a-Substituted a-Cyanoacetates with Chiral Catalysts Accessible from Both Quinine and Quinidine", Organic Letters, 7(2):167-169 (2005).
Ma, D. et al., "Diastereoselective Henry reactions of N,N-dibenzyl χ-amino aldehydes with nitromethane catalyzed by enantiopure guanidines", XP-002399848 Tetrahedron Letters 43:9401-9403 (2002).
Marcelli, T. et al., "Cinchona Derivatives as Bifunctional Organocatalysts for the Direct Asymmetric Nitroaldol (Henry) Reaction", Synlett., 18:2817-2819 (2005).
McCooey, S. et al., "Urea- and Thiourea-Substituted Chinchona Alkaloid Derivatives as Highly Efficient Bifunctional Organocatalysts for the Asymmetric Addtion of Malonate to Nitroalkenes: Inversion of Configuration at C9 Dramatically Improves Catalyst Performance" XP-002399854 Angew Chem. Int. Ed. 44: 6367-6370 (2005).
Okino, T. et al., "Enantioselective Michael Reaction of Malonates to Nitroolefins Catalyzed by Bifunctional Organocatalysts", J. Am. Chem. Soc., 125:12672-12673 (2003).
Rogers, L. M. A. et al., "Enantioselective decarboxylation-reprotonation of an a-amino malonate derivative as a route to optically enriched cyclic λ-amino acid", Tetrahedron Letters, 44:3047-3050 (2003).
Rogers, L. M.-A. et al., "Enantioselective decarboxylation-reprotonation of an a-amino malonate derivative as a route to optically enriched cyclic a-amino acid", Tetrahedron Letters, 44:3047-3050 (2003).
Shibasaki, M. et al., "Asymmetric Catalysis with Heterobimetallic Compounds", Angew. Chem. Int. Ed. Engl., 36:1236-1256 (1997).
Shibasaki, M. et al., "Lanthanide Complexes in Multifunctional Asymmetric Catalysis", Chem. Rev., 102:2187-2209 (2002).
Sibi, M. P. et al., "Enantioselective Conjugate Additions", Tetrahedron, 56:8033-8061 (2000).
Song, J. et al., The Mannich Reaction of Malonates with Simple Imines Catalyzed by Bifunctional Cinchona Alkaloids: Enantioselective Synthesis of β-Amino Acids, XP-002399857 J. Am. Chem. Soc. 128: 6048-6049 (2006).
Suzko, J. et al., "B-Isoquinine and niquine", *Roczniki Chemii*, 5:358-385 (1925).
Taggi, A. E. et al., "Catalytic, Asymmetric Synthesis of β-Lactams", J. Am. Chem. Soc., 122:7831-7832 (2000).
Tian, S-K, et al., "Asymmetric Organic Catalysis with Modified Cinchona Alkaloids", Acc. Chem. Res. (abstract), Dec. 10, 2003.
Tillman, A. L. et al., "Direct enantio- and diastereoselective Mannich reactions of malonate and β-keto esters with N-Boc and N-Cbz aldimines catalysed by a bifunctional cinchonine derivative", XP-002399856 Chem. Commun. 1191-1193 (2006).
Vakulya, B. et al., "Highly Enantioselective Conjugate Addition of Nitromethane to Chalcones Using Bifunctional Cinchona Organocatalysts", XP002399852 Organic Letters 7(10): 1967-1969 (2005).
Wack, H. et al., "Catalytic, Asymmetric a-Halogenation", J. Am. Chem. Soc., 123:1531-1532 (2001).
Wynberg, H., Asymmetric Catalysis by Alkaloids, Department of Chemistry, University of Groningen, The Netherlands, 88-127, 2009.
Wynberg, H., "Asymmetric Catalysts by Alkaloids", Top. Stereochem., 16:87-129 (1986).
Ye, J. et al., Enantioselective Organocatalytic Michael addition of malonate esters to nitro olefins using bifunctional cinchonine derivatives XP-002399855 Chem. Commun. 4481-4483 (2005).

* cited by examiner

| Entry | Catalyst | Conversion (%) | 3a / 3a' | ee (%) |
|---|---|---|---|---|
| 1 | Et$_3$N | > 95 | 80 / 20 | -- |
| 2 | QD | 91 | > 95 / 5 | - 17 |
| 3 | DHQD-PHN | 74 | > 95 / 5 | 59 |
| 4 | (DHQD)$_2$AQN | > 95 | > 95 / 5 | 40 |
| 5 | β-ICD | > 95 | > 95 / 5 | 61 |
| 6 | QD-1a | > 95 | > 95 / 5 | 86 |
| 7 | QD-1b | 93 | > 95 / 5 | 70 |
| 8 | QD-1c | 93 | > 95 / 5 | 93 |
| 9 | QD-1d | > 95 | > 95 / 5 | 97 |
| 10 | Q-1d | > 9 | > 95 / 5 | - 97 |

| Entry | Substrate | R | Time (h) | Isolated Yield (%) | ee (%) by HPLC |
|---|---|---|---|---|---|
| 1 | 2a | ⁓⧹ | 14 (15) | 92 (92) | 96 (97) |
| 2 | 2b | BnO⁓⧹ | 24 (24) | 98 (99) | 94 (95) |
| 3 | 2c | Ph- | 35 (46) | 96 (96) | 95* (96) |
| 4 | 2d | 4-MeO-Ph- | 96 (96) | 86 (84) | 94 (97) |
| 5 | 2e | 4-MeS-Ph- | 72 (72) | 86 (86) | 96 (96) |
| 6 | 2f | 4-Cl-Ph- | 12 (12) | 98 (96) | 97* (96) |
| 7 | 2g | 4-CN-Ph- | 9 (11) | 96 (98) | 94 (97) |
| 8 | 2h | 3-Cl-Ph- | 11 (11) | 91 (96) | 95 (95) |
| 9 | 2i | 2-Naphthyl- | 60 (60) | 96 (97) | 94 (94) |
| 10 | 2j | Me- | 12 (12) | 89 (90) | 95 (95) |
| 11 | 2k | n-Pr- | 17 | 90 | 95 |
| 12 | 2l | Ph⁓ | 14 (11) | 88 (89) | 95 (94) |
| 13 | 2m | EtO$_2$C⁓ | 15 (11) | 87 (86) | 94 (93) |

[A]

[B]

dr: 9/1 ee: 58%ee (major)

*Dynamic resolution* dr: 9/1 ee: 70%ee (major)

Q-1    QD-1    2    3

1a Ar = 4-*t*-Bu-Ph-;  1b Ar = 2-*i*-Pr-Ph-;
1c Ar = Ph-;  1d Ar = 3,5-*bis*CF$_3$Ph- 2,3: Ar = 3,5-*bis*CF$_3$Ph-

ASYMMETRIC ALDOL ADDITIONS USING BIFUNCTIONAL CINCHONA-ALKALOID-BASED CATALYSTS

RELATED APPLICATIONS

This application is a continuation-in-part of U.S. patent application Ser. No. 11/140,574, filed on May 27, 2005; which claims priority to U.S. provisional patent application Ser. No. 60/576,754, filed on Jun. 3, 2004, and U.S. provisional patent application Ser. No. 60/592,500, filed on Jul. 30, 2004; all of which are expressly incorporated by reference. In addition, this application claims priority to U.S. provisional patent application Ser. No. 60/741,639, filed on Dec. 1, 2005; and U.S. provisional patent application Ser. No. 60/742,102, filed on Dec. 2, 2005; both of which are expressly incorporated by reference.

GOVERNMENT SUPPORT

The invention was made with support provided by the National Institutes of Health (GM-61591); therefore, the government has certain rights in the invention.

BACKGROUND OF THE INVENTION

The demand for enantiomerically pure compounds has grown rapidly in recent years. One important use for such chiral, non-racemic alcohols is as intermediates for synthesis in the pharmaceutical industry. For instance, it has become increasingly clear that enantiomerically pure drugs have many advantages over racemic drug mixtures. These advantages include fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming.

Catalytic asymmetric synthesis is providing chemists with new and powerful tools for the efficient synthesis of complex molecules. While many of the catalytic systems are metal-based and rely on chiral Lewis acid and organometallic redox-based catalysis, increasing numbers of asymmetric reactions are catalyzed by chiral nucleophiles, building on the vast assortment of situations in nature in which nucleophiles play pivotal roles. For leading references, see: (a) In *Comprehensive Asymmetric Catalysis*; Jacobsen, E. N., Pfaltz, A., Yamamoto, H., Eds.; Springer: Heidelberg, 1999; (b) In *Asymmetric Catalysis in Organic Synthesis*, Noyori, R., Ed.; Wiley: New York, 1994; (c) In *Asymmetric Synthesis*, 2nd ed.; Ojima, I., Ed.; VCH: New York, 2000; (d) Acc. Chem. Res. 2000, 33, 323. (e) Groger, H.; Wilken, J. *Angew. Chem., Int. Ed.* 2001, 40, 529; (f) Pierre, J.-L. *Chem. Soc. Rev.* 2000, 29, 251-257. (g) Roberts, B. P. *Chem Soc. Rev.* 1999, 28, 25. Chiral amines play a central role in this expanding area of asymmetric catalysis. Although chiral amines have been utilized extensively as chiral ligands, they have also shown great promise in catalyzing a broad range of asymmetric transformations, yielding optically enriched products in high selectivity and yield that may not be accessible through alternative asymmetric technology. Seyden-Penne, J. *Chiral Auxiliaries and Ligands in Asymmetric Synthesis*; Wiley & Sons: New York, 1995.

The cinchona alkaloids were the first chiral amines to be used in asymmetric catalysis, most notably in the pioneering work of Pracejus from the 1960s on disubstituted ketene alcoholysis. Cinchona alkaloids also possess a rich and colorful history that is rooted in natural products and pharmaceutical chemistry. Turner, R. B.; Woodward, R. B. In *In the Alkaloids*; Manske, R. H. F.; Holmes, H. L., Eds.; Academic Press: New York, 1953; Vol. 3, p 24; Verpoorte, R.; Schripsema, J.; Van der Leer, T. In *In the Alkaloids. Chemistry and Pharmacology*, Brossi, A., Ed.; Academic Press: New York, 1988; Vol. 34; Michael, J. P. In *The Quinoline Alkaloids, In Rodd's Chemistry of Carbon Compounds*, 2nd ed.; Sainsbury, M., Ed.; Elsevier: Amsterdam, 1998; 2nd suppl., part F and G, vol 4; 432. They are isolated en masse by extracting the bark of the cinchona tree, which is native to tropical regions. Outside of organic chemistry, the cinchona alkaloids have found wide use as food flavorings (for example as the bitter principle of tonic water) and in the treatment of malaria. Fletcher, D. C. *J. Am. Med. Assoc.* 1976, 236, 305; Mturi, N.; Musumba, C. O.; Wamula, B. M.; Ogutu, B. R.; Newton, C. R. J. C. *CNS Drugs* 2003, 17, 153. Additionally, their roles as ligands, chromatographic selectors, and NMR discriminating agents have been examined extensively over the past thirty years. Several reviews have been published on the catalytic chemistry of cinchona alkaloids over the past four decades. Pracejus, H. *Forschr. Chem. Forsch.* 1967, 8, 493; Morrison, J. D.; Mosher, H. S. *Asymmetric Organic Reactions*; Prentice Hall: Englewood Cliffs, 1971; Wynberg, H. *Top. Stereochem.* 1986, 16, 87; Kacprzak, K.; Gawronski, J. Synthesis 2001, 7, 961.

These reactions appear to be broadly applicable to both research and industrial scale asymmetric synthesis of a wide variety of important chiral building blocks, such as hemi-esters, α-amino acids and α-hydroxy acids. Commercially available modified dimeric cinchona alkaloids $(DHQD)_2$AQN and $(DHQ)_2$AQN, have been identified recently by Deng and coworkers as enantioselective, recyclable catalysts for enantioselective alcoholyses of cyclic anhydrides. However, commercially available $(DHQD)_2$AQN is expensive. For example, the commercial price (Aldrich Chemical Company) for a mole of $(DHQD)_2$AQN is more than $100,000.00. Furthermore, the dimeric catalyst is not available in large quantity (e.g., in kilogram quantity). Therefore, stereoselective reactions using dimeric catalysts are not practical on a relatively large scale (>0.1 mol). Consequently, the development of a new generation of monomeric catalysts that is comparably effective to $(DHQD)_2$AQN, but substantially less costly to produce, is of significant practical value.

Chiral metal and organic catalysts that possess both an acidic and a basic/nucleophilic structural moiety constitute an increasingly powerful platform for the development of asymmetric catalysis. The design and development of such bifunctional chiral catalysts that are efficient yet easily accessible continues to be a major challenge. Wynberg and coworkers demonstrated that natural cinchona alkaloids, via their C9-OH and amine groups, served as bifunctional chiral organic catalysts for enantioselective reactions by activating the nucleophile and electrophile, respectively. Wynberg, H., Hiemstra, H., *J. Am. Chem. Soc.*, 1981, 103, 417. However, the enantioselectivity of various reactions catalyzed by natural cinchona alkaloids as chiral organic catalysts was usually modest. Hatakeyama and coworkers recently reported a rigid modified cinchona alkaloid that is readily accessible from quinidine. Hatakeyama, S. et al., *J. Am. Chem. Soc.,* 1999, 121, 10219; Hatakeyama, S., *Organic Lett.,* 2003, 5, 3103. The catalyst was found to be efficient for an enantioselective Morita-Baylis-Hillman (MBH) reaction. Both the C6'-OH and the amine groups are believed to be involved in the stabilization of the transition state of the enantioselective MBH reaction.

The nitroaldol reaction, or Henry reaction, constitutes an important class of C—C bond forming reactions that provides straightforward access to important synthetic intermediates from readily accessible nitroalkanes and carbonyl compounds. For reviews, see: Luzio, F. A. *Tetrahedron* 2001, 57, 915-945; Ono, N. *The Nitro Group in Organic Synthesis*; Wiley-VCH: New York, 2001; and Seebach, D.; Beck, A. K.; Mukhopadhyay, T.; Thomas, E. *Helv. Chim. Acta* 1982, 65, 1101-1133. Due to its significance in organic synthesis, considerable efforts have been devoted to the development of efficient catalytic asymmetric nitroaldol reactions. For a recent review of catalytic asymmetric nitroaldol reactions, see: Palomo, C.; Oiarbide, M.; Mielgo. A.; *Angew. Chem. Int. Ed.* 2004, 43, 5442-5444. As mentioned above, the nitro group, often described as a "synthetic chameleon," can serve as masked functionality to be further transformed after the addition has taken place. G. Calderari, D. Seebach, Helv. *Chim. Acta* 1995, 68, 1592-1604. The Nef reaction, the nucleophilic displacement, the reduction to amino group, the Myer reaction, and the conversion into a nitrile oxide are only a few examples of the transformations that nitro groups can undergo. H. W. Pinnick, Org. React. 1990, 38,655-792; J. U. Nef, Justus Liebigs Ann. Chem. 1894, 280, 263-291; R. Tamura, A. Kamimura, N. Ono, *Synthesis* 1991, 423-434; R. C. Larock, *Comprehensive Organic Transformations*, VCH, New York, 1989, pp. 411-415; A. K. Beck, D. Seebach, *Chem. Ber.* 1991, 124, 2897-2911; R. E. Maeri, J. Heinzer, D. Seebach, *Liebigs Ann.* 1995, 1193-1215; M. A. Poupart, G. Fazal, S. Goulet, L. T Mar, *J. Org. Chem.* 1999, 64, 1356-1361; A. G. M. Barrett, C. D. Spilling, *Tetrahedron Lett.* 1988, 29, 5733-5734; D. H. Loyd, D. E. Nichols, *J. Org. Chem.* 1986, 51, 4294-4298; V. Meyer, C. Wurster, *Ber. Dtsch. Chem. Ges.* 1873, 6, 1168-1172; M. J. Kamlet, L. A. Kaplan, J. C. Dacons, *J. Org. Chem.* 1961, 26, 4371-4375; T. Mukayama, T Hoshino, *J. Am. Chem. Soc.* 1960, 82, 5339-5342. A number of catalytic synthetic methods have been developed in recent years, making use of nitroalkenes even more attractive. A. G. M. Barret, G. G. Graboski, *Chem. Rev.* 1986, 86, 751-762; R. Ballini, R. Castagnani, M. Petrini, *J. Org. Chem.* 1992, 57, 2160-2162; G. Rosini, R. Ballini, M. Petrini, P Sorrenti, *Synthesis* 1985, 515-517. Consequently, several chiral metal complexes and a phase-transfer catalyst have been identified to be highly efficient catalysts for enantioselective nitroaldol reactions with aldehydes. Sasai, H.; Suzuki, T.; Arai, S.; Shibasaki, M. *J. Am. Chem. Soc.* 1992, 114, 4418-4420; Shibasaki, M.; Yoshikawa, *N. Chem. Rev.* 2002, 102, 2187-2209; Trost, B.; Yeh, V. S. C. *Angew. Chem., Int. Ed.* 2002, 41, 861-863; Trost, B.; Yeh, V. S. C.; Ito, H.; Bremeyer, *N. Org. Lett.* 2002, 4, 2621-2623; Evans, D. A.; Seidel, D.; Rueping, M.; Lam, H. W.; Shaw, J. T.; Downey, C. W. *J. Am. Chem. Soc.* 2003, 125, 12692-12693; Palomo, C.; Oiarbide, M.; Laso, A.; *Angew. Chem. Int. Ed.* 2005, 44, 3881-3884; and Ooi, T.; Doda, K.; Maruoka, K. *J. Am. Chem. Soc.* 2003, 125, 2054-2055.

In contrast to the substantial progress made with aldehydes, efforts to develop enantioselective nitroaldol reactions with ketones have met with limited success. Christensen, C.; Juhl, K.; Jørgensen, K. A.; *Chem. Commun.* 2001, 2222-2223; Christensen, C.; Juhl, K.; Hazell, R. G.; Jørgensen, K. A. *J. Org. Chem.* 2002, 67, 4875-4881; Misumi, Y.; Bulman, R. A.; Matsumoto, K. *Heterocycles* 2002, 56, 599-606; Lu, S. F.; Du, D. M.; Zhang, S. W.; Xu, J. X. *Tetrahedron: Asymmetry* 2004, 15, 119-126; and Du. D. M.; Lu, S. F.; Fang, T.; Xu, J. X. *J. Org. Chem.* 2005, 70, 3712-3715. To date, only one catalyst system, consisting of a Cu-bisoxazoline complex and triethyl amine, has been identified to afford synthetically useful enantioselectivity for the addition of nitromethane to α-keto ethyl esters. However, in addition to requiring a catalyst loading of 20 mol % and the use of anhydrous conditions, both the yield and enantioselectivity of the reaction display a dependence on the structure of the α-keto ethyl esters. For example, the enantioselectivity was high for reactions with aryl α-keto ethyl esters bearing an electron-withdrawing group on the aromatic ring, it became moderate when the electron-withdrawing group was replaced with an electron-donating substituent. Depending on the steric bulk of the alkyl α-keto ethyl esters, the enantioselectivity could be either high or modest. For α-keto ethyl esters bearing an alkenyl group, synthetically useful enantioselectivity was not attainable.

Therefore, it is especially desirable to realize a catalytic asymmetric nitroaldol reaction that affords high enantioselectivity for a wide range of α-keto esters. Such a reaction, in combination with the synthetic versatility of the ester and the nitro groups, would provide enantioselective access to a broad range of optically active tertiary carbinols. Remarkably, in one aspect of the invention, bifunctional organic catalysts derived from either quinidine or quinine have been developed and utilized for catalytic asymmetric nitroaldol reactions.

SUMMARY OF THE INVENTION

One aspect of the present invention relates to asymmetric catalytic nitroaldol (Henry) reactions with ketones as the electrophilic component. In one embodiment, the present invention relates to asymmetric nitroaldol reactions with α-keto esters catalyzed by a new C6'-OH cinchona alkaloid catalyst. In certain embodiments, this reaction is operationally simple and affords high enantioselectivity as well as good to excellent yield for an exceptionally broad range of α-keto esters.

One aspect of the present invention relates generally to quinine- and quinidine-based catalysts. In certain embodiments, the quinine- and quinidine-based catalysts contain a hydrogen bond donating group at the 6' position. In certain embodiments, the quinine- and quinidine-based catalysts contain a hydroxy group at the 6' position. In certain embodiments, the quinine- and quinidine-based catalysts contain an —OC(=O)-aryl group or a —OC(=O)-heteroaryl at the C9 position. In preferred embodiments, the quinine- and quinidine-based catalysts contain an —OC(=O)Ph at the C9 position.

Another aspect of the invention relates to a method of preparing a derivatized quinine- or quinidine-based catalyst comprising 1) reacting quinine or quinidine with base and a compound that has a suitable leaving group, and 2) converting the ring methoxy group to a hydroxy group. In certain embodiments, the leaving group is Cl, Br, I, $OSO_2CH_3$, or $OSO_2CF_3$. In certain embodiments, the leaving group is Cl or I. In certain embodiments, the base is a trialkyl amine. In certain embodiments, the hydroxyl group of the quinine- or quinidine-based catalyst undergoes reaction with an benzoyl halide.

Another aspect of the present invention relates to a method of preparing a chiral, non-racemic alcohol from a prochiral aldehyde or prochiral ketone, comprising the step of: reacting a prochiral aldehyde or prochiral ketone with a nucleophile in the presence of a catalyst; thereby producing a chiral, non-racemic alcohol; wherein said catalyst is a derivatized quinine or quinidine. In certain embodiments, the nucleophile is a nitroalkane. In certain embodiments the nucleophile is nitromethane.

In certain embodiments, the prochiral aldehyde or prochiral ketone is an electron-deficient prochiral aldehyde or prochiral ketone. In certain embodiments, the prochiral aldehyde or prochiral ketone is an α-keto ester. In certain embodiments, the prochiral aldehyde or prochiral ketone is an α-keto ethyl ester. In certain embodiments, the prochiral aldehyde or prochiral ketone is an alkenyl α-keto ethyl ester. In certain embodiments, the catalyst is present in less than about 70 mol % relative to said prochiral aldehyde or prochiral ketone. In certain embodiments, the catalyst is present in less than about 40 mol % relative to said prochiral aldehyde or prochiral ketone. In certain embodiments, the catalyst is present in less than about 10 mol % relative to said prochiral aldehyde or prochiral ketone. In certain embodiments, the catalyst is present in less than about 5 mol % relative to said prochiral aldehyde or prochiral ketone.

In certain embodiments, the chiral, non-racemic alcohol has an enantiomeric excess or diastereomeric excess greater than about 50%. In certain embodiments, the chiral, non-racemic alcohol has an enantiomeric excess or diastereomeric excess greater than about 70%. In certain embodiments, the chiral, non-racemic alcohol has an enantiomeric excess or diastereomeric excess greater than about 90%. In certain embodiments, the chiral, non-racemic alcohol has an enantiomeric excess or diastereomeric excess greater than about 95%. In certain embodiments, the chiral, non-racemic alcohol has an enantiomeric excess or diastereomeric excess greater than about 97%.

Another aspect of the present invention relates to a method of kinetic resolution, comprising the step of: reacting racemic chiral ketone or aldehyde with a nucleophile in the presence of a derivatized quinine or quinidine. In certain embodiments, the nucleophile is a nitroalkane. In certain embodiments, the nucleophile is nitromethane.

DETAILED DESCRIPTION OF THE INVENTION

Definitions

Figure 1:
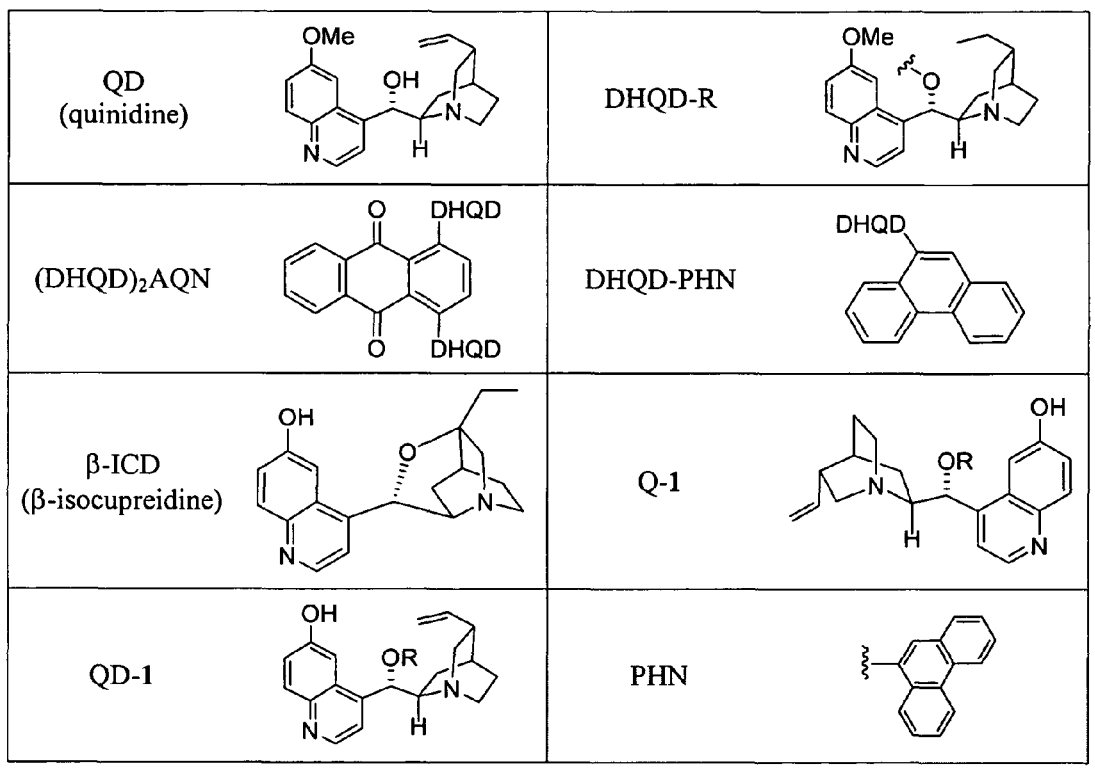
FIG. 1 depicts the structure and nomenclature of several cinchona-alkaloid-based catalysts of the present invention; for Q-1 and QD-1: R=H (a); benzyl (Bn) (b); PHN (c); or benzoyl (Bz) (d).

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g., tosylates), chlorides, bromides, iodides, and the like.

The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "Bronsted base" is art-recognized and refers to an uncharged or charged atom or molecule, e.g., an oxide, amine, alkoxide, or carbonate, that is a proton acceptor.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane or point of symmetry or both.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an ee for a particular enantiomer that is larger than the ee of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A(ee)=$(% Enantiomer $A$)−(% Enantiomer $B$)

where A and B are the enantiomers formed. Additional terms that are used in conjunction with enatioselectivity include "optical purity" or "optical activity". An enantioselective reaction yields a product with an ee greater than zero. Preferred enantioselective reactions yield a product with an ee greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral, non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantiomerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2$—. "Halide" designates the corresponding anion of the halogens, and "pseudohalide" has the definition set forth on page 560 of "Advanced Inorganic Chemistry" by Cotton and Wilkinson.

The terms "amine" and "amino" are art-recognized and refer to both unsubstituted and substituted amines, e.g., a moiety that may be represented by the general formulas:

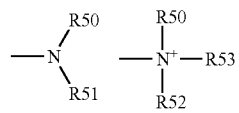

wherein R50, R51, R52 and R53 each independently represent a hydrogen, an alkyl, an alkenyl, —$(CH_2)_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

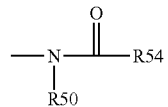

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

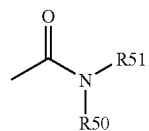

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

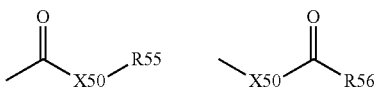

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

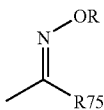

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

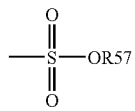

in which R57 is an electron pair, hydrogen, alkyl, cycloalkyl, or aryl.

The term "sulfate" is art recognized and includes a moiety that may be represented by the general formula:

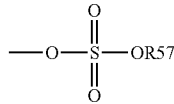

in which R57 is as defined above.

The term "sulfonamido" is art recognized and includes a moiety that may be represented by the general formula:

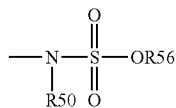

in which R50 and R56 are as defined above.

The term "sulfamoyl" is art-recognized and refers to a moiety that may be represented by the general formula:

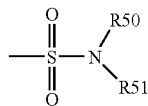

in which R50 and R51 are as defined above.

The term "sulfonyl" is art-recognized and refers to a moiety that may be represented by the general formula:

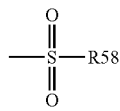

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

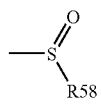

in which R58 is defined above.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "1-adamantyl" is art-recognized and includes a moiety represented by the formula:

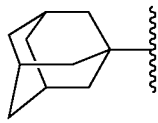

The term "(−)-menthyl" is art-recognized and includes a moiety represented by the formula:

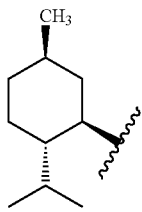 [SMILES: *[C@@H]1C[C@H](C)CC[C@H]1C(C)C]

The term "(+)-menthyl" is art-recognized and includes a moiety represented by the formula:

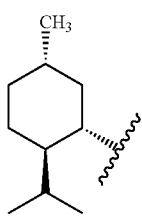 [SMILES: *[C@H]1C[C@@H](C)CC[C@@H]1C(C)C]

The term "isobornyl" is art-recognized and includes a moiety represented by the formula:

The term "isopinocamphyl" is art-recognized and includes a moiety represented by the formula:

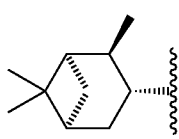 [SMILES: *[C@@H]1C[C@@H]2C[C@H]([C@H]1C)C2(C)C]

The term "(+)-fenchyl" is art-recognized and includes a moiety represented by the formula:

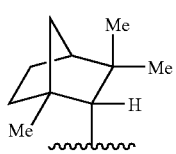 [SMILES: *C1C2(C)CCC(C2)C1(C)C]

The abbreviation "QD" represents a moiety according to the following formula:

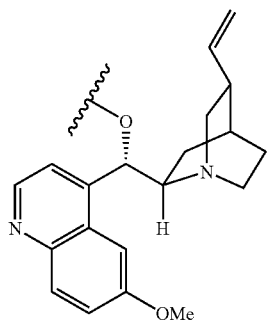 [SMILES: *O[C@@H](c1ccnc2ccc(OC)cc12)C1CC2CCN1CC2C=C]

The term "Q" represents a moiety according to the following formula:

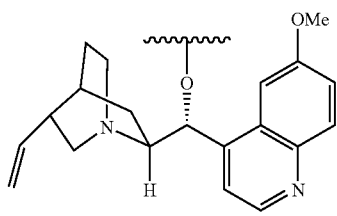 [SMILES: *O[C@H](c1ccnc2ccc(OC)cc12)C1CC2CCN1CC2C=C]

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

Catalysts of the Invention

The catalysts employed in the subject methods are non-racemic chiral amines which present an asymmetric environment, causing stereochemical discrimination between two stereogenic faces of a carbonyl moiety; or two or more prochiral moieties (e.g., related by symmetry in a prochiral or meso molecule (i.e., a molecule comprising at least two chiral centers), both of which comprise an internal plane or point of symmetry or both. In general, catalysts intended by the present invention can be characterized in terms of a number of features. For instance, a salient aspect of each of the catalysts contemplated by the instant invention concerns the use of asymmetric bicyclic or polycyclic scaffolds incorporating the tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states for the overall transformation. Furthermore, the choice of substituents may also effect catalyst reactivity.

As mentioned above, the choice of catalyst substituents can also effect the electronic properties of the catalyst. Substitution of the catalyst with electron-rich (electron-donating) moieties (for example, alkoxy or amino groups) may increase the electron density of the catalyst at the tertiary amine nitrogen, rendering it a stronger nucleophile and/or Bronsted base and/or Lewis base. Conversely, substitution of the catalyst with electron-poor moieties (for example, chloro or trifluoromethyl groups) can result in lower electron density of the catalyst at the tertiary amine nitrogen, rendering it a weaker nucleophile and/or Bronsted base and/or Lewis base. In other words, the electron density of the catalyst can be important because the electron density at the tertiary amine nitrogen will influence the Lewis basicity of the nitrogen and its nucleophilicity. Choice of appropriate substituents thus makes possible the "tuning" of the reaction rate and the stereoselectivity of the reaction.

One aspect of the present invention relates to a compound represented by formula I:

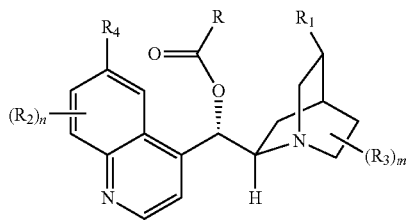

wherein, independently for each occurrence:

R represents a substituted or unsubstituted alkyl, alkenyl, alkynyl, aryl, aralkyl, heteroaryl, heteroaralkyl, heterocyclic, or heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —NH$_2$, —NHR$_2$, —NH(C=O)NR$_2$R$_3$, —NH(SO$_2$)R$_2$, —NH(C=O)OR$_2$, or —NH(C=O)R$_2$.

In certain embodiments, the compounds of the present invention are represented by formula I and any of the attendant definitions, wherein $R_4$ represents —OH.

In certain embodiments, the compounds of the present invention are represented by formula I and any of the attendant definitions, wherein R represents aryl or heteroaryl.

In certain embodiments, the compounds of the present invention are represented by formula I and any of the attendant definitions, wherein R represents aryl.

In certain embodiments, the compounds of the present invention are represented by formula I and any of the attendant definitions, wherein R represents substituted or unsubstituted phenyl.

In certain embodiments, the compounds of the present invention are represented by formula I and any of the attendant definitions, wherein R represents mono-substituted phenyl.

In certain embodiments, the compounds of the present invention are represented by formula I and any of the attendant definitions, wherein R represents unsubstituted phenyl.

In certain embodiments, the compounds of the present invention are represented by formula I and any of the attendant definitions, wherein $R_1$ is alkyl.

In certain embodiments, the compounds of the present invention are represented by formula I and any of the attendant definitions, wherein $R_1$ is ethyl.

In certain embodiments, the compounds of the present invention are represented by formula I and any of the attendant definitions, wherein $R_1$ is alkenyl.

In certain embodiments, the compounds of the present invention are represented by formula I and any of the attendant definitions, wherein $R_1$ is —CH=CH$_2$.

In certain embodiments, the compounds of the present invention are represented by formula I and any of the attendant definitions, wherein n is 0.

In certain embodiments, the compounds of the present invention are represented by formula I and any of the attendant definitions, wherein m is 0.

In certain embodiments, the compounds of the present invention are represented by formula I and any of the attendant definitions, wherein R is aryl and $R_1$ is alkyl.

In certain embodiments, the compounds of the present invention are represented by formula I and any of the attendant definitions, wherein R is substituted or unsubstituted phenyl and $R_1$ is alkyl.

In certain embodiments, the compounds of the present invention are represented by formula I and any of the attendant definitions, wherein R is unsubstituted phenyl and $R_1$ is ethyl.

In certain embodiments, the compounds of the present invention are represented by formula I and any of the attendant definitions, wherein R is aryl and $R_1$ is alkenyl.

In certain embodiments, the compounds of the present invention are represented by formula I and any of the attendant definitions, wherein R is substituted or unsubstituted phenyl and $R_1$ is alkenyl.

In certain embodiments, the compounds of the present invention are represented by formula I and any of the attendant definitions, wherein R is unsubstituted phenyl and $R_1$ is —CH=CH$_2$.

In certain embodiments, the compounds of the present invention are represented by formula I and any of the attendant definitions, wherein R is aryl, $R_1$ is alkyl, m is 0, and n is 0.

In certain embodiments, the compounds of the present invention are represented by formula I and any of the attendant definitions, wherein R is substituted or unsubstituted phenyl, $R_1$ is alkyl, m is 0, and n is 0.

In certain embodiments, the compounds of the present invention are represented by formula I and any of the attendant definitions, wherein R is unsubstituted phenyl, $R_1$ is ethyl, m is 0, and n is 0.

In certain embodiments, the compounds of the present invention are represented by formula I and any of the attendant definitions, wherein R is aryl, $R_1$ is alkenyl, m is 0, and n is 0.

In certain embodiments, the compounds of the present invention are represented by formula I and any of the attendant definitions, wherein R is substituted or unsubstituted phenyl, $R_1$ is alkenyl, m is 0, and n is 0.

In certain embodiments, the compounds of the present invention are represented by formula I and any of the attendant definitions, wherein R is unsubstituted phenyl, $R_1$ is —CH=CH$_2$, m is 0, and n is 0.

Another aspect of the present invention relates to a compound represented by formula II:

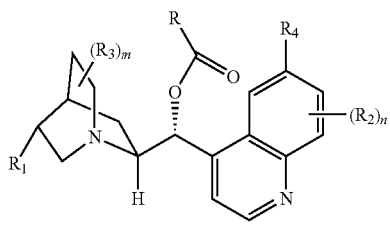

II wherein, independently for each occurrence:

R represents a substituted or unsubstituted alkyl, alkenyl, alkynyl, aryl, aralkyl, heteroaryl, heteroaralkyl, heterocyclic, or heterocycloalkyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —NH$_2$, —NHR$_2$—NH(C=O)NR$_2$R$_3$, —NH(SO$_2$)R$_2$, —NH(C=O)OR$_2$, or —NH(C=O)R$_2$.

In certain embodiments, the compounds of the present invention are represented by formula II and any of the attendant definitions, wherein $R_4$ represents —OH.

In certain embodiments, the compounds of the present invention are represented by formula II and any of the attendant definitions, wherein R represents aryl or heteroaryl.

In certain embodiments, the compounds of the present invention are represented by formula II and any of the attendant definitions, wherein R represents aryl.

In certain embodiments, the compounds of the present invention are represented by formula II and any of the attendant definitions, wherein R represents substituted or unsubstituted phenyl.

In certain embodiments, the compounds of the present invention are represented by formula II and any of the attendant definitions, wherein R represents mono-substituted phenyl.

In certain embodiments, the compounds of the present invention are represented by formula II and any of the attendant definitions, wherein R represents unsubstituted phenyl.

In certain embodiments, the compounds of the present invention are represented by formula II and any of the attendant definitions, wherein $R_1$ is alkyl.

In certain embodiments, the compounds of the present invention are represented by formula II and any of the attendant definitions, wherein $R_1$ is ethyl.

In certain embodiments, the compounds of the present invention are represented by formula II and any of the attendant definitions, wherein $R_1$ is alkenyl.

In certain embodiments, the compounds of the present invention are represented by formula II and any of the attendant definitions, wherein $R_1$ is —CH=CH$_2$.

In certain embodiments, the compounds of the present invention are represented by formula II and any of the attendant definitions, wherein n is 0.

In certain embodiments, the compounds of the present invention are represented by formula II and any of the attendant definitions, wherein m is 0.

In certain embodiments, the compounds of the present invention are represented by formula II and any of the attendant definitions, wherein R is aryl and $R_1$ is alkyl.

In certain embodiments, the compounds of the present invention are represented by formula II and any of the attendant definitions, wherein R is substituted or unsubstituted phenyl and $R_1$ is alkyl.

In certain embodiments, the compounds of the present invention are represented by formula II and any of the attendant definitions, wherein R is unsubstituted phenyl and $R_1$ is ethyl.

In certain embodiments, the compounds of the present invention are represented by formula II and any of the attendant definitions, wherein R is aryl and $R_1$ is alkenyl.

In certain embodiments, the compounds of the present invention are represented by formula II and any of the attendant definitions, wherein R is substituted or unsubstituted phenyl and $R_1$ is alkenyl.

In certain embodiments, the compounds of the present invention are represented by formula II and any of the attendant definitions, wherein R is unsubstituted phenyl and $R_1$ is —CH=CH$_2$.

In certain embodiments, the compounds of the present invention are represented by formula II and any of the attendant definitions, wherein R is aryl, $R_1$ is alkyl, m is 0, and n is 0.

In certain embodiments, the compounds of the present invention are represented by formula II and any of the attendant definitions, wherein R is substituted or unsubstituted phenyl, $R_1$ is alkyl, m is 0, and n is 0.

In certain embodiments, the compounds of the present invention are represented by formula II and any of the attendant definitions, wherein R is unsubstituted phenyl, $R_1$ is ethyl, m is 0, and n is 0.

In certain embodiments, the compounds of the present invention are represented by formula II and any of the attendant definitions, wherein R is aryl, $R_1$ is alkenyl, m is 0, and n is 0.

In certain embodiments, the compounds of the present invention are represented by formula II and any of the attendant definitions, wherein R is substituted or unsubstituted phenyl, $R_1$ is alkenyl, m is 0, and n is 0.

In certain embodiments, the compounds of the present invention are represented by formula II and any of the attendant definitions, wherein R is unsubstituted phenyl, $R_1$ is —CH=CH$_2$, m is 0, and n is 0.

Methods of the Invention—Preparation of Asymmetric Bifunctional Catalysts

One aspect of the invention relates to a method of preparing a bifunctional catalyst as depicted in Scheme 1:

Scheme 1

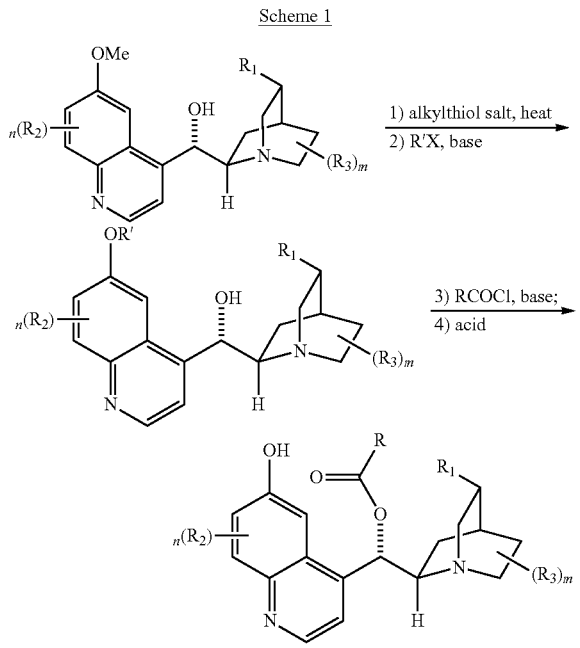

wherein, independently for each occurrence:

X represents Cl, Br, I, OSO$_2$CH$_3$, or OSO$_2$CF$_3$;

R represents a substituted or unsubstituted alkyl, alkenyl, alkynyl, aryl, aralkyl, heteroaryl, heteroaralkyl, heterocyclic, or heterocycloalkyl;

R' represents —Si(R")$_3$, aralkyl or tetrahydropyranyl;

R" represents substituted or unsubstituted alkyl, alkenyl, alkynyl, aryl, aralkyl, heteroaryl, heteroaralkyl, heterocyclic, or heterocycloalkyl;

R$_1$ represents a substituted or unsubstituted alkyl or alkenyl;

R$_2$ and R$_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive;

base is a Bronsted base; and acid is a Bronsted acid.

In certain embodiments, the present invention relates to the aforementioned method and any of the attendant definitions, wherein X is Cl or I.

In certain embodiments, the present invention relates to the aforementioned method and any of the attendant definitions, wherein said base is a trialkyl amine.

In certain embodiments, the present invention relates to the aforementioned method and any of the attendant definitions, wherein said base is triethylamine.

In certain embodiments, the present invention relates to the aforementioned method and any of the attendant definitions, wherein said acid is HF, HCl, HBr, HI, HNO$_3$, or H$_2$SO$_4$.

In certain embodiments, the present invention relates to the aforementioned method and any of the attendant definitions, wherein said acid is HF.

In certain embodiments, the present invention relates to the aforementioned method and any of the attendant definitions, wherein R represents aryl or heteroaryl.

In certain embodiments, the present invention relates to the aforementioned method and any of the attendant definitions, wherein R represents aryl.

In certain embodiments, the present invention relates to the aforementioned method and any of the attendant definitions, wherein R represents substituted or unsubstituted phenyl.

In certain embodiments, the present invention relates to the aforementioned method and any of the attendant definitions, wherein R represents mono-substituted phenyl.

In certain embodiments, the present invention relates to the aforementioned method and any of the attendant definitions, wherein R represents unsubstituted phenyl.

In certain embodiments, the present invention relates to the aforementioned method and any of the attendant definitions, wherein R$_1$ is alkyl.

In certain embodiments, the present invention relates to the aforementioned method and any of the attendant definitions, wherein R$_1$ is ethyl.

In certain embodiments, the present invention relates to the aforementioned method and any of the attendant definitions, wherein R$_1$ is alkenyl.

In certain embodiments, the present invention relates to the aforementioned method and any of the attendant definitions, wherein R$_1$ is —CH═CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R' represents —Si(R")$_3$.

In certain embodiments, the present invention relates to the aforementioned method and any of the attendant definitions, wherein R' represents —Si(R")$_3$; and R" represents alkyl or aryl.

In certain embodiments, the present invention relates to the aforementioned method and any of the attendant definitions, wherein R is aryl and R$_1$ is alkyl.

In certain embodiments, the present invention relates to the aforementioned method and any of the attendant definitions, wherein R is substituted or unsubstituted phenyl and R$_1$ is alkyl.

In certain embodiments, the present invention relates to the aforementioned method and any of the attendant definitions, wherein R is unsubstituted phenyl and R$_1$ is ethyl.

In certain embodiments, the present invention relates to the aforementioned method and any of the attendant definitions, wherein R is aryl and R$_1$ is alkenyl.

In certain embodiments, the present invention relates to the aforementioned method and any of the attendant definitions, wherein R is substituted or unsubstituted phenyl and R$_1$ is alkenyl.

In certain embodiments, the present invention relates to the aforementioned method and any of the attendant definitions, wherein R is unsubstituted phenyl and R$_1$ is —CH═CH$_2$.

In certain embodiments, the present invention relates to the aforementioned method and any of the attendant definitions, wherein R is aryl, R$_1$ is alkyl, m is 0, and n is 0.

In certain embodiments, the present invention relates to the aforementioned method and any of the attendant definitions, wherein R is substituted or unsubstituted phenyl, R$_1$ is alkyl, m is 0, and n is 0.

In certain embodiments, the present invention relates to the aforementioned method and any of the attendant definitions, wherein R is unsubstituted phenyl, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is substituted or unsubstituted phenyl, $R_1$ is alkenyl, m is 0, and n is 0.

In certain embodiments, the present invention relates to the aforementioned method and any of the attendant definitions, wherein R is unsubstituted phenyl, $R_1$ is —CH=$CH_2$, m is 0, and n is 0.

Another aspect of the invention relates to a method of preparing a bifunctional catalyst as depicted in Scheme 2:

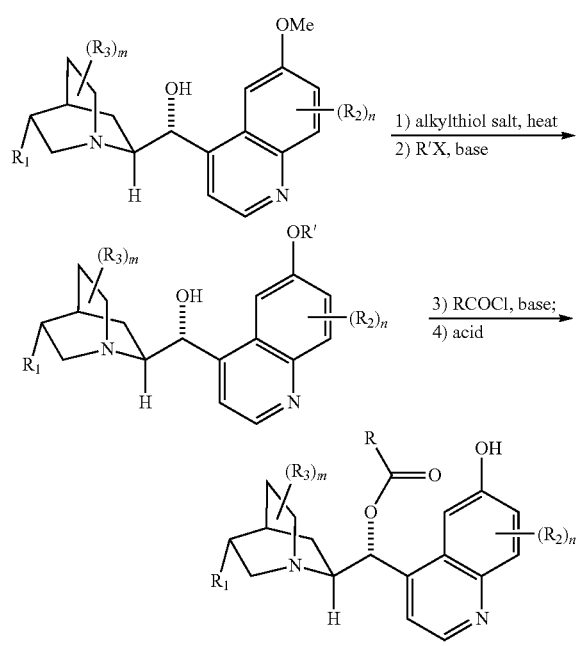

Scheme 2 wherein, independently for each occurrence:

X represents Cl, Br, I, $OSO_2CH_3$, or $OSO_2CF_3$;

R represents a substituted or unsubstituted alkyl, alkenyl, alkynyl, aryl, aralkyl, heteroaryl, heteroaralkyl, heterocyclic, or heterocycloalkyl;

R' represents —Si(R")$_3$, aralkyl or tetrahydropyranyl;

R" represents substituted or unsubstituted alkyl, alkenyl, alkynyl, aryl, aralkyl, heteroaryl, heteroaralkyl, heterocyclic, or heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive;

base is a Bronsted base; and acid is a Bronsted acid.

In certain embodiments, the present invention relates to the aforementioned method and any of the attendant definitions, wherein X is Cl or I.

In certain embodiments, the present invention relates to the aforementioned method and any of the attendant definitions, wherein said base is a trialkyl amine.

In certain embodiments, the present invention relates to the aforementioned method and any of the attendant definitions, wherein said base is triethylamine.

In certain embodiments, the present invention relates to the aforementioned method and any of the attendant definitions, wherein said acid is HF, HCl, HBr, HI, $HNO_3$, or $H_2SO_4$.

In certain embodiments, the present invention relates to the aforementioned method and any of the attendant definitions, wherein said acid is HF.

In certain embodiments, the present invention relates to the aforementioned method and any of the attendant definitions, wherein R represents aryl or heteroaryl.

In certain embodiments, the present invention relates to the aforementioned method and any of the attendant definitions, wherein R represents aryl.

In certain embodiments, the present invention relates to the aforementioned method and any of the attendant definitions, wherein R represents substituted or unsubstituted phenyl.

In certain embodiments, the present invention relates to the aforementioned method and any of the attendant definitions, wherein R represents mono-substituted phenyl.

In certain embodiments, the present invention relates to the aforementioned method and any of the attendant definitions, wherein R represents unsubstituted phenyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R' represents —Si(R")$_3$.

In certain embodiments, the present invention relates to the aforementioned method and any of the attendant definitions, wherein R' represents —Si(R")$_3$; and R" represents alkyl or aryl.

In certain embodiments, the present invention relates to the aforementioned method and any of the attendant definitions, wherein R' represents —Si(R")$_3$; and R" is i-Pr.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is substituted or unsubstituted phenyl and $R_1$ is alkyl.

In certain embodiments, the present invention relates to the aforementioned method and any of the attendant definitions, wherein R is unsubstituted phenyl and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is substituted or unsubstituted phenyl and $R_1$ is alkenyl.

In certain embodiments, the present invention relates to the aforementioned method and any of the attendant definitions, wherein R is unsubstituted phenyl and $R_1$ is —CH=$CH_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is substituted or unsubstituted phenyl, $R_1$ is alkyl, m is 0, and n is 0.

In certain embodiments, the present invention relates to the aforementioned method and any of the attendant definitions, wherein R is unsubstituted phenyl, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is substituted or unsubstituted phenyl, $R_1$ is alkenyl, m is 0, and n is 0.

In certain embodiments, the present invention relates to the aforementioned method and any of the attendant definitions, wherein R is unsubstituted phenyl, $R_1$ is —CH=$CH_2$, m is 0, and n is 0.

Methods of the Invention—Catalyzed Reactions

In one aspect of the present invention there is provided a process for stereoselectively producing compounds with at least one stereogenic center from prochiral, or racemic starting materials. An advantage of this invention is that enantiomerically enriched products can be synthesized from prochiral or racemic reactants. Another advantage is that yield losses associated with the production of an undesired enantiomer can be substantially reduced or eliminated altogether.

In general, the invention features a stereoselective nucleophilic addition process which comprises combining a nucleophile, a prochiral or chiral substrate, and at least a catalytic amount of non-racemic chiral catalyst of particular characteristics (as described herein). The substrate of the reaction will include carbonyls susceptible to attack by the nucleophile. The combination is maintained under conditions appropriate for the chiral catalyst to catalyze the nucleophilic addition between the nucleophilic reactant and carbonyl-containing substrate (e.g., an α-keto ester). This reaction can be applied to enantioselective processes as well as diastereoselective processes. It may also be adapted for regioselective reactions. Examples of enantioselective reactions, kinetic resolutions, and regioselective reactions which may be catalyzed according to the present invention follow.

The processes of this invention can provide optically active products with very high stereoselectivity (e.g., enantioselectivity or diastereoselectivity) or regioselectivity. In preferred embodiments of the subject desymmetrization reactions, products with enantiomeric excesses of greater than about 50%, greater than about 70%, greater than about 90%, and most preferably greater than about 95% can be obtained. The processes of this invention can also be carried out under reaction conditions suitable for commercial use, and typically proceed at reaction rates suitable for large scale operations.

As is clear from the above discussion, the chiral products produced by the asymmetric synthesis processes of this invention can undergo further reaction(s) to afford desired derivatives thereof (e.g., Scheme 3). Such permissible derivatization reactions can be carried out in accordance with conventional procedures known in the art. For example, potential nitro-derivatization reactions include the Nef reaction, the nucleophilic displacement, the reduction to amino group, the Myer reaction, the conversion into a nitrile oxide, and the like. The invention expressly contemplates the preparation of end-products and synthetic intermediates which are useful for the preparation or development or both of therapeutic compounds.

Scheme 3. A General Approach to Optically Active Tertiary Carbinols

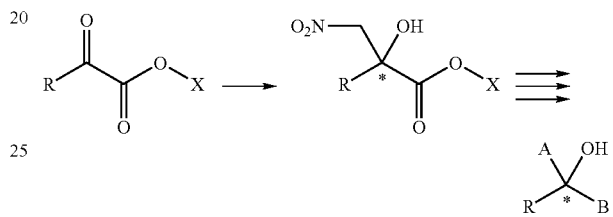

One aspect of the present invention relates to a method of preparing a chiral, non-racemic alcohol from a prochiral aldehyde or prochiral ketone, comprising the step of:

reacting a prochiral aldehyde or prochiral ketone with a nitroalkane in the presence of a catalyst; thereby producing a chiral, non-racemic alcohol; wherein said catalyst is represented by formula I:

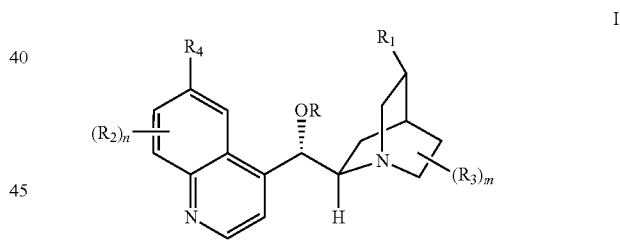

wherein, independently for each occurrence:

R represents substituted or unsubstituted aryl, heteroaryl, aralkyl, heteroaralkyl, arylcarbonyl, or heteroarylcarbonyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH.

In certain embodiments, the present invention relates to the aforementioned method and any of the attendant definitions, wherein R represents phenanthrene.

In certain embodiments, the present invention relates to the aforementioned method and any of the attendant definitions, wherein R represents substituted or unsubstituted diazene.

In certain embodiments, the present invention relates to the aforementioned method and any of the attendant definitions, wherein R represents 5-chloro-3,6-diphenyl-2,4-diazene.

In certain embodiments, the present invention relates to the aforementioned method and any of the attendant definitions, wherein R represents halobenzoyl.

In certain embodiments, the present invention relates to the aforementioned method and any of the attendant definitions, wherein R represents 4-chlorobenzoyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is diazene and $R_1$ is ethyl.

In certain embodiments, the present invention relates to the aforementioned method and any of the attendant definitions, wherein R is halobenzoyl and $R_1$ is ethyl.

In certain embodiments, the present invention relates to the aforementioned method and any of the attendant definitions, wherein R represents 5-chloro-3,6-diphenyl-2,4-diazene; and R1 is ethyl.

In certain embodiments, the present invention relates to the aforementioned method and any of the attendant definitions, wherein R represents 4-chlorobenzoyl; and $R_1$ is ethyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is diazene and $R_1$ is —CH=$CH_2$.

In certain embodiments, the present invention relates to the aforementioned method and any of the attendant definitions, wherein R is halobenzoyl and $R_1$ is —CH=$CH_2$.

In certain embodiments, the present invention relates to the aforementioned method and any of the attendant definitions, wherein R represents 5-chloro-3,6-diphenyl-2,4-diazene; and R1 is —CH=$CH_2$.

In certain embodiments, the present invention relates to the aforementioned method and any of the attendant definitions, wherein R represents 4-chlorobenzoyl; and $R_1$ is —CH=$CH_2$.

In certain embodiments, the present invention relates to the aforementioned method and any of the attendant definitions, wherein R is phenanthrene; $R_1$ is ethyl; m is 0; and n is 0.

In certain embodiments, the present invention relates to the aforementioned method and any of the attendant definitions, wherein R is diazene; $R_1$ is ethyl; m is 0; and n is 0.

In certain embodiments, the present invention relates to the aforementioned method and any of the attendant definitions, wherein R is halobenzoyl; $R_1$ is ethyl; m is 0; and n is 0.

In certain embodiments, the present invention relates to the aforementioned method and any of the attendant definitions, wherein R represents 5-chloro-3,6-diphenyl-2,4-diazene; $R_1$ is ethyl; m is 0; and n is 0.

In certain embodiments, the present invention relates to the aforementioned method and any of the attendant definitions, wherein R represents 4-chlorobenzoyl; $R_1$ is ethyl; m is 0; and n is 0.

In certain embodiments, the present invention relates to the aforementioned method and any of the attendant definitions, wherein R is phenanthrene; $R_1$ is —CH=$CH_2$; m is 0; and n is 0.

In certain embodiments, the present invention relates to the aforementioned method and any of the attendant definitions, wherein R is diazene; $R_1$ is —CH=$CH_2$; m is 0; and n is 0.

In certain embodiments, the present invention relates to the aforementioned method and any of the attendant definitions, wherein R is halobenzoyl; $R_1$ is —CH=$CH_2$; m is 0; and n is 0.

In certain embodiments, the present invention relates to the aforementioned method and any of the attendant definitions, wherein R represents 5-chloro-3,6-diphenyl-2,4-diazene; $R_1$ is —CH=$CH_2$; m is 0; and n is 0.

In certain embodiments, the present invention relates to the aforementioned method and any of the attendant definitions, wherein R represents 4-chlorobenzoyl; $R_1$ is —CH=$CH_2$; m is 0; and n is 0.

In certain embodiments, the present invention relates to the aforementioned method and any of the attendant definitions, wherein said nitroalkane is nitromethane, nitroethane, nitropropane or nitrobutane.

In certain embodiments, the present invention relates to the aforementioned method and any of the attendant definitions, wherein said nitroalkane is nitromethane or nitroethane.

In certain embodiments, the present invention relates to the aforementioned method and any of the attendant definitions, wherein said nitroalkane is nitromethane.

In certain embodiments, the present invention relates to the aforementioned method and any of the attendant definitions, wherein said prochiral aldehyde or prochiral ketone is represented by A:

$$\underset{X}{\overset{O}{\|}}{Z} \qquad A$$

wherein

X represents alkyl, aryl, heteroaryl, aralkyl, or heteroaralkyl; and

Z represents H, perfluoroalkyl, alkyl, aryl, heteroaryl, aralkyl, or heteroaralkyl.

In certain embodiments, the present invention relates to the aforementioned method and any of the attendant definitions, wherein said prochiral aldehyde or prochiral ketone is represented by A; and Z represents H or trifluoromethyl.

In certain embodiments, the present invention relates to the aforementioned method and any of the attendant definitions, wherein said prochiral aldehyde or prochiral ketone is represented by B:

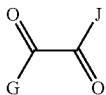

wherein
G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino;

J represents H, perfluoroalkyl, alkyl, aryl, heteroaryl, aralkyl, or heteroaralkyl; and G and J may be connected by a covalent bond to form a 4, 5, 6, 7, or 8-membered ring.

In certain embodiments, the present invention relates to the aforementioned method and any of the attendant definitions, wherein said prochiral aldehyde or prochiral ketone is represented by B; and J represents H.

In certain embodiments, the present invention relates to the aforementioned method and any of the attendant definitions, wherein said prochiral aldehyde or prochiral ketone is represented by B; and B represents cyclobutane-1,2-dione, cyclopentane-1,2-dione, cyclohexane-1,2-dione, cycloheptane-1,2-dione, or cyclooctane-1,2-dione.

In certain embodiments, the present invention relates to the aforementioned method and any of the attendant definitions, wherein said catalyst is present in less than about 70 mol % relative to said prochiral aldehyde or prochiral ketone.

In certain embodiments, the present invention relates to the aforementioned method and any of the attendant definitions, wherein said catalyst is present in less than about 40 mol % relative to said prochiral aldehyde or prochiral ketone.

In certain embodiments, the present invention relates to the aforementioned method and any of the attendant definitions, wherein said catalyst is present in less than about 10 mol % relative to said prochiral aldehyde or prochiral ketone.

In certain embodiments, the present invention relates to the aforementioned method and any of the attendant definitions, wherein said catalyst is present in less than about 5 mol % relative to said prochiral aldehyde or prochiral ketone.

In certain embodiments, the present invention relates to the aforementioned method and any of the attendant definitions, wherein said chiral, non-racemic alcohol has an enantiomeric excess or diastereomeric excess greater than about 50%.

In certain embodiments, the present invention relates to the aforementioned method and any of the attendant definitions, wherein said chiral, non-racemic alcohol has an enantiomeric excess or diastereomeric excess greater than about 70%.

In certain embodiments, the present invention relates to the aforementioned method and any of the attendant definitions, wherein said chiral, non-racemic alcohol has an enantiomeric excess or diastereomeric excess greater than about 90%.

In certain embodiments, the present invention relates to the aforementioned method and any of the attendant definitions, wherein said chiral, non-racemic alcohol has an enantiomeric excess or diastereomeric excess greater than about 95%.

One aspect of the present invention relates to a method of preparing a chiral, non-racemic alcohol from a prochiral aldehyde or prochiral ketone, comprising the step of:

reacting a prochiral aldehyde or prochiral ketone with a nitroalkane in the presence of a catalyst; thereby producing a chiral, non-racemic alcohol; wherein said catalyst is represented by formula II:

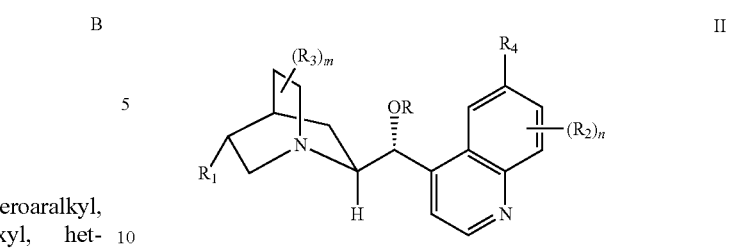

wherein, independently for each occurrence:

R represents substituted or unsubstituted aryl, heteroaryl, aralkyl, heteroaralkyl, arylcarbonyl, or heteroarylcarbonyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH.

In certain embodiments, the present invention relates to the aforementioned method and any of the attendant definitions, wherein R represents phenanthrene.

In certain embodiments, the present invention relates to the aforementioned method and any of the attendant definitions, wherein R represents substituted or unsubstituted diazene.

In certain embodiments, the present invention relates to the aforementioned method and any of the attendant definitions, wherein R represents 5-chloro-3,6-diphenyl-2,4-diazene.

In certain embodiments, the present invention relates to the aforementioned method and any of the attendant definitions, wherein R represents halobenzoyl.

In certain embodiments, the present invention relates to the aforementioned method and any of the attendant definitions, wherein R represents 4-chlorobenzoyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is diazene and $R_1$ is ethyl.

In certain embodiments, the present invention relates to the aforementioned method and any of the attendant definitions, wherein R is halobenzoyl and $R_1$ is ethyl.

In certain embodiments, the present invention relates to the aforementioned method and any of the attendant definitions, wherein R represents 5-chloro-3,6-diphenyl-2,4-diazene; and R1 is ethyl.

In certain embodiments, the present invention relates to the aforementioned method and any of the attendant definitions, wherein R represents 4-chlorobenzoyl; and $R_1$ is ethyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is diazene and $R_1$ is —CH=$CH_2$.

In certain embodiments, the present invention relates to the aforementioned method and any of the attendant definitions, wherein R is halobenzoyl and $R_1$ is —CH=$CH_2$.

In certain embodiments, the present invention relates to the aforementioned method and any of the attendant definitions, wherein R represents 5-chloro-3,6-diphenyl-2,4-diazene; and R1 is —CH=$CH_2$.

In certain embodiments, the present invention relates to the aforementioned method and any of the attendant definitions, wherein R represents 4-chlorobenzoyl; and $R_1$ is —CH=$CH_2$.

In certain embodiments, the present invention relates to the aforementioned method and any of the attendant definitions, wherein R is phenanthrene; $R_1$ is ethyl; m is 0; and n is 0.

In certain embodiments, the present invention relates to the aforementioned method and any of the attendant definitions, wherein R is diazene; $R_1$ is ethyl; m is 0; and n is 0.

In certain embodiments, the present invention relates to the aforementioned method and any of the attendant definitions, wherein R is halobenzoyl; $R_1$ is ethyl; m is 0; and n is 0.

In certain embodiments, the present invention relates to the aforementioned method and any of the attendant definitions, wherein R represents 5-chloro-3,6-diphenyl-2,4-diazene; $R_1$ is ethyl; m is 0; and n is 0.

In certain embodiments, the present invention relates to the aforementioned method and any of the attendant definitions, wherein R represents 4-chlorobenzoyl; $R_1$ is ethyl; m is 0; and n is 0.

In certain embodiments, the present invention relates to the aforementioned method and any of the attendant definitions, wherein R is phenanthrene; $R_1$ is —CH=$CH_2$; m is 0; and n is 0.

In certain embodiments, the present invention relates to the aforementioned method and any of the attendant definitions, wherein R is diazene; $R_1$ is —CH=$CH_2$; m is 0; and n is 0.

In certain embodiments, the present invention relates to the aforementioned method and any of the attendant definitions, wherein R is halobenzoyl; $R_1$ is —CH=$CH_2$; m is 0; and n is 0.

In certain embodiments, the present invention relates to the aforementioned method and any of the attendant definitions, wherein R represents 5-chloro-3,6-diphenyl-2,4-diazene; $R_1$ is —CH=$CH_2$; m is 0; and n is 0.

In certain embodiments, the present invention relates to the aforementioned method and any of the attendant definitions, wherein R represents 4-chlorobenzoyl; $R_1$ is —CH=$CH_2$; m is 0; and n is 0.

In certain embodiments, the present invention relates to the aforementioned method and any of the attendant definitions, wherein said nitroalkane is nitromethane, nitroethane, nitropropane or nitrobutane.

In certain embodiments, the present invention relates to the aforementioned method and any of the attendant definitions, wherein said nitroalkane is nitromethane or nitroethane.

In certain embodiments, the present invention relates to the aforementioned method and any of the attendant definitions, wherein said nitroalkane is nitromethane.

In certain embodiments, the present invention relates to the aforementioned method and any of the attendant definitions, wherein said prochiral aldehyde or prochiral ketone is represented by A:

wherein

X represents alkyl, aryl, heteroaryl, aralkyl, or heteroaralkyl; and

Z represents H, perfluoroalkyl, alkyl, aryl, heteroaryl, aralkyl, or heteroaralkyl.

In certain embodiments, the present invention relates to the aforementioned method and any of the attendant definitions, wherein said prochiral aldehyde or prochiral ketone is represented by A; and Z represents H or trifluoromethyl.

In certain embodiments, the present invention relates to the aforementioned method and any of the attendant definitions, wherein said prochiral aldehyde or prochiral ketone is represented by B:

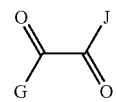

wherein

G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino;

J represents H, perfluoroalkyl, alkyl, aryl, heteroaryl, aralkyl, or heteroaralkyl; and G and J may be connected by a covalent bond to form a 4, 5, 6, 7, or 8-membered ring.

In certain embodiments, the present invention relates to the aforementioned method and any of the attendant definitions, wherein said prochiral aldehyde or prochiral ketone is represented by B; and J represents H.

In certain embodiments, the present invention relates to the aforementioned method and any of the attendant definitions, wherein said prochiral aldehyde or prochiral ketone is represented by B; and B represents cyclobutane-1,2-dione, cyclopentane-1,2-dione, cyclohexane-1,2-dione, cycloheptane-1,2-dione, or cyclooctane-1,2-dione.

In certain embodiments, the present invention relates to the aforementioned method and any of the attendant definitions, wherein said catalyst is present in less than about 70 mol % relative to said prochiral aldehyde or prochiral ketone.

In certain embodiments, the present invention relates to the aforementioned method and any of the attendant definitions, wherein said catalyst is present in less than about 40 mol % relative to said prochiral aldehyde or prochiral ketone.

In certain embodiments, the present invention relates to the aforementioned method and any of the attendant definitions, wherein said catalyst is present in less than about 10 mol % relative to said prochiral aldehyde or prochiral ketone.

In certain embodiments, the present invention relates to the aforementioned method and any of the attendant definitions, wherein said catalyst is present in less than about 5 mol % relative to said prochiral aldehyde or prochiral ketone.

In certain embodiments, the present invention relates to the aforementioned method and any of the attendant definitions, wherein said chiral, non-racemic alcohol has an enantiomeric excess or diastereomeric excess greater than about 50%.

In certain embodiments, the present invention relates to the aforementioned method and any of the attendant definitions, wherein said chiral, non-racemic alcohol has an enantiomeric excess or diastereomeric excess greater than about 70%.

In certain embodiments, the present invention relates to the aforementioned method and any of the attendant definitions, wherein said chiral, non-racemic alcohol has an enantiomeric excess or diastereomeric excess greater than about 90%.

In certain embodiments, the present invention relates to the aforementioned method and any of the attendant definitions, wherein said chiral, non-racemic alcohol has an enantiomeric excess or diastereomeric excess greater than about 95%.

One aspect of the present invention relates to a method of preparing a chiral, non-racemic alcohol from a prochiral aldehyde or prochiral ketone, comprising the step of:

reacting a prochiral aldehyde or prochiral ketone with a nucleophile in the presence of a catalyst; thereby producing a chiral, non-racemic alcohol; wherein said catalyst is represented by formula III:

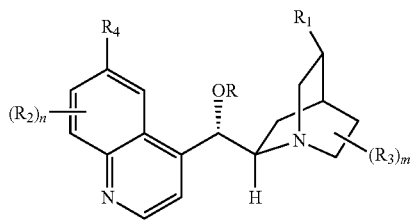

III wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, or —C(=O)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —NH$_2$, —NHR$_2$—NH(C=O)NR$_2$R$_3$, —NH(SO$_2$)R$_2$, —NH(C=O)OR$_2$, or —NH(C=O)R$_2$;

and said nucleophile is represented by formula IV:

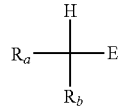

IV wherein, independently for each occurrence:

E represents —NO$_2$, —C(=O)OR$_c$, —C(=O)N(R$_c$)$_2$, —C(=O)SR$_c$, or —CN;

$R_a$ represents H, —CF$_3$, —NO$_2$, —C(=O)OR$_c$, —C(=O)N(R$_c$)$_2$, —C(=O)SR$_c$, or —CN, or a substituted or unsubstituted alkyl, alkenyl, alkynyl, aryl, aralkyl, heteroaryl, heteroaralkyl, heterocyclic, or heterocycloalkyl;

$R_b$ represents H or a substituted or unsubstituted alkyl, alkenyl, alkynyl, aryl, aralkyl, heteroaryl, heteroaralkyl, heterocyclic, or heterocycloalkyl; and $R_c$ represents H or a substituted or unsubstituted alkyl, alkenyl, alkynyl, aryl, aralkyl, heteroaryl, heteroaralkyl, heterocyclic, or heterocycloalkyl.

In certain embodiments, the present invention relates to the aforementioned method and any of the attendant definitions, wherein $R_4$ represents —OH.

In certain embodiments, the present invention relates to the aforementioned method and any of the attendant definitions, wherein R represents aryl or heteroaryl.

In certain embodiments, the present invention relates to the aforementioned method and any of the attendant definitions, wherein R represents aryl.

In certain embodiments, the present invention relates to the aforementioned method and any of the attendant definitions, wherein R represents substituted or unsubstituted phenyl.

In certain embodiments, the present invention relates to the aforementioned method and any of the attendant definitions, wherein R represents mono-substituted phenyl.

In certain embodiments, the present invention relates to the aforementioned method and any of the attendant definitions, wherein R represents unsubstituted phenyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is substituted or unsubstituted phenyl and $R_1$ is alkyl.

In certain embodiments, the present invention relates to the aforementioned method and any of the attendant definitions, wherein R is unsubstituted phenyl and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is substituted or unsubstituted phenyl and $R_1$ is alkenyl.

In certain embodiments, the present invention relates to the aforementioned method and any of the attendant definitions, wherein R is unsubstituted phenyl and $R_1$ is —CH=$CH_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is substituted or unsubstituted phenyl, $R_1$ is alkyl, m is 0, and n is 0.

In certain embodiments, the present invention relates to the aforementioned method and any of the attendant definitions, wherein R is unsubstituted phenyl, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is substituted or unsubstituted phenyl, $R_1$ is alkenyl, m is 0, and n is 0.

In certain embodiments, the present invention relates to the aforementioned method and any of the attendant definitions, wherein R is unsubstituted phenyl, $R_1$ is —CH=$CH_2$, m is 0, and n is 0.

In certain embodiments, the present invention relates to the aforementioned method and any of the attendant definitions, wherein E is —$NO_2$.

In certain embodiments, the present invention relates to the aforementioned method and any of the attendant definitions, wherein $R_b$ is H.

In certain embodiments, the present invention relates to the aforementioned method and any of the attendant definitions, wherein $R_a$ is alkyl, aralkyl or heteroaralkyl.

In certain embodiments, the present invention relates to the aforementioned method and any of the attendant definitions, wherein $R_a$ is alkyl.

In certain embodiments, the present invention relates to the aforementioned method and any of the attendant definitions, wherein E is —$NO_2$, $R_a$ is alkyl, and $R_b$ is H.

In certain embodiments, the present invention relates to the aforementioned method and any of the attendant definitions, wherein E is —$NO_2$, $R_a$ is H, and $R_b$ is H.

In certain embodiments, the present invention relates to the aforementioned method and any of the attendant definitions, wherein said prochiral aldehyde or prochiral ketone is electron-deficient.

In certain embodiments, the present invention relates to the aforementioned method and any of the attendant definitions, wherein said prochiral aldehyde or prochiral ketone is represented by formula V:

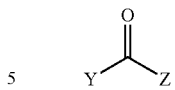

wherein, independently for each occurrence:

Y represents H or a substituted or unsubstituted alkyl, alkenyl, alkynyl, aryl, aralkyl, heteroaryl, heteroaralkyl, heterocyclic, or heterocycloalkyl; and Z represents —$CF_3$, —C(=O)OW, —C(=O)N(W)$_2$, —C(=O)SW, or —CN, or a substituted or unsubstituted alkyl, alkenyl, alkynyl, aryl, aralkyl, heteroaryl, heteroaralkyl, heterocyclic, or heterocycloalkyl; and W represents H or a substituted or unsubstituted alkyl, alkenyl, alkynyl, aryl, aralkyl, heteroaryl, heteroaralkyl, heterocyclic, or heterocycloalkyl.

In certain embodiments, the present invention relates to the aforementioned method, wherein Y is alkyl, alkenyl, aryl, or aralkyl.

In certain embodiments, the present invention relates to the aforementioned method, wherein Y is $CH_3$(H)=C(H)—, BnO$CH_2$C(H)=C(H)—, Ph-, 4-MeO-Ph-, 4-MeS-Ph-, 4-Cl-Ph-, 3-Cl-Ph-, 2-Napthyl-, Me-, n-Pr—, PhCH$_2$CH$_2$—, or EtO$_2$CCH$_2$CH$_2$CH$_2$—.

In certain embodiments, the present invention relates to the aforementioned method, wherein Z is —C(=O)OW.

In certain embodiments, the present invention relates to the aforementioned method, wherein Z is —C(=O)OW, and W is alkyl.

In certain embodiments, the present invention relates to the aforementioned method, wherein Z is —C(=O)OEt.

In certain embodiments, the present invention relates to the aforementioned method, wherein Y is alkyl, alkenyl, aryl, or aralkyl, Z is —C(=O)OW, and W is alkyl.

In certain embodiments, the present invention relates to the aforementioned method, wherein Y is $CH_3$ (H)=C(H)—, BnO$CH_2$C(H)=C(H)—, Ph-, 4-MeO-Ph-, 4-MeS-Ph-, 4-Cl-Ph-, 3-Cl-Ph-, 2-Napthyl-, Me-, n-Pr—, PhCH$_2$CH$_2$—, or EtO$_2$CCH$_2$CH$_2$CH$_2$—, and Z is —C(=O)OEt.

In certain embodiments, the present invention relates to the aforementioned method and any of the attendant definitions, wherein said catalyst is present in less than about 70 mol % relative to said prochiral aldehyde or prochiral ketone.

In certain embodiments, the present invention relates to the aforementioned method and any of the attendant definitions, wherein said catalyst is present in less than about 40 mol % relative to said prochiral aldehyde or prochiral ketone.

In certain embodiments, the present invention relates to the aforementioned method and any of the attendant definitions, wherein said catalyst is present in less than about 10 mol % relative to said prochiral aldehyde or prochiral ketone.

In certain embodiments, the present invention relates to the aforementioned method and any of the attendant definitions, wherein said catalyst is present in less than about 5 mol % relative to said prochiral aldehyde or prochiral ketone.

In certain embodiments, the present invention relates to the aforementioned method and any of the attendant definitions, wherein said chiral, non-racemic alcohol has an enantiomeric excess or diastereomeric excess greater than about 50%.

In certain embodiments, the present invention relates to the aforementioned method and any of the attendant definitions, wherein said chiral, non-racemic alcohol has an enantiomeric excess or diastereomeric excess greater than about 70%.

In certain embodiments, the present invention relates to the aforementioned method and any of the attendant definitions, wherein said chiral, non-racemic alcohol has an enantiomeric excess or diastereomeric excess greater than about 90%.

In certain embodiments, the present invention relates to the aforementioned method and any of the attendant definitions, wherein said chiral, non-racemic alcohol has an enantiomeric excess or diastereomeric excess greater than about 95%.

In certain embodiments, the present invention relates to the aforementioned method and any of the attendant definitions, wherein said chiral, non-racemic alcohol has an enantiomeric excess or diastereomeric excess greater than about 97%.

Another aspect of the present invention relates to a method of preparing a chiral, non-racemic alcohol from a prochiral aldehyde or prochiral ketone, comprising the step of:

reacting a prochiral aldehyde or prochiral ketone with a nucleophile in the presence of a catalyst; thereby producing a chiral, non-racemic alcohol; wherein said catalyst is represented by formula VI:

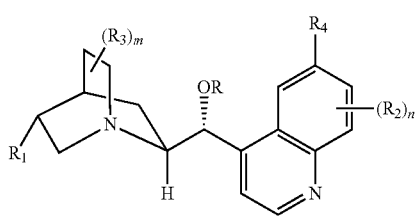

VI wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, or —C(=O)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —NH$_2$, —NHR$_2$—NH(C=O)NR$_2$R$_3$, —NH(SO$_2$)R$_2$, —NH(C=O)OR$_2$, or —NH(C=O)R$_2$;

and said nucleophile is represented by formula IV:

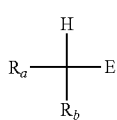

IV wherein, independently for each occurrence:

E represents —NO$_2$, —C(=O)OR$_c$, —C(=O)N(R$_c$)$_2$, —C(=O)SR$_c$, or —CN;

$R_a$ represents H, —CF$_3$, —NO$_2$, —C(=O)OR$_c$, —C(=O)N(R$_c$)$_2$, —C(=O)SR$_c$, or —CN, or a substituted or unsubstituted alkyl, alkenyl, alkynyl, aryl, aralkyl, heteroaryl, heteroaralkyl, heterocyclic, or heterocycloalkyl;

$R_b$ represents H or a substituted or unsubstituted alkyl, alkenyl, alkynyl, aryl, aralkyl, heteroaryl, heteroaralkyl, heterocyclic, or heterocycloalkyl; and $R_c$ represents H or a substituted or unsubstituted alkyl, alkenyl, alkynyl, aryl, aralkyl, heteroaryl, heteroaralkyl, heterocyclic, or heterocycloalkyl.

In certain embodiments, the present invention relates to the aforementioned method and any of the attendant definitions, wherein $R_4$ represents —OH.

In certain embodiments, the present invention relates to the aforementioned method and any of the attendant definitions, wherein R represents aryl or heteroaryl.

In certain embodiments, the present invention relates to the aforementioned method and any of the attendant definitions, wherein R represents aryl.

In certain embodiments, the present invention relates to the aforementioned method and any of the attendant definitions, wherein R represents substituted or unsubstituted phenyl.

In certain embodiments, the present invention relates to the aforementioned method and any of the attendant definitions, wherein R represents mono-substituted phenyl.

In certain embodiments, the present invention relates to the aforementioned method and any of the attendant definitions, wherein R represents unsubstituted phenyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is substituted or unsubstituted phenyl and $R_1$ is alkyl.

In certain embodiments, the present invention relates to the aforementioned method and any of the attendant definitions, wherein R is unsubstituted phenyl and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is substituted or unsubstituted phenyl and $R_1$ is alkenyl.

In certain embodiments, the present invention relates to the aforementioned method and any of the attendant definitions, wherein R is unsubstituted phenyl and $R_1$ is —CH=CH$_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is substituted or unsubstituted phenyl, $R_1$ is alkyl, m is 0, and n is 0.

In certain embodiments, the present invention relates to the aforementioned method and any of the attendant definitions, wherein R is unsubstituted phenyl, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is substituted or unsubstituted phenyl, $R_1$ is alkenyl, m is 0, and n is 0.

In certain embodiments, the present invention relates to the aforementioned method and any of the attendant definitions, wherein R is unsubstituted phenyl, $R_1$ is —CH=$CH_2$, m is 0, and n is 0.

In certain embodiments, the present invention relates to the aforementioned method and any of the attendant definitions, wherein E is —$NO_2$.

In certain embodiments, the present invention relates to the aforementioned method and any of the attendant definitions, wherein $R_b$ is H.

In certain embodiments, the present invention relates to the aforementioned method and any of the attendant definitions, wherein $R_a$ is alkyl, aralkyl or heteroaralkyl.

In certain embodiments, the present invention relates to the aforementioned method and any of the attendant definitions, wherein $R_a$ is alkyl.

In certain embodiments, the present invention relates to the aforementioned method and any of the attendant definitions, wherein E is —$NO_2$, $R_a$ is alkyl, and $R_b$ is H.

In certain embodiments, the present invention relates to the aforementioned method and any of the attendant definitions, wherein E is —$NO_2$, $R_a$ is H, and $R_b$ is H.

In certain embodiments, the present invention relates to the aforementioned method and any of the attendant definitions, wherein said prochiral aldehyde or prochiral ketone is electron-deficient.

In certain embodiments, the present invention relates to the aforementioned method and any of the attendant definitions, wherein said prochiral aldehyde or prochiral ketone is represented by formula V:

V wherein, independently for each occurrence:

Y represents H or a substituted or unsubstituted alkyl, alkenyl, alkynyl, aryl, aralkyl, heteroaryl, heteroaralkyl, heterocyclic, or heterocycloalkyl; and Z represents —$CF_3$, —C(=O)OW, —C(=O)N(W)$_2$, —C(=O)SW, or a substituted or unsubstituted alkyl, alkenyl, alkynyl, aryl, aralkyl, heteroaryl, heteroaralkyl, heterocyclic, or heterocycloalkyl; and W represents H or a substituted or unsubstituted alkyl, alkenyl, alkynyl, aryl, aralkyl, heteroaryl, heteroaralkyl, heterocyclic, or heterocycloalkyl.

In certain embodiments, the present invention relates to the aforementioned method, wherein Y is alkyl, alkenyl, aryl, or aralkyl.

In certain embodiments, the present invention relates to the aforementioned method, wherein Y is $CH_3(H)$=C(H)—, BnOCH$_2$C(H)=C(H)—, Ph-, 4-MeO-Ph-, 4-MeS-Ph-, 4-Cl-Ph-, 3-Cl-Ph-, 2-Napthyl-, Me-, n-Pr—, PhCH$_2$CH$_2$—, or EtO$_2$CCH$_2$CH$_2$CH$_2$—.

In certain embodiments, the present invention relates to the aforementioned method, wherein Z is —C(=O)OW.

In certain embodiments, the present invention relates to the aforementioned method, wherein Z is —C(=O)OW, and W is alkyl.

In certain embodiments, the present invention relates to the aforementioned method, wherein Z is —C(=O)OEt.

In certain embodiments, the present invention relates to the aforementioned method, wherein Y is alkyl, alkenyl, aryl, or aralkyl, Z is —C(=O)OW, and W is alkyl.

In certain embodiments, the present invention relates to the aforementioned method, wherein Y is $CH_3(H)$=C(H)—, BnOCH$_2$C(H)=C(H)—, Ph-, 4-MeO-Ph-, 4-MeS-Ph-, 4-Cl-Ph-, 3-Cl-Ph-, 2-Napthyl-, Me-, n-Pr—, PhCH$_2$CH$_2$—, or EtO$_2$CCH$_2$CH$_2$CH$_2$—, and Z is —C(=O)OEt.

In certain embodiments, the present invention relates to the aforementioned method and any of the attendant definitions, wherein said catalyst is present in less than about 70 mol % relative to said prochiral aldehyde or prochiral ketone.

In certain embodiments, the present invention relates to the aforementioned method and any of the attendant definitions, wherein said catalyst is present in less than about 40 mol % relative to said prochiral aldehyde or prochiral ketone.

In certain embodiments, the present invention relates to the aforementioned method and any of the attendant definitions, wherein said catalyst is present in less than about 10 mol % relative to said prochiral aldehyde or prochiral ketone.

In certain embodiments, the present invention relates to the aforementioned method and any of the attendant definitions, wherein said catalyst is present in less than about 5 mol % relative to said prochiral aldehyde or prochiral ketone.

In certain embodiments, the present invention relates to the aforementioned method and any of the attendant definitions, wherein said chiral, non-racemic alcohol has an enantiomeric excess or diastereomeric excess greater than about 50%.

In certain embodiments, the present invention relates to the aforementioned method and any of the attendant definitions, wherein said chiral, non-racemic alcohol has an enantiomeric excess or diastereomeric excess greater than about 70%.

In certain embodiments, the present invention relates to the aforementioned method and any of the attendant definitions, wherein said chiral, non-racemic alcohol has an enantiomeric excess or diastereomeric excess greater than about 90%.

In certain embodiments, the present invention relates to the aforementioned method and any of the attendant definitions, wherein said chiral, non-racemic alcohol has an enantiomeric excess or diastereomeric excess greater than about 95%.

In certain embodiments, the present invention relates to the aforementioned method and any of the attendant definitions, wherein said chiral, non-racemic alcohol has an enantiomeric excess or diastereomeric excess greater than about 97%.

Another aspect of the present invention relates to any one of the aforementioned methods of preparing a chiral, non-racemic alcohol from a prochiral aldehyde or prochiral ketone, wherein said catalyst is not represented by formula III or formula VI, but instead is represented by formula VII or formula VIII:

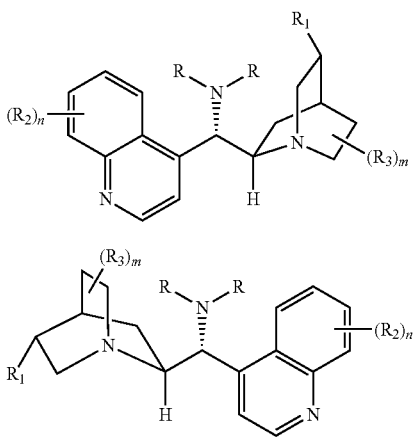

VII

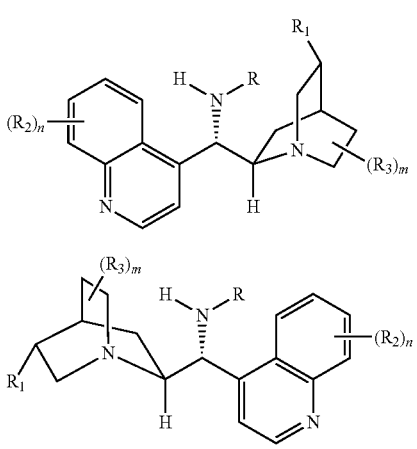

VIII wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(═O)-alkyl, —C(═O)-alkenyl, —C(═O)-alkynyl, —C(═O)-aryl, —C(═O)-aralkyl, —C(═O)-heteroaryl, —C(═O)-heteroaralkyl, —C(═O)-heterocyclic, —C(═O)-heterocycloalkyl, —C(═S)N(H)-alkyl, —C(═S)N(H)-alkenyl, —C(═S)N(H)-alkynyl, —C(═S)N(H)-aryl, —C(═S)N(H)-aralkyl, —C(═S)N(H)-heteroaryl, —C(═S) N(H)-heteroaralkyl, —C(═S)N(H)-heterocyclic, or —C(═S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 6 inclusive; and m is an integer from 0 to 8 inclusive.

Another aspect of the present invention relates to any one of the aforementioned methods of preparing a chiral, non-racemic alcohol from a prochiral aldehyde or prochiral ketone, wherein said catalyst is not represented by formula III or formula VI, but instead is represented by formula IX or formula X:

IX

X wherein, independently for each occurrence:

R represents —C(═S)N(H)-aryl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 6 inclusive; and m is an integer from 0 to 8 inclusive.

In certain embodiments, the present invention relates to the aforementioned method and any of the attendant definitions, wherein R is —C(═S)N(H)-monocyclic aryl.

In certain embodiments, the present invention relates to the aforementioned method and any of the attendant definitions, wherein R is selected from the group consisting of —C(═S) N(H)-(4-t-Bu-Ph), —C(═S)N(H)-(2-i-Pr-Ph), —C(═S)N (H)-(2-i-Pr-Ph), —C(═S)N(H)-(Ph), and —C(═S)N(H)-(3, 5-bis $CF_3$-Ph).

Figure 11:
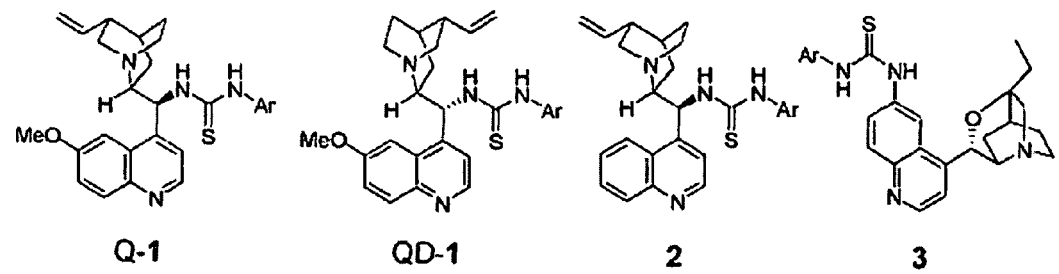
FIG. 11 depicts selected C6' or C9 thiourea chincona alkaloid derivatives which may be used as catalysts in the inventive methods.

In certain embodiments, the present invention relates to the aforementioned method and any of the attendant definitions, wherein said catalysts are selected from one of the six catalysts shown in FIG. 11.

Methods of Invention—Kinetic Resolution

In another aspect of the present invention, a kinetic resolution of enantiomers or diastereomers of the substrate or the nucleophile occurs by catalysis, using a subject chiral catalyst, of the transformation of a racemic substrate. In the subject kinetic resolution processes for a racemic substrate, one enantiomer can be recovered as unreacted substrate while the other is transformed to the desired product. Of course, it will be appreciated that the kinetic resolution can be performed by removing the undesired enantiomer by reaction with a nucleophile, and recovering the desired enantiomer unchanged from the reaction mixture. One significant advantage of this approach is the ability to use inexpensive racemic starting materials rather than expensive, enantiomerically pure starting compounds. In certain embodiments, the subject catalysts may be used in kinetic resolutions of racemic substrates comprising a carbonyl moiety.

One aspect of the present invention relates to a method of kinetic resolution, comprising the step of:

reacting a racemic aldehyde or racemic ketone with a nitroalkane in the presence of a catalyst; thereby producing a chiral, non-racemic alcohol; wherein said catalyst is represented by formula I:

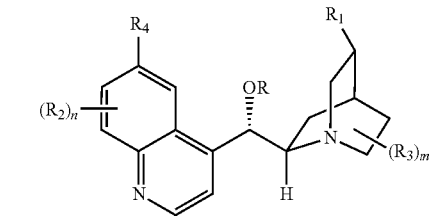

I wherein, independently for each occurrence:

R represents substituted or unsubstituted aryl, heteroaryl, aralkyl, heteroaralkyl, arylcarbonyl, or heteroarylcarbonyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH.

In certain embodiments, the present invention relates to the aforementioned method and any of the attendant definitions, wherein R represents phenanthrene.

In certain embodiments, the present invention relates to the aforementioned method and any of the attendant definitions, wherein R represents substituted or unsubstituted diazene.

In certain embodiments, the present invention relates to the aforementioned method and any of the attendant definitions, wherein R represents 5-chloro-3,6-diphenyl-2,4-diazene.

In certain embodiments, the present invention relates to the aforementioned method and any of the attendant definitions, wherein R represents halobenzoyl.

In certain embodiments, the present invention relates to the aforementioned method and any of the attendant definitions, wherein R represents 4-chlorobenzoyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is diazene and $R_1$ is ethyl.

In certain embodiments, the present invention relates to the aforementioned method and any of the attendant definitions, wherein R is halobenzoyl and $R_1$ is ethyl.

In certain embodiments, the present invention relates to the aforementioned method and any of the attendant definitions, wherein R represents 5-chloro-3,6-diphenyl-2,4-diazene; and R1 is ethyl.

In certain embodiments, the present invention relates to the aforementioned method and any of the attendant definitions, wherein R represents 4-chlorobenzoyl; and $R_1$ is ethyl.

In certain embodiments, the present invention relates to the aforementioned method and any of the attendant definitions, wherein R is phenanthrene and $R_1$ is —CH=CH$_2$.

In certain embodiments, the present invention relates to the aforementioned method and any of the attendant definitions, wherein R is diazene and $R_1$ is —CH=CH$_2$.

In certain embodiments, the present invention relates to the aforementioned method and any of the attendant definitions, wherein R is halobenzoyl and $R_1$ is —CH=CH$_2$.

In certain embodiments, the present invention relates to the aforementioned method and any of the attendant definitions, wherein R represents 5-chloro-3,6-diphenyl-2,4-diazene; and R1 is —CH=CH$_2$.

In certain embodiments, the present invention relates to the aforementioned method and any of the attendant definitions, wherein R represents 4-chlorobenzoyl; and $R_1$ is —CH=CH$_2$.

In certain embodiments, the present invention relates to the aforementioned method and any of the attendant definitions, wherein R is phenanthrene; $R_1$ is ethyl; m is 0; and n is 0.

In certain embodiments, the present invention relates to the aforementioned method and any of the attendant definitions, wherein R is diazene; $R_1$ is ethyl; m is 0; and n is 0.

In certain embodiments, the present invention relates to the aforementioned method and any of the attendant definitions, wherein R is halobenzoyl; $R_1$ is ethyl; m is 0; and n is 0.

In certain embodiments, the present invention relates to the aforementioned method and any of the attendant definitions, wherein R represents 5-chloro-3,6-diphenyl-2,4-diazene; $R_1$ is ethyl; m is 0; and n is 0.

In certain embodiments, the present invention relates to the aforementioned method and any of the attendant definitions, wherein R represents 4-chlorobenzoyl; $R_1$ is ethyl; m is 0; and n is 0.

In certain embodiments, the present invention relates to the aforementioned method and any of the attendant definitions, wherein R is phenanthrene; $R_1$ is —CH=CH$_2$; m is 0; and n is 0.

In certain embodiments, the present invention relates to the aforementioned method and any of the attendant definitions, wherein R is diazene; $R_1$ is —CH=CH$_2$; m is 0; and n is 0.

In certain embodiments, the present invention relates to the aforementioned method and any of the attendant definitions, wherein R is halobenzoyl; $R_1$ is —CH=CH$_2$; m is 0; and n is 0.

In certain embodiments, the present invention relates to the aforementioned method and any of the attendant definitions, wherein R represents 5-chloro-3,6-diphenyl-2,4-diazene; $R_1$ is —CH=CH$_2$; m is 0; and n is 0.

In certain embodiments, the present invention relates to the aforementioned method and any of the attendant definitions, wherein R represents 4-chlorobenzoyl; $R_1$ is —CH=CH$_2$; m is 0; and n is 0.

In certain embodiments, the present invention relates to the aforementioned method and any of the attendant definitions, wherein said nitroalkane is nitromethane, nitroethane, nitropropane or nitrobutane.

In certain embodiments, the present invention relates to the aforementioned method and any of the attendant definitions, wherein said nitroalkane is nitromethane or nitroethane.

In certain embodiments, the present invention relates to the aforementioned method and any of the attendant definitions, wherein said nitroalkane is nitromethane.

In certain embodiments, the present invention relates to the aforementioned method and any of the attendant definitions, wherein said racemic aldehyde or racemic ketone is represented by A:

A wherein

X represents alkyl, aryl, heteroaryl, aralkyl, or heteroaralkyl; and

Z represents H, perfluoroalkyl, alkyl, aryl, heteroaryl, aralkyl, or heteroaralkyl.

In certain embodiments, the present invention relates to the aforementioned method and any of the attendant definitions, wherein said racemic aldehyde or racemic ketone is represented by A; and Z represents H or trifluoromethyl.

In certain embodiments, the present invention relates to the aforementioned method and any of the attendant definitions, wherein said racemic aldehyde or racemic ketone is represented by B:

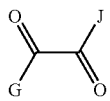

B wherein

G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino;

J represents H, perfluoroalkyl, alkyl, aryl, heteroaryl, aralkyl, or heteroaralkyl; and G and J may be connected by a covalent bond to form a 4, 5, 6, 7, or 8-membered ring.

In certain embodiments, the present invention relates to the aforementioned method and any of the attendant definitions, wherein said racemic aldehyde or racemic ketone is represented by B; and J represents H.

In certain embodiments, the present invention relates to the aforementioned method and any of the attendant definitions, wherein said racemic aldehyde or racemic ketone is represented by B; and B represents cyclobutane-1,2-dione, cyclopentane-1,2-dione, cyclohexane-1,2-dione, cycloheptane-1,2-dione, or cyclooctane-1,2-dione.

In certain embodiments, the present invention relates to the aforementioned method and any of the attendant definitions, wherein said catalyst is present in less than about 70 mol % relative to said racemic aldehyde or racemic ketone.

In certain embodiments, the present invention relates to the aforementioned method and any of the attendant definitions, wherein said catalyst is present in less than about 40 mol % relative to said racemic aldehyde or racemic ketone.

In certain embodiments, the present invention relates to the aforementioned method and any of the attendant definitions, wherein said catalyst is present in less than about 10 mol % relative to said racemic aldehyde or racemic ketone.

In certain embodiments, the present invention relates to the aforementioned method and any of the attendant definitions, wherein said catalyst is present in less than about 5 mol % relative to said racemic aldehyde or racemic ketone.

In certain embodiments, the present invention relates to the aforementioned method and any of the attendant definitions, wherein said chiral, non-racemic alcohol has an enantiomeric excess or diastereomeric excess greater than about 50%.

In certain embodiments, the present invention relates to the aforementioned method and any of the attendant definitions, wherein said chiral, non-racemic alcohol has an enantiomeric excess or diastereomeric excess greater than about 70%.

In certain embodiments, the present invention relates to the aforementioned method and any of the attendant definitions, wherein said chiral, non-racemic alcohol has an enantiomeric excess or diastereomeric excess greater than about 90%.

In certain embodiments, the present invention relates to the aforementioned method and any of the attendant definitions, wherein said chiral, non-racemic alcohol has an enantiomeric excess or diastereomeric excess greater than about 95%.

In certain embodiments, the present invention relates to the aforementioned method and any of the attendant definitions, wherein when said method is completed or interrupted the unreacted aldehyde or ketone is not racemic, and the enantiomeric excess or diastereomeric excess of the product is greater than zero.

In certain embodiments, the present invention relates to the aforementioned method and any of the attendant definitions, wherein when said method is completed or interrupted, the unreacted aldehyde or ketone is racemic, and the enantiomeric excess or diastereomeric excess of the product is greater than zero.

One aspect of the present invention relates to a method of kinetic resolution, comprising the step of:

reacting a racemic aldehyde or racemic ketone with a nitroalkane in the presence of a catalyst; thereby producing a chiral, non-racemic alcohol; wherein said catalyst is represented by formula II:

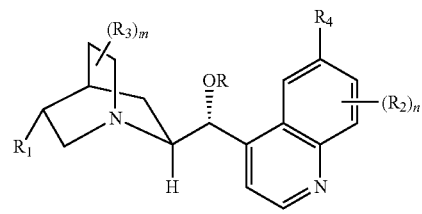

II wherein, independently for each occurrence:

R represents substituted or unsubstituted aryl, heteroaryl, aralkyl, heteroaralkyl, arylcarbonyl, or heteroarylcarbonyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH.

In certain embodiments, the present invention relates to the aforementioned method and any of the attendant definitions, wherein R represents phenanthrene.

In certain embodiments, the present invention relates to the aforementioned method and any of the attendant definitions, wherein R represents substituted or unsubstituted diazene.

In certain embodiments, the present invention relates to the aforementioned method and any of the attendant definitions, wherein R represents 5-chloro-3,6-diphenyl-2,4-diazene.

In certain embodiments, the present invention relates to the aforementioned method and any of the attendant definitions, wherein R represents halobenzoyl.

In certain embodiments, the present invention relates to the aforementioned method and any of the attendant definitions, wherein R represents 4-chlorobenzoyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is diazene and $R_1$ is ethyl.

In certain embodiments, the present invention relates to the aforementioned method and any of the attendant definitions, wherein R is halobenzoyl and $R_1$ is ethyl.

In certain embodiments, the present invention relates to the aforementioned method and any of the attendant definitions, wherein R represents 5-chloro-3,6-diphenyl-2,4-diazene; and R1 is ethyl.

In certain embodiments, the present invention relates to the aforementioned method and any of the attendant definitions, wherein R represents 4-chlorobenzoyl; and $R_1$ is ethyl.

In certain embodiments, the present invention relates to the aforementioned method and any of the attendant definitions, wherein R is phenanthrene and $R_1$ is —CH=CH$_2$.

In certain embodiments, the present invention relates to the aforementioned method and any of the attendant definitions, wherein R is diazene and $R_1$ is —CH=CH$_2$.

In certain embodiments, the present invention relates to the aforementioned method and any of the attendant definitions, wherein R is halobenzoyl and $R_1$ is —CH=CH$_2$.

In certain embodiments, the present invention relates to the aforementioned method and any of the attendant definitions, wherein R represents 5-chloro-3,6-diphenyl-2,4-diazene; and R1 is —CH=CH$_2$.

In certain embodiments, the present invention relates to the aforementioned method and any of the attendant definitions, wherein R represents 4-chlorobenzoyl; and $R_1$ is —CH=CH$_2$.

In certain embodiments, the present invention relates to the aforementioned method and any of the attendant definitions, wherein R is phenanthrene; $R_1$ is ethyl; m is 0; and n is 0.

In certain embodiments, the present invention relates to the aforementioned method and any of the attendant definitions, wherein R is diazene; $R_1$ is ethyl; m is 0; and n is 0.

In certain embodiments, the present invention relates to the aforementioned method and any of the attendant definitions, wherein R is halobenzoyl; $R_1$ is ethyl; m is 0; and n is 0.

In certain embodiments, the present invention relates to the aforementioned method and any of the attendant definitions, wherein R represents 5-chloro-3,6-diphenyl-2,4-diazene; $R_1$ is ethyl; m is 0; and n is 0.

In certain embodiments, the present invention relates to the aforementioned method and any of the attendant definitions, wherein R represents 4-chlorobenzoyl; $R_1$ is ethyl; m is 0; and n is 0.

In certain embodiments, the present invention relates to the aforementioned method and any of the attendant definitions, wherein R is phenanthrene; $R_1$ is —CH=CH$_2$; m is 0; and n is 0.

In certain embodiments, the present invention relates to the aforementioned method and any of the attendant definitions, wherein R is diazene; $R_1$ is —CH=CH$_2$; m is 0; and n is 0.

In certain embodiments, the present invention relates to the aforementioned method and any of the attendant definitions, wherein R is halobenzoyl; $R_1$ is —CH=CH$_2$; m is 0; and n is 0.

In certain embodiments, the present invention relates to the aforementioned method and any of the attendant definitions, wherein R represents 5-chloro-3,6-diphenyl-2,4-diazene; $R_1$ is —CH=CH$_2$; m is 0; and n is 0.

In certain embodiments, the present invention relates to the aforementioned method and any of the attendant definitions, wherein R represents 4-chlorobenzoyl; $R_1$ is —CH=CH$_2$; m is 0; and n is 0.

In certain embodiments, the present invention relates to the aforementioned method and any of the attendant definitions, wherein said nitroalkane is nitromethane, nitroethane, nitropropane or nitrobutane.

In certain embodiments, the present invention relates to the aforementioned method and any of the attendant definitions, wherein said nitroalkane is nitromethane or nitroethane.

In certain embodiments, the present invention relates to the aforementioned method and any of the attendant definitions, wherein said nitroalkane is nitromethane.

In certain embodiments, the present invention relates to the aforementioned method and any of the attendant definitions, wherein said racemic aldehyde or racemic ketone is represented by A:

A wherein

X represents alkyl, aryl, heteroaryl, aralkyl, or heteroaralkyl; and

Z represents H, perfluoroalkyl, alkyl, aryl, heteroaryl, aralkyl, or heteroaralkyl.

In certain embodiments, the present invention relates to the aforementioned method and any of the attendant definitions, wherein said racemic aldehyde or racemic ketone is represented by A; and Z represents H or trifluoromethyl.

In certain embodiments, the present invention relates to the aforementioned method and any of the attendant definitions, wherein said racemic aldehyde or racemic ketone is represented by B:

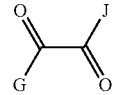

B wherein

G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino;

J represents H, perfluoroalkyl, alkyl, aryl, heteroaryl, aralkyl, or heteroaralkyl; and G and J may be connected by a covalent bond to form a 4, 5, 6, 7, or 8-membered ring.

In certain embodiments, the present invention relates to the aforementioned method and any of the attendant definitions, wherein said racemic aldehyde or racemic ketone is represented by B; and J represents H.

In certain embodiments, the present invention relates to the aforementioned method and any of the attendant definitions, wherein said racemic aldehyde or racemic ketone is represented by B; and B represents cyclobutane-1,2-dione, cyclopentane-1,2-dione, cyclohexane-1,2-dione, cycloheptane-1,2-dione, or cyclooctane-1,2-dione.

In certain embodiments, the present invention relates to the aforementioned method and any of the attendant definitions, wherein said catalyst is present in less than about 70 mol % relative to said racemic aldehyde or racemic ketone.

In certain embodiments, the present invention relates to the aforementioned method and any of the attendant definitions, wherein said catalyst is present in less than about 40 mol % relative to said racemic aldehyde or racemic ketone.

In certain embodiments, the present invention relates to the aforementioned method and any of the attendant definitions, wherein said catalyst is present in less than about 10 mol % relative to said racemic aldehyde or racemic ketone.

In certain embodiments, the present invention relates to the aforementioned method and any of the attendant definitions, wherein said catalyst is present in less than about 5 mol % relative to said racemic aldehyde or racemic ketone.

In certain embodiments, the present invention relates to the aforementioned method and any of the attendant definitions, wherein said chiral, non-racemic alcohol has an enantiomeric excess or diastereomeric excess greater than about 50%.

In certain embodiments, the present invention relates to the aforementioned method and any of the attendant definitions, wherein said chiral, non-racemic alcohol has an enantiomeric excess or diastereomeric excess greater than about 70%.

In certain embodiments, the present invention relates to the aforementioned method and any of the attendant definitions, wherein said chiral, non-racemic alcohol has an enantiomeric excess or diastereomeric excess greater than about 90%.

In certain embodiments, the present invention relates to the aforementioned method and any of the attendant definitions, wherein said chiral, non-racemic alcohol has an enantiomeric excess or diastereomeric excess greater than about 95%.

In certain embodiments, the present invention relates to the aforementioned method and any of the attendant definitions, wherein when said method is completed or interrupted the unreacted aldehyde or ketone is not racemic, and the enantiomeric excess or diastereomeric excess of the product is greater than zero.

In certain embodiments, the present invention relates to the aforementioned method and any of the attendant definitions, wherein when said method is completed or interrupted, the unreacted aldehyde or ketone is racemic, and the enantiomeric excess or diastereomeric excess of the product is greater than zero.

One aspect of the present invention relates to a method of kinetic resolution, comprising the step of:

reacting a racemic aldehyde or ketone with a nucleophile in the presence of a catalyst represented by formula III:

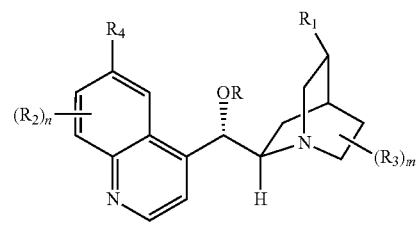

wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, or —C(=O)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —$NH_2$, —$NHR_2$—$NH(C=O)NR_2R_3$, —$NH(SO_2)R_2$, —$NH(C=O)OR_2$, or —$NH(C=O)R_2$;

and said nucleophile is represented by formula IV:

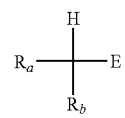

wherein, independently for each occurrence:

E represents —$NO_2$, —C(=O)$OR_c$, —C(=O)N($R_c$)$_2$, —C(=O)$SR_c$, or —CN;

$R_a$ represents H, —$CF_3$, —$NO_2$, —C(=O)$OR_c$, —C(=O)N($R_c$)$_2$, —C(=O)$SR_c$, or —CN, or a substituted or unsubstituted alkyl, alkenyl, alkynyl, aryl, aralkyl, heteroaryl, heteroaralkyl, heterocyclic, or heterocycloalkyl;

$R_b$ represents H or a substituted or unsubstituted alkyl, alkenyl, alkynyl, aryl, aralkyl, heteroaryl, heteroaralkyl, heterocyclic, or heterocycloalkyl; and $R_c$ represents H or a substituted or unsubstituted alkyl, alkenyl, alkynyl, aryl, aralkyl, heteroaryl, heteroaralkyl, heterocyclic, or heterocycloalkyl.

In certain embodiments, the present invention relates to the aforementioned method and any of the attendant definitions, wherein $R_4$ represents —OH.

In certain embodiments, the present invention relates to the aforementioned method and any of the attendant definitions, wherein R represents aryl or heteroaryl.

In certain embodiments, the present invention relates to the aforementioned method and any of the attendant definitions, wherein R represents aryl.

In certain embodiments, the present invention relates to the aforementioned method and any of the attendant definitions, wherein R represents substituted or unsubstituted phenyl.

In certain embodiments, the present invention relates to the aforementioned method and any of the attendant definitions, wherein R represents mono-substituted phenyl.

In certain embodiments, the present invention relates to the aforementioned method and any of the attendant definitions, wherein R represents unsubstituted phenyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is substituted or unsubstituted phenyl and $R_1$ is alkyl.

In certain embodiments, the present invention relates to the aforementioned method and any of the attendant definitions, wherein R is unsubstituted phenyl and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is substituted or unsubstituted phenyl and $R_1$ is alkenyl.

In certain embodiments, the present invention relates to the aforementioned method and any of the attendant definitions, wherein R is unsubstituted phenyl and $R_1$ is —CH=CH$_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is substituted or unsubstituted phenyl, $R_1$ is alkyl, m is 0, and n is 0.

In certain embodiments, the present invention relates to the aforementioned method and any of the attendant definitions, wherein R is unsubstituted phenyl, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is substituted or unsubstituted phenyl, $R_1$ is alkenyl, m is 0, and n is 0.

In certain embodiments, the present invention relates to the aforementioned method and any of the attendant definitions, wherein R is unsubstituted phenyl, $R_1$ is —CH=CH$_2$, m is 0, and n is 0.

In certain embodiments, the present invention relates to the aforementioned method and any of the attendant definitions, wherein E is —NO$_2$.

In certain embodiments, the present invention relates to the aforementioned method and any of the attendant definitions, wherein $R_b$ is H.

In certain embodiments, the present invention relates to the aforementioned method and any of the attendant definitions, wherein $R_a$ is alkyl, aralkyl or heteroaralkyl.

In certain embodiments, the present invention relates to the aforementioned method and any of the attendant definitions, wherein $R_a$ is alkyl.

In certain embodiments, the present invention relates to the aforementioned method and any of the attendant definitions, wherein E is —NO$_2$, $R_a$ is alkyl, and $R_b$ is H.

In certain embodiments, the present invention relates to the aforementioned method and any of the attendant definitions, wherein E is —NO$_2$, $R_a$ is H, and $R_b$ is H.

In certain embodiments, the present invention relates to the aforementioned method and any of the attendant definitions, wherein said aldehyde or ketone is electron-deficient.

In certain embodiments, the present invention relates to the aforementioned method and any of the attendant definitions, wherein said prochiral aldehyde or prochiral ketone is represented by formula V:

wherein, independently for each occurrence:

Y represents H or a substituted or unsubstituted alkyl, alkenyl, alkynyl, aryl, aralkyl, heteroaryl, heteroaralkyl, heterocyclic, or heterocycloalkyl; and Z represents —CF$_3$, —C(=O)OW, —C(=O)N(W)$_2$, —C(=O)SW, or a substituted or unsubstituted alkyl, alkenyl, alkynyl, aryl, aralkyl, heteroaryl, heteroaralkyl, heterocyclic, or heterocycloalkyl; and W represents H or a substituted or unsubstituted alkyl, alkenyl, alkynyl, aryl, aralkyl, heteroaryl, heteroaralkyl, heterocyclic, or heterocycloalkyl.

In certain embodiments, the present invention relates to the aforementioned method, wherein Y is alkyl, alkenyl, aryl, or aralkyl.

In certain embodiments, the present invention relates to the aforementioned method, wherein Z is —C(=O)OW.

In certain embodiments, the present invention relates to the aforementioned method, wherein Z is —C(=O)OW, and W is alkyl.

In certain embodiments, the present invention relates to the aforementioned method, wherein Z is —C(=O)OEt.

In certain embodiments, the present invention relates to the aforementioned method and any of the attendant definitions, wherein said catalyst is present in less than about 70 mol % relative to said aldehyde or ketone.

In certain embodiments, the present invention relates to the aforementioned method and any of the attendant definitions, wherein said catalyst is present in less than about 40 mol % relative to said aldehyde or ketone.

In certain embodiments, the present invention relates to the aforementioned method and any of the attendant definitions, wherein said catalyst is present in less than about 10 mol % relative to said aldehyde or ketone.

In certain embodiments, the present invention relates to the aforementioned method and any of the attendant definitions, wherein said catalyst is present in less than about 5 mol % relative to said aldehyde or ketone.

Another aspect of the present invention relates to a method of kinetic resolution, comprising the step of:

reacting a racemic aldehyde or ketone with a nucleophile in the presence of a catalyst represented by formula VI:

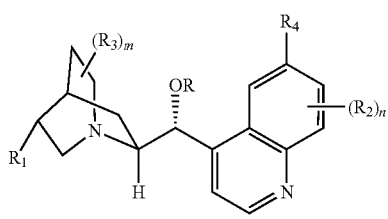

VI wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, or —C(=O)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —NH$_2$, —NHR$_2$—NH(C=O)NR$_2$R$_3$, —NH(SO$_2$)R$_2$, —NH(C=O)OR$_2$, or —NH(C=O)R$_2$;

and said nucleophile is represented by formula IV:

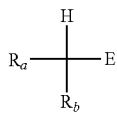

IV wherein, independently for each occurrence:

E represents —NO$_2$, —C(=O)OR$_c$, —C(=O)N(R$_c$)$_2$, —C(=O)SR$_c$, or —CN;

$R_a$ represents H, —CF$_3$, —NO$_2$, —C(=O)OR$_c$, —C(=O)N(R$_c$)$_2$, —C(=O)SR$_c$, or —CN, or a substituted or unsubstituted alkyl, alkenyl, alkynyl, aryl, aralkyl, heteroaryl, heteroaralkyl, heterocyclic, or heterocycloalkyl;

$R_b$ represents H or a substituted or unsubstituted alkyl, alkenyl, alkynyl, aryl, aralkyl, heteroaryl, heteroaralkyl, heterocyclic, or heterocycloalkyl; and $R_c$ represents H or a substituted or unsubstituted alkyl, alkenyl, alkynyl, aryl, aralkyl, heteroaryl, heteroaralkyl, heterocyclic, or heterocycloalkyl.

In certain embodiments, the present invention relates to the aforementioned method and any of the attendant definitions, wherein $R_4$ represents —OH.

In certain embodiments, the present invention relates to the aforementioned method and any of the attendant definitions, wherein R represents aryl or heteroaryl.

In certain embodiments, the present invention relates to the aforementioned method and any of the attendant definitions, wherein R represents aryl.

In certain embodiments, the present invention relates to the aforementioned method and any of the attendant definitions, wherein R represents substituted or unsubstituted phenyl.

In certain embodiments, the present invention relates to the aforementioned method and any of the attendant definitions, wherein R represents mono-substituted phenyl.

In certain embodiments, the present invention relates to the aforementioned method and any of the attendant definitions, wherein R represents unsubstituted phenyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is substituted or unsubstituted phenyl and $R_1$ is alkyl.

In certain embodiments, the present invention relates to the aforementioned method and any of the attendant definitions, wherein R is unsubstituted phenyl and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is substituted or unsubstituted phenyl and $R_1$ is alkenyl.

In certain embodiments, the present invention relates to the aforementioned method and any of the attendant definitions, wherein R is unsubstituted phenyl and $R_1$ is —CH=CH$_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is substituted or unsubstituted phenyl, $R_1$ is alkyl, m is 0, and n is 0.

In certain embodiments, the present invention relates to the aforementioned method and any of the attendant definitions, wherein R is unsubstituted phenyl, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is substituted or unsubstituted phenyl, $R_1$ is alkenyl, m is 0, and n is 0.

In certain embodiments, the present invention relates to the aforementioned method and any of the attendant definitions, wherein R is unsubstituted phenyl, $R_1$ is —CH=$CH_2$, m is 0, and n is 0.

In certain embodiments, the present invention relates to the aforementioned method and any of the attendant definitions, wherein E is —$NO_2$.

In certain embodiments, the present invention relates to the aforementioned method and any of the attendant definitions, wherein $R_b$ is H.

In certain embodiments, the present invention relates to the aforementioned method and any of the attendant definitions, wherein $R_a$ is alkyl, aralkyl or heteroaralkyl.

In certain embodiments, the present invention relates to the aforementioned method and any of the attendant definitions, wherein $R_a$ is alkyl.

In certain embodiments, the present invention relates to the aforementioned method and any of the attendant definitions, wherein E is —$NO_2$, $R_a$ is alkyl, and $R_b$ is H.

In certain embodiments, the present invention relates to the aforementioned method and any of the attendant definitions, wherein E is —$NO_2$, $R_a$ is H, and $R_b$ is H.

In certain embodiments, the present invention relates to the aforementioned method and any of the attendant definitions, wherein said aldehyde or ketone is electron-deficient.

In certain embodiments, the present invention relates to the aforementioned method and any of the attendant definitions, wherein said prochiral aldehyde or prochiral ketone is represented by formula V:

V wherein, independently for each occurrence:

Y represents H or a substituted or unsubstituted alkyl, alkenyl, alkynyl, aryl, aralkyl, heteroaryl, heteroaralkyl, heterocyclic, or heterocycloalkyl; and Z represents —$CF_3$, —C(=O)OW, —C(=O)N(W)$_2$, —C(=O)SW, or a substituted or unsubstituted alkyl, alkenyl, alkynyl, aryl, aralkyl, heteroaryl, heteroaralkyl, heterocyclic, or heterocycloalkyl; and W represents H or a substituted or unsubstituted alkyl, alkenyl, alkynyl, aryl, aralkyl, heteroaryl, heteroaralkyl, heterocyclic, or heterocycloalkyl.

In certain embodiments, the present invention relates to the aforementioned method, wherein Y is alkyl, alkenyl, aryl, or aralkyl.

In certain embodiments, the present invention relates to the aforementioned method, wherein Z is —C(=O)OW.

In certain embodiments, the present invention relates to the aforementioned method, wherein Z is —C(=O)OW, and W is alkyl.

In certain embodiments, the present invention relates to the aforementioned method, wherein Z is —C(=O)OEt.

In certain embodiments, the present invention relates to the aforementioned method and any of the attendant definitions, wherein said catalyst is present in less than about 70 mol % relative to said aldehyde or ketone.

In certain embodiments, the present invention relates to the aforementioned method and any of the attendant definitions, wherein said catalyst is present in less than about 40 mol % relative to said aldehyde or ketone.

In certain embodiments, the present invention relates to the aforementioned method and any of the attendant definitions, wherein said catalyst is present in less than about 10 mol % relative to said aldehyde or ketone.

In certain embodiments, the present invention relates to the aforementioned method and any of the attendant definitions, wherein said catalyst is present in less than about 5 mol % relative to said aldehyde or ketone.

Another aspect of the present invention relates to any one of the aforementioned methods of kinetic resolution, wherein said catalyst is not represented by formula III or formula VI, but instead is represented by formula VII or formula VIII:

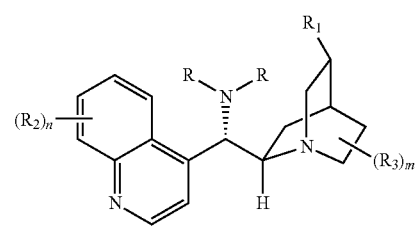

VII

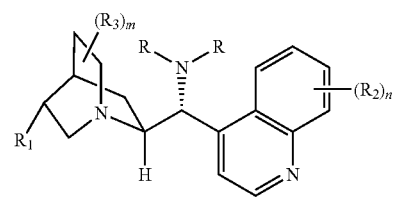

VIII wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S) N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 6 inclusive; and m is an integer from 0 to 8 inclusive.

Another aspect of the present invention relates to any one of the aforementioned methods of kinetic resolution, wherein said catalyst is not represented by formula III or formula VI, but instead is represented by formula IX or formula X:

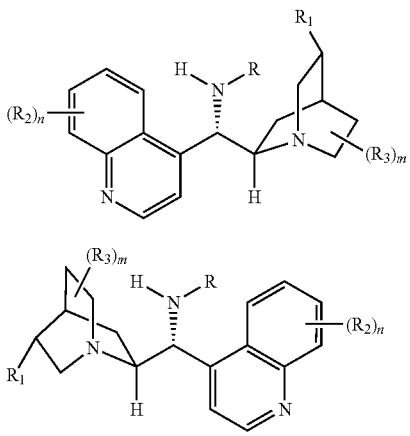

IX

X wherein, independently for each occurrence:

R represents —C(=S)N(H)-aryl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 6 inclusive; and m is an integer from 0 to 8 inclusive.

In certain embodiments, the present invention relates to the aforementioned method and any of the attendant definitions, wherein R is —C(=S)N(H)— monocyclic aryl.

In certain embodiments, the present invention relates to the aforementioned method and any of the attendant definitions, wherein R is selected from the group consisting of —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bis $CF_3$-Ph).

In certain embodiments, the present invention relates to the aforementioned method and any of the attendant definitions, wherein said catalysts are selected from one of the six catalysts shown in FIG. 11.

Nucleophiles

Nucleophiles which are useful in the present invention may be determined by the skilled artisan according to several criteria. Suitable nucleophiles can be chosen for each substrate and will vary according to the substrate structure and the desired product. Routine experimentation may be necessary to determine the preferred nucleophile for a given transformation. For example, if a nitrogen-containing nucleophile is desired, it may be selected from ammonia, phthalimide, hydrazine, an amine or the like. Similarly, oxygen nucleophiles such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Additional nucleophiles will be apparent to those of ordinary skill in the art. For nucleophiles which exist as anions, the counterion can be any of a variety of conventional cations, including alkali and alkaline earth metal cations and ammonium cations. In certain embodiments, the nucleophile may be part of the substrate, thus resulting in an intramolecular reaction. The nucleophile may be a primary, secondary, or tertiary nucleophile.

Substrates

As discussed above, a wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. In general, an appropriate substrate will contain at least one reactive electrophilic center or moiety with distinct stereogenic faces; or at least two electrophilic moieties related by an internal plane or point of symmetry or both at which a nucleophile may attack with the assistance of the catalyst. The catalyzed, stereoselective attack of the nucleophile at the electrophilic center will produce a chiral, non-racemic product. Most of the substrates contemplated for use in the methods of the present invention contain at least one carbonyl. The carbonyl-containing substrate, in some embodiments, will additionally comprise an electron withdrawing group making the carbonyl more susceptible to nucleophilic attack. Examples of suitable carbonyl-containing substrates which are susceptible to nucleophilic attack by the subject method include α-keto esters.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred. In embodiments where water or hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. For example, desymmetrization with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

Selected Enantioselective Nitroaldol Reactions

Although effective chiral organic catalysts have been reported for enantioselective aza-Henry reactions, no efficient chiral organic catalyst has been developed for the direct asymmetric Henry reaction. For a recent review on catalytic asymmetric aza-Henry reactions, see: Westermann, B. *Angew. Chem. Int. Ed.* 2003, 42, 151-153. For recent examples for catalytic asymmetric aza-Henry reactions with organic catalysts see: Yoon, T. P.; Jacobsen, E. N. *Angew. Chem. Int. Ed.* 2005, 44, 466-468; Nugent, B. M.; Yoder, R. A.; Johnston, J. N. *J. Am. Chem. Soc.* 2004, 126, 3418-3419; Okino, T.; Nakamura, S.; Furukawa, T.; Takemoto, Y. *Org. Lett.* 2004, 6, 625-627. C6'-OH cinchona alkaloids 1a-c (FIG. 1) were recently reported as efficient catalysts for various enantioselective conjugate additions. Li, H.; Wang, Y.; Tang, L.; Deng, L. *J. Am. Chem. Soc.* 2004, 126, 9906-9907; Li, H.; Wang, Y.; Tang, L.; Wu, F.; Liu, X.; Guo, C.; Foxman, B. M.; Deng L. *Angew. Chem. Int. Ed.* 2005, 44, 105-108; Liu, X.; Li, H.; Deng, L. *Org. Lett.* 2005, 7, 167-169; and Li, H.; Song, J.; Liu, X.; Deng, L. *J. Am. Chem. Soc.* 2005, 127, 8948-8949.

Figure 2:
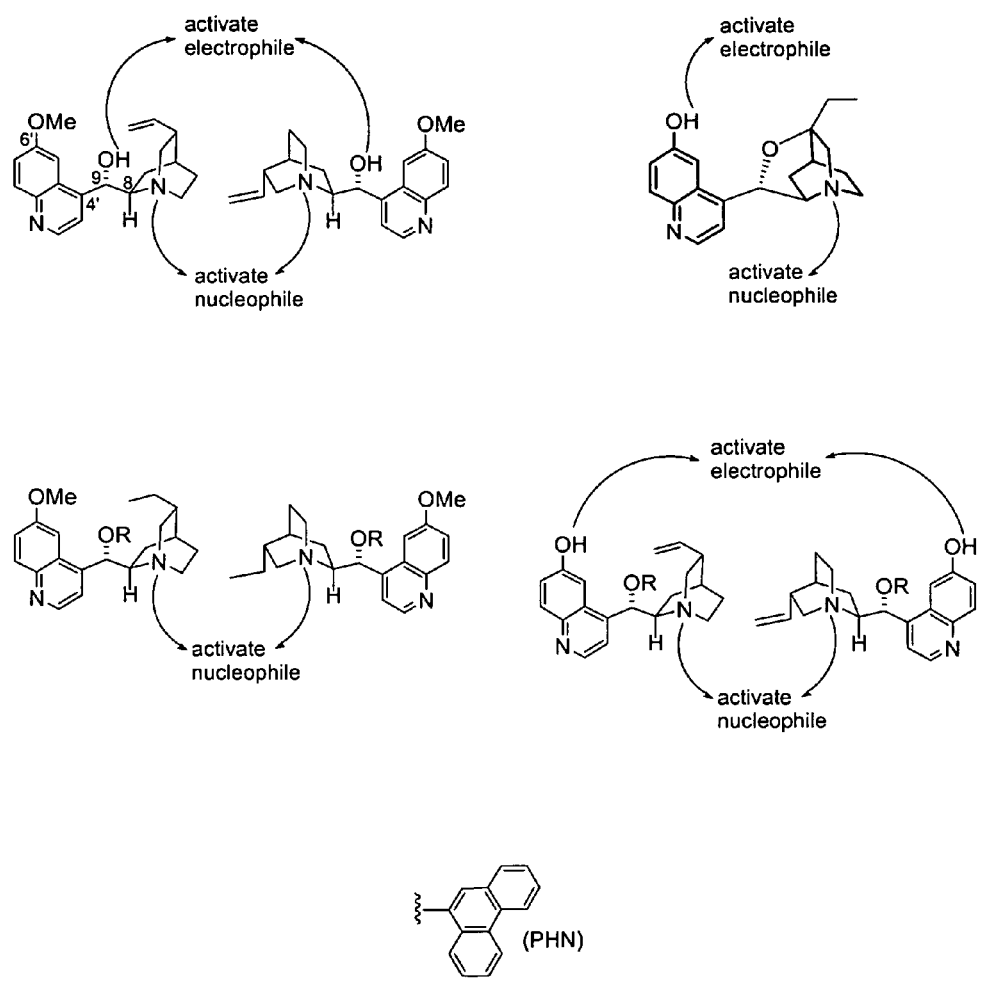
FIG. 2 depicts the bifunctional nature of several cinchona-alkaloid-based catalysts of the present invention; R=H (a); Bn (b); PHN (c); or Bz (d).

Mechanistic studies indicated that catalysts 1 could serve as acid-base bifunctional catalysts via hydrogen bonding interactions with the Michael donor and acceptor via the quinuclidine nitrogen and the C6'-OH, respectively (FIG. 2).

In one embodiment of the invention, nitromethane is added to alkenyl α-keto ester 2a. Interestingly, prior to this invention high enantioselectivity had not yet been achieved for nitroaldol reactions of this important class of α-keto esters. Furthermore, since alkenyl α-keto esters could engage in 1,2- as well as 1,4-additions with a nitroalkane, alkenyl α-keto esters present a particularly challenging class of substrates for nitroaldol reactions. As reported previously, nitromethane reacted with 2a in the presence of $Et_3N$ to give products 3a and 3a' in 4:1 ratio (entry 1, FIG. 3). Christensen, C.; Juhl, K.; Hazell, R. G.; Jørgensen, K. A. *J. Org. Chem.* 2002, 67, 4875-4881.

Figure 3:
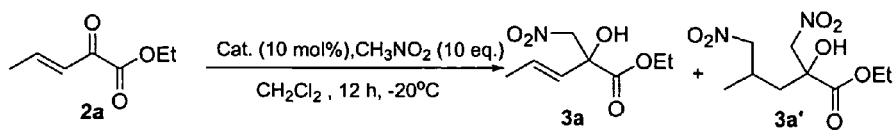
FIG. 3 depicts enantioselective nitroaldol addition of nitromethane to an α-keto ester. Unless noted, reactions were carried out with 0.1 mmol of 2a, 1 mmol $CH_3NO_2$ in 0.1 mL $CH_2Cl_2$ with 10 mol % catalyst at −20° C. for 12 h. Ratio of 3a/3a' were determined by $^1H$ NMR analysis. Enantiomeric excess for 3a was determined by HPLC analysis.

Promoted by various cinchona alkaloids the addition of nitromethane to 2a in methylene chloride was found to proceed in a highly chemoselective fashion to afford the nitroaldol product 3a (FIG. 3). The enantioselectivity of the C6'-OH cinchona alkaloids 1a-c was found to be considerably higher than that displayed by C6'-OMe cinchona alkaloids (entries 6-8 vs. 2-4, FIG. 3). Furthermore, the significant impact of the C9-substituent (OR) on the enantioselectivity of 1 raised the possibility of finding a more effective and practical C6'-OH cinchona alkaloid for the nitroaldol reaction by modifications of this substituent. Further studies following this hypothesis led to the discovery that C6'-OH cinchona alkaloid bearing a C9-OBz group (QD-1d) is even more effective than 1a-c. The addition of nitromethane to 2a with either QD-1d or Q-1d occurred in 97% ee (entries 9-10, FIG. 3). It is noteworthy that the preparation of 1d, as disclosed in the Exemplification below, employs significantly cheaper reagents than those required for the preparation of 1c.

Figure 4:
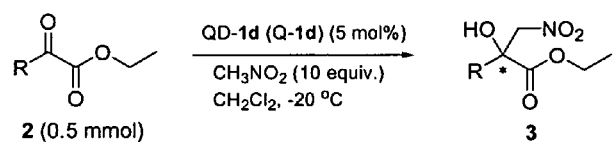
FIG. 4 depicts enantioselective nitroaldol addition of nitromethane to α-keto ester 2 catalyzed by QD-1d and Q-1d. Reactions were run with 0.5 mmol of 2, 5 mmol $CH_3NO_2$ on 0.5 mL $CH_2Cl_2$ with 5 mol % QD-1d, the results in parentheses were obtained with Q-1d, to give opposite enantiomer. In entries 3 and 6, * denotes the absolute configuration was determined to be S.

With 5.0 mol % of 1d, excellent enantioselectivity and high yield could be attained not only for alkenyl α-keto esters 2a-b, but also for a broad range of aryl and alkyl α-keto esters 2c-m (FIG. 4). Thus, the enantioselectivity of 1d is insensitive to either the steric or the electronic properties of 2. The unprecedented excellent enantioselectivity obtained with α-ketoesters 2 bearing electron-rich aryl, sterically bulky alkyl and alkenyl groups is noteworthy. Among them 2a, 2d and 2l were reported to react with nitromethane in 57-77% ee with existing catalyst systems, and enantioselective nitroaldol reaction was not documented for 2b, 2e and 2m. Christensen, C.; Juhl, K.; Jørgensen, K. A.; *Chem. Commun.* 2001, 2222-2223; Christensen, C.; Juhl, K.; Hazell, R. G.; Jørgensen, K. A. *J. Org Chem.* 2002, 67, 4875-4881; and Du. D. M.; Lu, S. F.; Fang, T.; Xu, J. X. *J. Org. Chem.* 2005, 70, 3712-3715.

Figure 5:
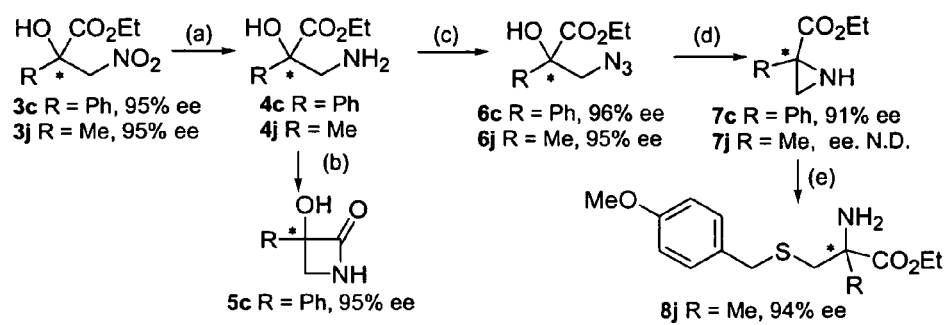
FIG. 5 depicts asymmetric syntheses of β-lactam, aziridine and α-methylcysteine derivatives. Key: (a) Raney Ni, $H_2$ (1 atm); (b) i-PrMgCl, 38% yield over 2 steps; (c) $TfN_3$, $CuSO_4$ (cat.), for 6c, 84% yield over 2 steps; for 6j, 63% yield over 2 steps; (d) $PPh_3$, $CH_3CN$, for 7c, 80% yield; for 7j, 71% yield; (e) $BF_3.Et2O$, p-methoxybenzyl mercaptan, 56% yield.

The 1d-catalyzed nitroaldol reaction was applied to develop new and concise asymmetric syntheses of synthetically important chiral intermediates such as aziridines 7 and β-lactams 5 (FIG. 5). Greenlee, W. J.; Springer, J. P.; Patchett, A. A. *J. Med. Chem.* 1989, 32, 165-170; and Kiyota, H.; Takai, T.; Saitoh, M.; Nakayama, O.; Oritani, T.; Kuwahara, S. *Tetrahedron Lett.* 2004, 45, 8191-8194. As shown by the conversion of 7j to 8j, optically active aziridines 7 are valuable intermediates for the synthesis of optically active α,α-disubstituted α-amino acids. It should be noted that α-methylcysteine (8j) was the key intermediate in the total syntheses of mirabazoles and thiangazole. Pattenden, G.; Thom, S. M. *Synlett* 1992, 533-534; Mulqueen, G. C.; Pattenden, G.; Whiting, D. A. *Tetrahedron,* 1993, 49, 5359-5364; Boyce, R. J.; Pattenden, G. *Synlett* 1994, 587-588; Boyce, R. J.; Mulqueen, G. C.; Pattenden, G. *Tetrahedron Lett.* 1994, 35, 5705-5708; Parsons, R. L.; Heathcock, C. H. *Tetrahedron Lett.* 1994, 35, 1379-1382; Parsons, R. L.; Heathcock, C. H. *Tetrahedron*

*Lett.* 1994, 35, 1383-1384; Parsons, R. L.; Heathcock, C. H. *J. Org. Chem.* 1994, 59, 4733-4734; and Shao, H.; Zhu, Q.; Goodman, M. *J. Org. Chem.* 1995, 60, 790-791. The ability of 1d to promote highly enantioselective nitroaldol reaction for a wide range of α-keto esters 2 should facilitate the preparations of analogues of these antitumor and anti-HIV natural products.

EXEMPLIFICATION

The invention now being generally described, it will be more readily understood by reference to the following examples which are included merely for purposes of illustration of certain aspects and embodiments of the present invention, and are not intended to limit the invention.

In the following Exemplification, $^1$H and $^{13}$C NMR spectra were recorded on a Varian instrument (400 MHz and 100 MHz, respectively) and internally referenced to tetramethylsilane signal or residual protio solvent signals. Data for $^1$H NMR are recorded as follows: chemical shift (δ, ppm), multiplicity (s, singlet; d, doublet; t, triplet; q, quartet; m, multiplet), intergration, coupling constant (Hz). Data for $^{13}$C NMR are reported in terms of chemical shift (δ, ppm). Infrared spectra were recorded on a Perkin Elmer FT-IR Spectrometer and are reported in frequency of absorption. Low resolution mass spectra for all the new compounds were performed by 70SE CI+, and were recorded and exact mass spectra on a 70-VSE-B high resolution mass spectrometer. Specific rotations were measured on a Jasco Digital Polarimeter. High performance liquid chromatography (HPLC) analysis was performed on a Hewlett-Packard 1100 Series instrument equipped with a quaternary pump, using a Daicel Chiralcel OJ, OD Column (250×4.6 mm) or Chiralpak AD, AS Column (250×4.6 mm). UV absorption was monitored at 220 nm or at 280 nm.

For the structures of α-keto esters 2 and for the structure of cinchona alkaloid catalysts see the Figures. α-Keto esters 2a and 2b were prepared according to literature procedures. Jesen, K. B.; Thorhauge, J.; Hazell, R. G.; Jørgensen, K. A. *Angew. Chem. Int. Ed.* 2001, 40, 160-163. The other α-keto esters 2 were commercially available and purified by flash chromatography (silica gel 60, 0.040 mm to 0.063 mm, purchased from EM SCIENCE Inc.) before they were used for the nitroaldol reaction. Catalysts QD, DHQD-PHN, (DHQD)$_2$ AQN were purchased from Aldrich company and used without any further purification. C6'-OH catalysts Q-1a-c and QD-1a-c were prepared following procedures previously reported and β-ICD was prepared according to literature procedures. Li, H.; Wang, Y.; Tang, L.; Deng, L. *J. Am. Chem. Soc.* 2004, 126, 9906-9907; Li, H.; Wang, Y.; Tang, L.; Wu, F.; Liu, X.; Guo, C.; Foxman, B. M.; Deng L. *Angew. Chem. Int. Ed.* 2005, 44, 105-108; Liu, X.; Li, H.; Deng, L. *Org. Lett.* 2005, 7, 167-169; and Iwabuchi, Y.; Nakatani, M.; Yokoyama, N.; Hatakeyama, S. *J. Am. Chem. Soc.* 1999, 121, 10219-10220. Petroleum ether (36-60° C.) for chromatography was purchased from Fisher Company.

Example 1

Preparation of Catalyst Q-1d

A suspension of quinine (3.6 g, 11.46 mmol), NaSEt (90% purity, 5 g, 5 eq.) in anhydrous DMF (60 mL) was heated at 105° C. (oil bath temperature) under N$_2$ for 16 hours. The mixture was cooled to room temperature then pored into sat. NH$_4$Cl aq. (100 mL) and pH of the aqueous phase was around 7. The mixture was extracted with ethyl acetate (2×200 mL). The combined organic phase was washed with aqueous HCl (2N, 4×25 mL) and the combined aqueous phase was treated with ammonium hydroxide (20 mL) and the pH of the aqueous phase is 10-11. The mixture was exacted with ethyl acetate (2×250 mL), and the combined organic phase was washed with brine, dried over anhydrous Na$_2$SO$_4$. The solvent was removed in vacuo and the residue was dissolved in anhydrous DMF (50 mL). At room temperature, TIPSCl (4.6 mL, 2 eq.) was added to the solution, followed by addition of imidazole (1.5 g, 2 eq.). The resulting solution was stirred at room temperature for 4 h, when TLC analysis indicated that the starting material was completely consumed. The reaction mixture was diluted with ethyl acetate (400 mL) and washed with sat. NaHCO$_3$ aq. (2×50 mL), brine and dried over anhydrous Na$_2$SO$_4$. The solvent was removed in vacuo and the crude product was purified by flash chromatography (ethyl acetate to ethyl acetate/MeOH/NH$_4$OH=20/2/0.5) to give Q-2 (4.7 g, 90% yield over 2 steps). $[\alpha]_D^{25}$=−77.2 (c 0.43, CHCl$_3$); $^1$H NMR (400 MHz, CDCl$_3$) δ 8.72 (d, J=4.0 Hz, 1H), 7.99 (d, J=6.8 Hz, 1H), 7.46 (d, J=2.0 Hz, 1H), 7.46 (s, 1H), 7.33 (dd, J=2.4 Hz, 9.2 Hz, 1H), 5.81-5.72 (m, 1H), 5.43 (d, J=4.8 Hz, 1H), 4.99-4.91 (m, 2H), 3.36-3.32 (m, 1H), 3.22-3.27 (m, 1H), 3.07 (dd, J=10.0 Hz, 1H), 2.68-2.63 (m, 2H), 2.25 (br, 1H), 1.79 (br, 1H), 1.72-1.66 (m, 2H), 1.56-1.43 (m, 2H), 1.36-1.25 (m, 3H), 1.11 (d, J=6.8 Hz, 18H); $^{13}$C NMR (100 MHz, DMSO-d6) δ 154.2, 147.65, 147.59, 144.1, 141.9, 131.4, 126.7, 124.9, 118.6, 114.2, 109.9, 72.6, 59.9, 57.0, 43.1, 40.0, 27.8, 27.7, 22.4, 17.9, 12.7; IR (CHCl$_3$) ν 3400-2400(br), 2943, 2866, 1616, 1506, 1457, 1258; HRMS (CI) m/z calcd. for (C$_{28}$H$_{42}$N$_2$O$_2$Si+H$^+$): 467.3094, found: 467.3106.

Figure 6:
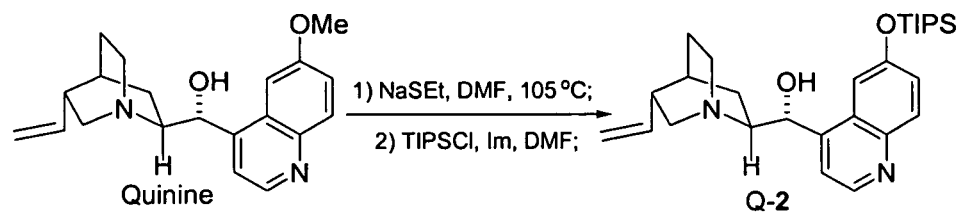
FIG. 6 depicts schematics for the preparation of catalyst Q-1d and catalyst QD-1d. For additional details, see the Exemplification, Examples 1 and 2.
Figure 6:
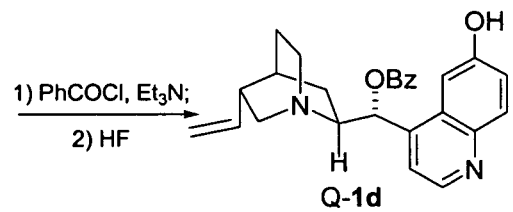
Figure 6:
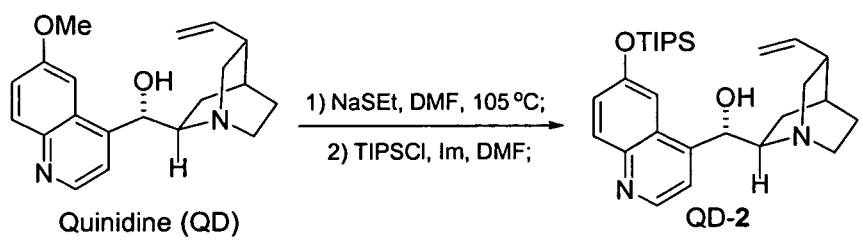
Figure 6:
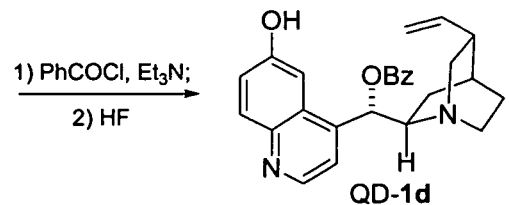
Figure 7:
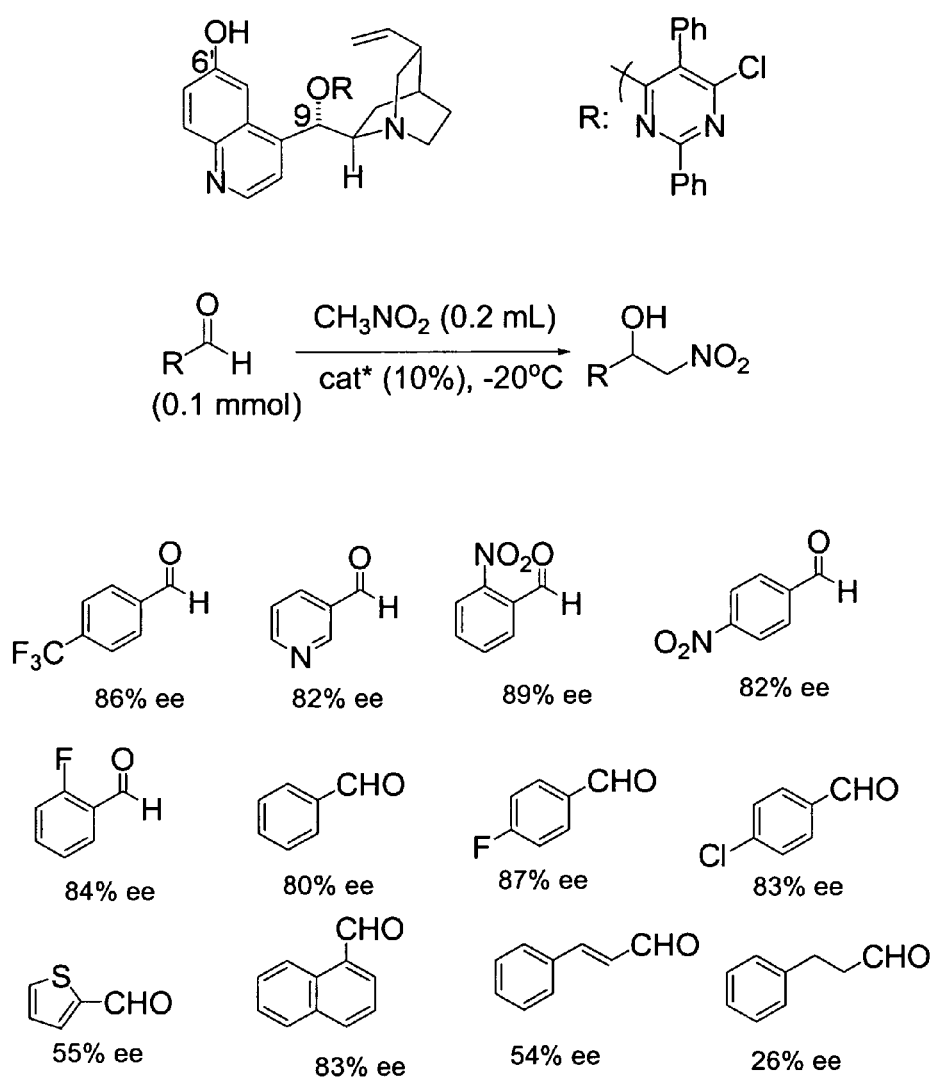
FIG. 7 depicts the results of bifunctional-cinchona-alkaloid-catalyzed enantioselective additions of nitromethane to aldehydes.
Figure 8:
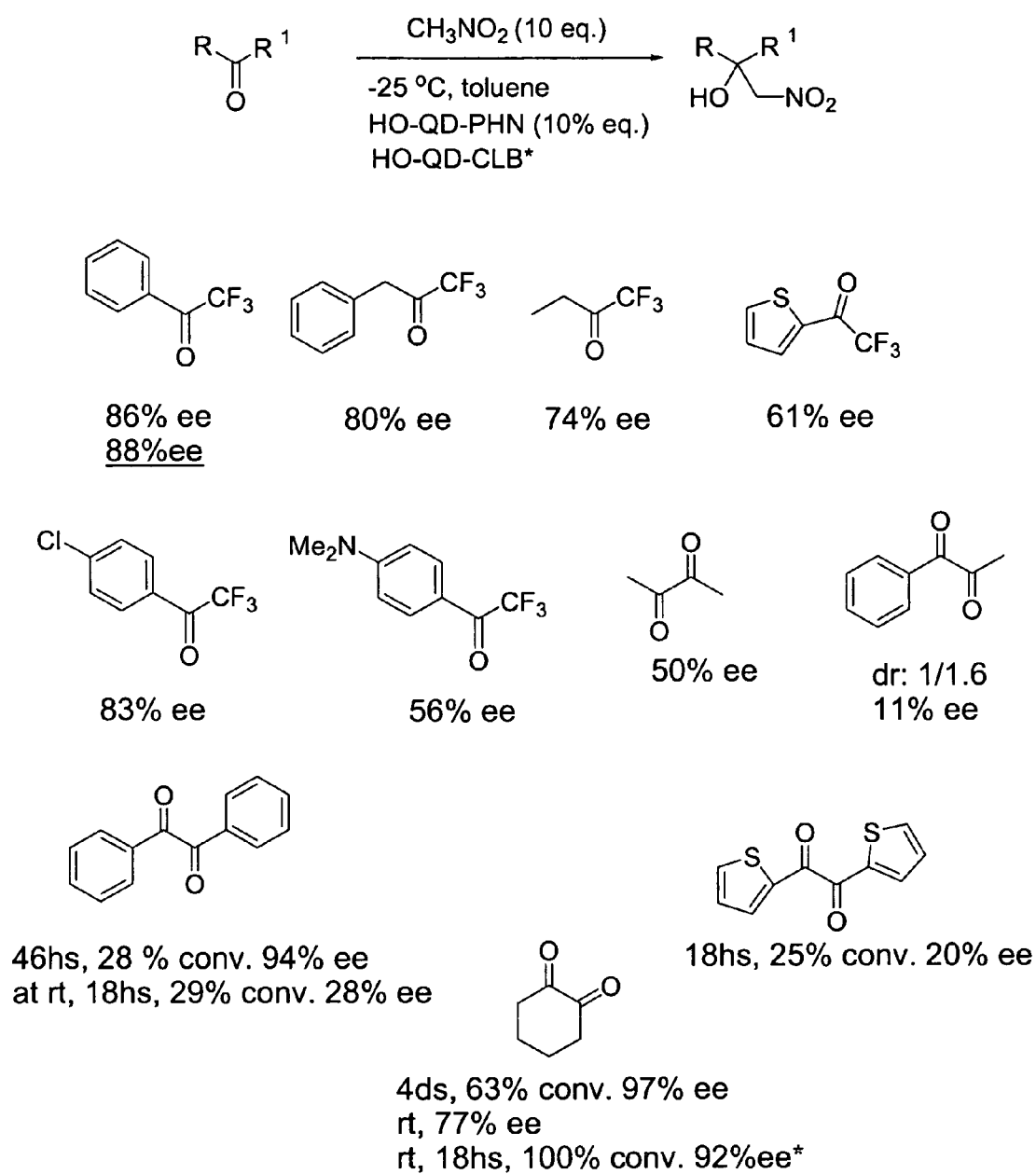
FIG. 8 depicts the results of bifunctional-cinchona-alkaloid-catalyzed enantioselective additions of nitromethane to trifluoromethyl ketones and alpha-diketones.
Figure 9:
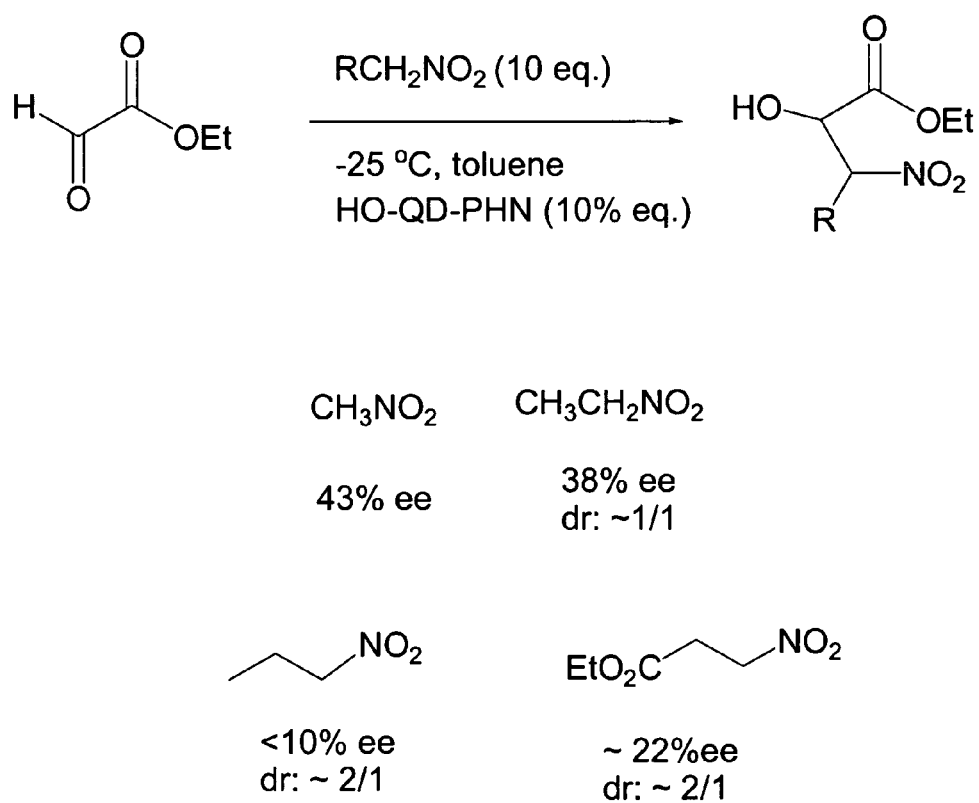
FIG. 9 depicts the results of bifunctional-cinchona-alkaloid-catalyzed enantioselective additions of nitromethane, nitroethane, nitropropane and ethyl 3-nitropropanoate to the aldehyde carbonyl moiety of ethyl glyoxalate.
Figure 10:
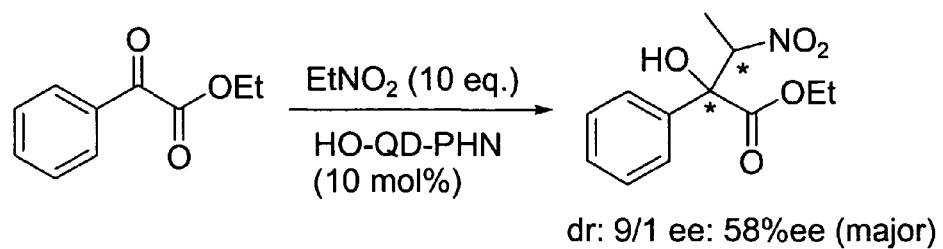
FIG. 10 depicts the results of the bifunctional-cinchona-alkaloid-catalyzed enantioselective addition of nitromethane to ethyl 2-oxo-2-phenylacetate; and the bifunctional-cinchona-alkaloid-catalyzed dynamic kinetic resolution of diethyl 2-oxo-3-methylsuccinate with nitromethane as the nucleophile.
Figure 10:
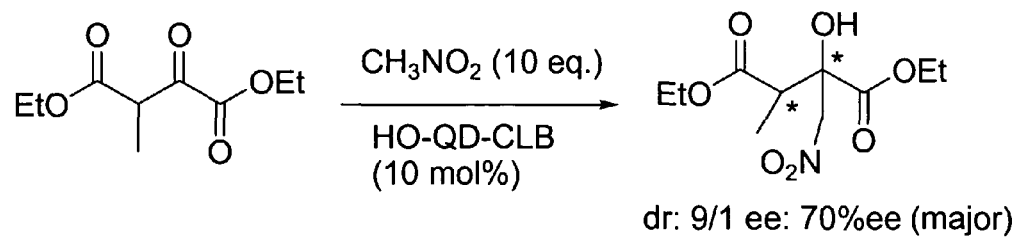

At room temperature to a solution of Q-2 (3.3 g, 7 mmol) in anhydrous CH$_2$Cl$_2$ (40 mL) was added PhCOCl (0.91 mL, 1.1 eq.) and Et$_3$N (1.97 mL, 2 eq.). The resulting mixture was stirred at room temperature for 3 hours and TLC analysis indicated that the starting material was completely consumed. The reaction mixture was diluted with CH$_2$Cl$_2$ (250 mL) and washed with sat. NaHCO$_3$, brine and dried over anhydrous Na$_2$SO$_4$. The solvent was removed in vacuo and the residue was dissolved in CH$_3$CN (50 mL). To the resulting solution, HF (48% aqueous solution, 2.5 mL) was added dropwise through syringe. After 15 minutes, TLC analysis showed that the starting material was completely consumed and the reaction mixture was diluted with ethyl acetate (400 mL), washed with sat. NaHCO$_3$ aq. (2×50 mL) and brine and dried over anhydrous Na$_2$SO$_4$. The solvent was removed in vacuo and the residue was purified by flash chromatography. (ethyl acetate/MeOH=20/1) to give Q-1d as a white powder (2.7 g, 73% yield over 2 steps). $[\alpha]_D^{25}$=+89.3 (c 0.45, CHCl$_3$); $^1$H NMR (400 MHz, DMSO-d6) δ 10.16 (br, 1H), 8.62 (d, J=4.4 Hz, 1H), 8.07 (d, J=8.0 Hz, 2H), 7.90 (d, J=8.4 Hz, 1H), 7.70 (t, J=7.2 Hz, 1H), 7.59-7.51 (m, 4H), 7.32 (d, J=9.2 Hz, 1H), 6.44 (d, J=7.6 Hz, 1H), 5.99-5.91 (m, 1H), 5.03 (d, J=18.4 Hz, 1H), 4.98 (d, J=11.6 Hz, 1H), 3.50-3.48 (m, 1H), 3.09 (br, 1H), 2.92-2.86 (m, 1H), 2.46-2.43 (m, 1H), 2.22 (br, 1H), 1.96-1.93 (m, 1H), 1.79 (br, 1H), 1.72-1.68 (m, 1H), 1.59-1.49 (m, 2H); $^{13}$C NMR (100 MHz, DMSO-d6) δ165.7, 156.4, 147.3, 144.0, 143.9, 142.9, 134.4, 132.0, 130.0, 129.9, 129.6, 127.6, 122.3, 119.6, 115.1, 105.2, 79.8, 75.3, 59.9, 56.6, 42.4, 27.9, 27.8, 25.3; IR (CHCl$_3$) ν 3500-2300 (br), 2943, 1717, 1540, 1558, 1507, 1268; HRMS (CI) m/z calcd for (C$_{26}$H$_{26}$N$_2$O$_3$+H$^+$): 415.2022, found: 415.2027. See FIG. 6A.

Example 2

Preparation of Catalyst QD-1d

Following same procedure as described for preparation of Q-2, QD-2 was obtained in 75% yield from quinidine (QD).

$[\alpha]_D^{25}$=+137.8 (c 1.0, CHCl$_3$); $^1$H NMR (400 MHz, CDCl$_3$) δ 8.71 (d, J=5.2 Hz, 1H), 7.87 (d, J=9.2 Hz, 1H), 7.65 (d, J=4.4 Hz, 1H), 7.37 (d, J=2.8 Hz, 1H), 7.20 (dd, J=2.4 Hz, 9.2 Hz, 1H), 6.50 (br, 1H), 6.02-5.93 (m, 1H), 5.22 (d, 3.6 Hz, 1H), 5.19 (d, J=10.4 Hz, 1H), 4.25 (br, 1H), 3.37-3.31 (m, 3H), 3.14-3.08 (m, 1H), 2.54-2.51 (m, 1H), 2.32 (t, J=12.0 Hz, 1H), 1.93-1.86 (m, 2H), 1.68-1.63 (m, 1H), 1.36 (hept. J=7.2 Hz, 3H), 1.13 (d, J=7.2 Hz, 9H), 1.11 (d, J=7.2 Hz, 9H); 1.00-0.90 (m, 1H); $^{13}$C NMR (100 MHz, DMSO-d6) δ 154.4, 147.8, 144.1, 143.7, 136.6, 131.3, 125.6, 124.7, 119.0, 117.3, 110.0, 67.3, 60.2, 49.2, 48.7, 37.6, 27.7, 23.6, 18.5, 18.05, 18.01, 12.8; IR (CHCl$_3$) ν 3217 (br), 2943, 2867, 1617, 1589, 1504, 1456, 1259; HRMS (CI) m/z calcd. for (C$_{28}$H$_{42}$N$_2$O$_2$Si+H$^+$): 467.3094, found: 467.3103.

Following the same procedure described above for the preparation of Q-1d, QD-1d was prepared in 87% yield from QD-2. $[\alpha]_D^{25}$=−10 (c 0.31, CHCl$_3$); $^1$H NMR (400 MHz, CDCl$_3$) δ 9.61 (br, 1H), 8.65 (d, J=4.4 Hz, 1H), 8.04 (d, J=7.6 Hz, 2H), 7.92 (d, J=9.6 Hz, 1H), 7.69 (s, 1H), 7.54 (t, J=6.8 Hz, 1H), 7.42-7.40 (m, 3H), 7.20 (d, J=9.2 Hz, 1H), 6.75 (d, J=5.6 Hz, 1H), 6.02-5.93 (m, 1H), 5.08 (d, J=6.4 Hz, 1H), 5.05 (d, J=17.2 Hz, 1H), 3.39 (dd, J=8.4 Hz, 6.4 Hz, 1H), 3.10-3.05 (m, 1H), 3.01-2.95 (m, 1H), 2.84-2.79 (m, 1H), 2.73-2.65 (m, 1), 2.27 (dd, J=7.6 Hz, 8.0 Hz, 1H), 2.01 (t, J=9.6 Hz, 1H), 1.83 (s, 1H), 1.50-1.48 (m, 3H]; $^{13}$C NMR (100 MHz, CDCl$_3$) δ 165.2, 156.4, 146.1, 143.6, 143.4, 139.8, 133.3, 131.0, 129.7, 129.6, 128.5, 127.3, 122.8, 118.6, 115.1, 105.8, 74.3, 58.8, 49.6, 49.1, 39.2, 27.5, 26.0. 23.0; IR (CHCl$_3$) ν 2500-3500 (br), 3071, 2940, 1723, 1618, 1469, 1452, 1269, 1107; HRMS (ESI) m/z calcd for (C$_{26}$H$_{26}$N$_2$O$_3$+H$^+$): 415.2022, found: 415.2026. See FIG. 6B.

Example 3

Enantioselective Addition of Nitromethane to α-Keto esters (via QD-1d or Q-1d)

At −20° C., to a solution of α-keto ester 2 (0.5 mmol), nitromethane (5 mmol) in CH$_2$Cl$_2$ (0.5 mL) was added catalyst QD-1d or Q-1d (5 mol %). See FIG. 3. The resulting mixture was kept at the indicated temperature until 2 is completely consumed. The reaction mixture was directly subjected to silica gel flash chromatography using the eluent specified below to afford the desired product in the yields and enantiomeric excess summarized above. The catalyst is recovered in greater than 95% yield by washing the silica gel column with MeOH. The recovered catalyst was identical to that before the reaction by NMR analysis and can be reused without further treatment.

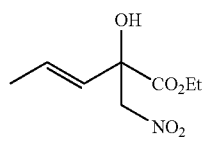

3a (+)-3a: This product was obtained as a colorless oil in 92% yield after flash chromatography (elution gradient: ethyl acetate/hexane=1/15) and 96% ee as determined by HPLC analysis [Daicel chiralpak AD, hexanes:IPA, 90:10, 0.8 mL/min, λ 215 nm, t (major)=10.03 min, t (minor)=10.91 min] from a reaction catalyzed by QD-1d (5 mol %) at −20° C. for 14 hours. $[\alpha]_D^{25}$=+56.0 (c 0.93, CHCl$_3$); $^1$H NMR (400 MHz, CDCl$_3$) δ 6.13 (dq, J=15.2 Hz, 6.8 Hz, 1H), 5.45 (dq, J=15.2 Hz, 1.6 Hz, 1H), 4.86 (d, J=14.0 Hz, 1H), 4.48 (d, J=14.0 Hz, 1H), 4.42-4.28 (m, 2H), 3.77 (s, 1H), 1.75 (dd, J=1.2 Hz, 14.0 Hz, 3H), 1.34 (t, J=6.8 Hz, 3H); $^{13}$C NMR (100 MHz, CDCl$_3$) δ 171.8, 130.6, 125.7, 79.9, 75.0, 63.2, 17.6, 13.9; these data is in agreement with those reported in literature. Christensen, C.; Juhl, K.; Jørgensen, K. A.; Chem. Commun. 2001, 2222-2223; and Christensen, C.; Juhl, K.; Hazell, R. G.; Jørgensen, K. A. J. Org. Chem. 2002, 67, 4875-4881. (−)-3a: This product was obtained as a colorless oil in 92% yield and 97% ee from a reaction catalyzed by Q-1d (5.0 mol %) at −20° C. for 15 hours.

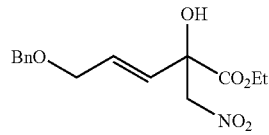

3b (+)-3b: This product was obtained as a colorless oil in 98% yield after flash chromatography (elution gradient: diethyl ether) and 94% ee as determined by HPLC analysis [Daicel chiralpak AD, hexanes:IPA, 90:10, 0.8 mL/min, λ 215 nm, t (major)=17.65 min, t (minor)=19.99 min] from a reaction catalyzed byQD-1d (5 mol %) at −20° C. for 24 hours. $[\alpha]_D^{25}$=+29.8 (c 1.22, CHCl$_3$); $^1$H NMR (400 MHz, CDCl$_3$) δ 7.36-7.32 (m, 5H), 6.25 (dt, J=15.2 Hz, 4.8 Hz, 1H), 5.76 (dt, J=15.2 Hz, 1.6 Hz, 1H), 4.88 (dd, J=14.0 Hz, 1.2 Hz, 1H), 4.53 (s, 2H), 4.48 (d, J=13.2 Hz, 1H), 4.41-4.29 (m, 2H), 4.08-4.06 (m, 2H), 3.84 (s, 1H), 1.34 (t, J=7.2 Hz, 3H); $^{13}$C NMR (100 MHz, CDCl$_3$) δ171.4, 137.7, 131.5, 128.3, 127.7, 127.6, 125.8, 79.7, 75.1, 72.6, 68.9, 63.3, 13.9; IR (CHCl$_3$) ν 3489 (br), 3031, 2983, 2859, 1742, 1560, 1453, 1378, 1220; HRMS (ESI) m/z calcd for (C$_{15}$H$_{19}$NO$_6$+Na$^+$): 332.1110, found: 332.1102. (−)-3b: This product was obtained as a colorless oil in 99% yield and 95% ee from a reaction catalyzed by Q-1d (5 mol %) at −20° C. for 24 hours.

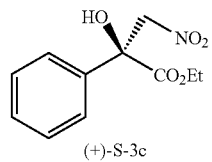

(+)-S-3c (+)-S-3c: This product was obtained as a colorless oil in 96% yield after flash chromatography (elution gradient: ethyl acetate/hexane=1/19) and 95 as determined by HPLC analysis [Daicel chiralcel OD, hexanes:IPA, 80:20, 1.0 mL/min, λ 220 nm, t (major)=7.49 min, t (minor)=9.46 min] from a reaction catalyzed by QD-1d (5 mol %) at −20° C. for 35 hours. $[\alpha]_D^{25}$=+28.4 (c 1.05, CHCl$_3$); $^1$H NMR (400 MHz, CDCl$_3$) δ 7.62-7.60 (m, 2H), 7.43-7.40 (m, 3H), 5.26 (d, J=14.0 Hz, 1H), 4.68 (d, J=14.0 Hz, 1H), 4.44-4.31 (m, 2H), 4.22 (s, 1H), 1.34 (dt, J=1.2 Hz, 7.2 Hz, 3H); $^{13}$C NMR (100 MHz, CDCl$_3$) δ 171.6, 136.4, 129.0, 128.8, 125.2, 80.7, 75.9, 63.5, 13.8; these data are in agreement with those reported in the literature. Christensen, C.; Juhl, K.; Jørgensen, K. A.; Chem. Commun. 2001, 2222-2223; and Christensen, C.; Juhl, K.; Hazell, R. G.; Jørgensen, K. A. J. Org Chem. 2002, 67, 4875-4881. The absolute configuration of (+)-3c was determined to be S by converting 3c into β-lactam 5c and comparing the value of the specific rotation of 5c with that reported in the literature. (For further details see below preparation of β-lactam 5c below). (−)-R-3c: This product was obtained as a colorless oil in 96% yield and 93% ee from a reaction catalyzed by Q-1d (5 mol %) at −20° C. for 46 hours.

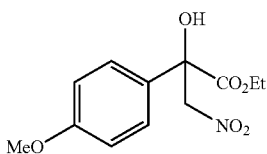

3d (+)-3d: This product was obtained as a white solid in 86% yield after flash chromatography (elution gradient: ethyl acetate/hexane=1/10) and 94% ee as determined by HPLC analysis [Daicel chiralpak AS, hexanes:IPA, 80:20, 1.0 mL/min, λ 220 nm, t (major)=10.90 min, t (minor)=13.49 min] from a reaction catalyzed by QD-1d (5 mol %) at −20° C. for 96 hours. $[\alpha]_D^{25}$=+26.9 (c 1.25, CHCl$_3$); $^1$H NMR (400 MHz, CDCl$_3$) δ7.51 (d, J=8.8 Hz, 2H), 6.91 (d, J=8.8 Hz, 2H), 5.22 (d, J=14.4 Hz, 1H), 4.65 (d, J=14.4 Hz, 1H), 4.17 (s, 1H), 3.82 (s, 3H), 1.34 (t, J=6.8 Hz, 3H); $^{13}$C NMR (100 MHz, CDCl$_3$) δ 171.8, 160.1, 128.3, 126.6, 114.2, 80.8, 75.7, 63.5, 55.3, 13.9; these data are in agreement with those reported in the literature. Christensen, C.; Juhl, K.; Jørgensen, K. A.; *Chem. Commun.* 2001, 2222-2223; and Christensen, C.; Juhl, K.; Hazell, R. G.; Jørgensen, K. A. *J. Org. Chem.* 2002, 67, 4875-4881. (−)-3d: This product was obtained as a colorless oil in 84% yield and 97% ee from a reaction catalyzed by Q-1d (5 mol %) at −20° C. for 96 hours.

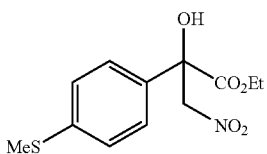

3e (+)-3e: This product was obtained as a white solid in 86% yield after flash chromatography (elution gradient: ethyl acetate/hexane=1/7) and 96% ee as determined by HPLC analysis [Daicel chiralcel OD, hexanes:IPA, 80:20, 1.0 mL/min, λ 220 nm, t (major)=8.84 min, t (minor)=12.15 min] from a reaction catalyzed by QD-1d (5.0 mol %) at −20° C. for 72 hours. $[\alpha]_D^{25}$=+29.7 (c 1.1, CHCl$_3$); $^1$H NMR (400 MHz, CDCl$_3$) δ7.51 (dd, J=2.0 Hz, 6.8 Hz, 2H), 7.25 (d, J=6.8 Hz, 2H), 5.22 (d, J=14.4 Hz, 1H), 4.65 (d, J=14.4 Hz, 1H), 4.43-4.30 (m, 2H), 4.19 (s, 1H), 2.49 (s, 3H), 1.34 (t, J=7.2 Hz, 3H); $^{13}$C NMR (100 MHz, CDCl$_3$) δ171.5, 140.2, 132.8, 126.2, 126.6, 80.6, 75.7, 63.6, 15.3, 13.9; IR (CHCl$_3$) ν 3484, 2984, 2924, 1736, 1559, 1493, 1378, 1226; HRMS (ESI) m/z calcd for (C$_{12}$H$_{15}$NO$_5$S+Na$^+$): 308.0569, found: 308.0571. (−)-3e This product was obtained as a colorless oil in 86% yield and 96% ee from a reaction catalyzed by Q-1d (5 mol %) at −20° C. for 72 hours.

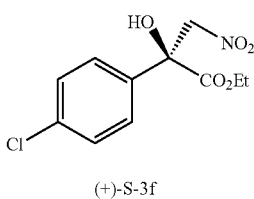

(+)-S-3f (+)-S-3f: This product was obtained as a colorless oil in 98% yield after flash chromatography (elution gradient: ethyl acetate/hexane=1/15) and 97% ee as determined by HPLC analysis [Daicel chiralcel OD, hexanes:IPA, 85:15, 1.0 mL/min, λ 220 nm, t (major)=7.67 min, t (minor)=9.17 min] from a reaction catalyzed by QD-1d (5 mol %) at −20° C. for 12 hours. $[\alpha]_D^{25}$=+24.4 (c 1.1, CHCl$_3$); $^1$H NMR (400 MHz, CDCl$_3$) δ 7.56 (td, J=2.4 Hz, 8.8 Hz, 2H), 7.39 (td, J=2.4 Hz, 8.8 Hz, 2H), 5.22 (d, J=14.0 Hz, 1H), 4.64 (d, J=14.0 Hz, 1H), 4.44-4.31 (m, 2H), 4.24 (s, 1H), 1.34 (t, J=7.2 Hz, 3H); $^{13}$C NMR (100 MHz, CDCl$_3$) δ171.2, 135.2, 134.9, 129.0, 126.7, 80.5, 75.6, 63.7, 13.8; these data are in agreement with those reported in the literature. Christensen, C.; Juhl, K.; Jørgensen, K. A.; *Chem. Commun.* 2001, 2222-2223; and Christensen, C.; Juhl, K.; Hazell, R. G.; Jørgensen, K. A. *J. Org. Chem.* 2002, 67, 4875-4881. The absolute configuration of (+)-3f was determined to be S by comparing the specific rotation with that of literature data. $[\alpha]_D^{25}$=+21.7 (c 1.0, CH$_2$Cl$_2$) for 96% ee [lit. $[\alpha]_D^{23}$=−17.5 (c 1.02, CH$_2$Cl$_2$) 88% ee for R isomer; Christensen, C.; Juhl, K.; Jørgensen, K. A.; *Chem. Commun.* 2001, 2222-2223; and Christensen, C.; Juhl, K.; Hazell, R. G.; Jørgensen, K. A. *J. Org. Chem.* 2002, 67, 4875-4881]. (−)-R-3f: This product was obtained as a colorless oil in 96% yield and 96% ee from a reaction catalyzed by Q-1d (5 mol %) at −20° C. for 12 hours.

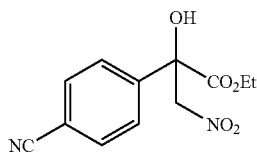

3g (+)-3g: This product was obtained as a white solid in 96% yield after flash chromatography (elution gradient: ethyl acetate/hexane=1/6) and 94% ee as determined by HPLC analysis [Daicel chiralpak AD, hexanes:IPA, 80:20, 0.9 mL/min, λ 220 nm, t(major)=15.44 min, t (minor)=13.99 min] from a reaction catalyzed by QD-1d (5 mol %) at −20° C. for 9 hours. $[\alpha]_D^{25}$=+24.9 (c 1.05, CHCl$_3$); $^1$H NMR (400 MHz, CDCl$_3$) δ 7.78 (d, J=8.4 Hz, 2H), 7.72 (d, J=8.4 Hz, 2H), 5.23 (d, J=14.0 Hz, 1H), 4.65 (d, J=14.0 Hz, 1H), 4.47-4.33 (m, 2H), 4.32 (s, 1H), 1.36 (t, J=7.2 Hz, 3H); $^{13}$C NMR (100 MHz, CDCl$_3$) δ 170.6, 141.3, 132.6, 126.3, 118.0, 113.3, 80.3, 75.7, 64.2, 13.9; IR (CHCl$_3$) ν 3475 (br), 2985, 2232, 1741, 1561, 1502, 1378, 1229; HRMS (CI) m/z calcd for (C$_{12}$H$_{12}$N$_2$O$_5$+H$^+$): 265.0824, found: 265.0831. (−)-3g This product was obtained as a colorless oil in 98% yield and 97% ee from a reaction catalyzed by Q-1d (5 mol %) at −20° C. for 11 hours.

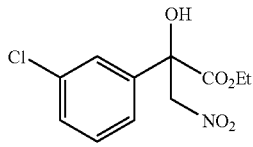

3h (+)-3h: This product was obtained as a colorless oil in 91% yield after flash chromatography (elution gradient: ethyl acetate/hexane=1/15) and 95% ee as determined by HPLC analysis [Daicel chiralcel OD, hexanes:IPA, 85/15, 1.0 mL/min, λ 220 nm, t (major)=7.86 min, t (minor)=10.15 min] from a reaction catalyzed by QD-1d (5 mol %) at −20° C. for 11 hours. $[\alpha]_D^{25}$=+25.2 (c 1.1, CHCl$_3$); $^1$H NMR (400 MHz, CDCl₃) δ 7.64 (d, J=1.6 Hz, 1H), 7.51-7.47 (m, 1H), 7.38-7.32 (m, 2H), 5.22 (d, J=14.8 Hz, 1H), 4.65 (d, J=14.8 Hz, 1H), 4.46-4.33 (m, 2H), 4.25 (s, 1H), 1.36 (t, J=7.2 Hz, 3H); ¹³C NMR (100 MHz, CDCl₃) δ 171.1, 138.3, 135.0, 130.1, 129.3, 125.7, 123.4, 80.5, 75.6, 63.9, 13.9; IR (CHCl₃) v 3486 (br), 3073, 2984, 2926, 1739, 1562, 1475, 1416, 1377, 1227; HRMS (ESI) m/z calcd for (C₁₁H₁₂ClNO₅+Na⁺): 296.0302, found: 296.0300. (−)-3h: This product was obtained as a colorless oil in 96% yield and 95% ee from a reaction catalyzed by Q-1d (5 mol %) at −20° C. for 11 hours.

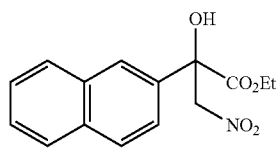

3i (+)-3i: This product was obtained as a white solid in 96% yield after flash chromatography (elution gradient: ethyl acetate/hexane=1/19) and 94% ee as determined by HPLC analysis [Daicel chiralcel OD, hexanes:IPA, 60:40, 1.0 mL/min, λ 280 nm, t(major)=7.60 min, t(minor)=19.91 min] from a reaction catalyzed by QD-1d (5 mol %) at −20° C. for 60 hours. [α]$_D^{25}$=+47.6 (c 1.1, CHCl₃); ¹H NMR (400 MHz, CDCl₃) δ 8.12 (s, 1H), 7.89-7.84 (m, 3H), 7.67 (dd, J=2.0 Hz, 8.8 Hz, 1H), 7.56-7.52 (m, 2H), 5.39 (d, J=14.0 Hz, 1H), 4.76 (d, J=14.0 Hz, 1H), 4.46-4.33 (m, 2H), 4.34 (s, 1H), 1.36 (t, J=7.2 Hz, 3H); ¹³C NMR (100 MHz, CDCl₃) δ171.6, 133.6, 133.2, 132.9, 128.7, 128.4, 127.5, 127.0, 126.7, 125.0, 122.3, 80.7, 76.2, 63.6, 13.9; IR (CHCl₃) v 3487 (br), 3059, 2983, 1738, 1560, 1415, 1377, 1270, 1224, 1133; HRMS (CI) m/z calcd for (C₁₅H₁₅NO₅⁺): 289.0950, found: 289.0942. (−)-3i: This product was obtained as a colorless oil in 97% yield and 94% ee from a reaction catalyzed by Q-1d (5.0 mol %) at −20° C. for 60 hours.

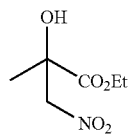

3j (−)-3j: This product was obtained as a colorless oil in 89% yield after flash chromatography (elution gradient: ethyl acetate/hexane=1/6) and 95% ee as determined by HPLC analysis [Daicel chiralpak AS, hexanes:IPA, 95:5, 1.0 mL/min, λ 215 nm, t (major)=16.90 min, t (minor)=19.93 min] from a reaction catalyzed by QD-1d (5 mol %) at −20° C. for 12 hours. [α]$_D^{25}$=−5.1 (c 1.0, CHCl₃); ¹H NMR (400 MHz, CDCl₃) δ 4.84 (d, J=14.0 Hz, 1H), 4.56 (d, J=14.0 Hz, 1H), 4.40-4.28 (m, 2H), 3.73 (s, 1H), 1.46 (s, 3H), 1.34 (t, J=7.2 Hz, 3H); ¹³C NMR (100 MHz, CDCl₃) δ173.5, 80.9, 72.4, 63.0, 23.8, 13.9; these data are in agreement with those reported in the literature. Christensen, C.; Juhl, K.; Jørgensen, K. A.; Chem. Commun. 2001, 2222-2223; and Christensen, C.; Juhl, K.; Hazell, R. G.; Jørgensen, K. A. J. Org. Chem. 2002, 67, 4875-4881. (+)-3j: This product was obtained as a colorless oil in 90% yield and 95% ee from a reaction catalyzed by Q-1d (5 mol %) at −20° C. for 12 hours.

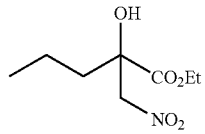

3k (−)-3k: This product was obtained as a colorless oil in 90% yield after flash chromatography (elution gradient: ethyl acetate/hexane=1/15) and 95% ee as determined by HPLC analysis [Daicel chiralpak AS, hexanes:IPA, 90:10, 1.0 mL/min, λ 215 nm, t (major)=7.40 min, t (minor)=9.09 min] from a reaction catalyzed by QD-1d (5.0 mol %) at −20° C. for 17 hours. [α]$_D^{25}$=−14.0 (c 1.15, CHCl₃); ¹H NMR (400 MHz, CDCl₃) δ 4.82 (d, J=13.2 Hz, 1H), 4.56 (d, J=13.2 Hz, 1H), 4.41-4.29 (m, 2H), 3.70 (s, 1H), 1.72-1.59 (m, 2H), 1.57-1.45 (m, 1H), 1.34 (t, J=7.2 Hz, 3H), 1.26-1.14 (m, 1H), 0.93 (t, J=7.2 Hz, 3H); ¹³C NMR (100 MHz, CDCl₃) δ 172.9, 80.8, 75.2, 62.9, 38.6, 16.0, 14.0, 13.8; IR (CHCl₃) v 3505 (br), 2967, 2937, 1739, 1561, 1467, 1380, 1234, 1162; HRMS (CI) m/z calcd for (C₈H₁₅NO₅+H⁺): 206.1028, found: 206.1023.

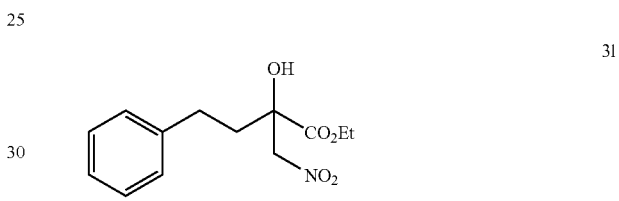

3l (−)-3l: This product was obtained as a colorless oil in 88% yield after flash chromatography (elution gradient: ethyl acetate/hexane=1/15) and 95% ee as determined by HPLC analysis [Daicel chiralpak AS, hexanes:IPA, 90:10, 1.0 mL/min, λ 220 nm, t (major)=10.75 min, t (minor)=14.79 min] from a reaction catalyzed by QD-1d (5 mol %) at −20° C. for 14 hours. [α]$_D^{25}$=−18.8 (c 1.5, CHCl₃); ¹H NMR (400 MHz, CDCl₃) δ 7.31-7.14 (m, 5H), 4.83 (d, J=13.2 Hz, 1H), 4.58 (d, J=13.2 Hz, 1H), 4.39-4.25 (m, 2H), 3.82 (s, 1H), 2.86-2.79 (m, 1H), 2.53-2.45 (m, 1H), 2.06-1.92 (m, 2H), 1.34 (t, J=7.2 Hz, 3H); ¹³C NMR (100 MHz, CDCl₃) δ 172.6, 140.1, 128.5, 128.2, 126.2, 80.7, 74.9, 63.0, 38.1, 28.9, 14.0; these data are in agreement with those reported in the literature. Christensen, C.; Juhl, K.; Jørgensen, K. A.; Chem. Commun. 2001, 2222-2223; and Christensen, C.; Juhl, K.; Hazell, R. G.; Jørgensen, K. A. J. Org. Chem. 2002, 67, 4875-4881. (+)-3l: This product was obtained as a colorless oil in 89% yield and 94% ee from a reaction catalyzed by Q-1d (5.0 mol %) at −20° C. for 11 hours.

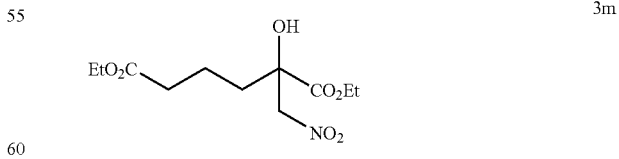

3m (−)-3m: This product was obtained as a colorless oil in 87% yield after flash chromatography (elution gradient: ethyl acetate/hexane=1/5) and 94% ee as determined by HPLC analysis [Daicel chiralcel OJ, hexanes:IPA, 70:30, 1.0 mL/min, λ 215 nm, t (major)=17.23 min, t (minor)=12.00 min] from a reaction catalyzed by QD-1d (5 mol %) at −20°

C. for 15 hours. $[\alpha]_D^{25}=-5.3$ (c 1.15, CHCl$_3$); $^1$H NMR (400 MHz, CDCl$_3$) δ 4.82 (d, J=14.0 Hz, 1H), 4.57 (d, J=14.0 Hz, 1H), 4.43-4.30 (m, 2H), 4.13 (q, J=7.2 Hz, 2H), 3.75 (s, 1H), 2.37-2.26 (m, 2H), 1.86-1.73 (m, 2H), 1.70-1.64 (m, 1H), 1.59-1.49 (m, 1H), 1.35 (t, J=6.8 Hz, 3H), 1.25 (t, J=7.2 Hz, 3H); $^{13}$C NMR (100 MHz, CDCl$_3$) δ172.7, 172.6, 80.7, 75.0, 63.1, 60.4, 35.6, 33.5, 18.2, 14.1, 14.0; IR (CHCl$_3$) ν 3492 (br), 2983, 2939, 1733, 1560, 1419, 1379, 1224; HRMS (ESI) m/z calcd for (C$_{11}$H$_{19}$NO$_7$+Na$^+$): 300.1059, found: 300.1053. (+)-3m: This product was obtained as a colorless oil in 86% yield and 93% ee from a reaction catalyzed by Q-1d (5 mol %) at −20° C. for 11 hours.

Example 4

Synthesis of 3-phenyl-3-hydroxyazetidin-2-one 5c

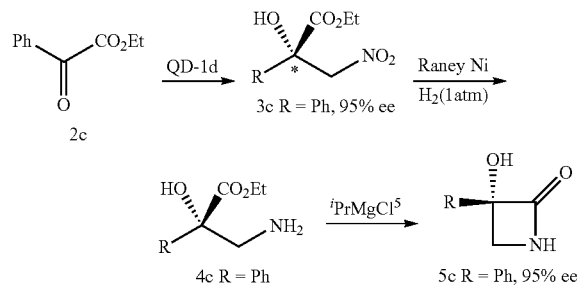

See Christensen, C.; Juhl, K.; Jørgensen, K. A.; *Chem. Commun.* 2001, 2222-2223; Christensen, C.; Juhl, K.; Hazell, R. G.; Jørgensen, K. A. *J. Org. Chem.* 2002, 67, 4875-4881; and Nicewicz, D. A.; Yates, C. M.; Johnson, J. S. *J. Org. Chem.* 2004, 69, 6548-6555.

At −20° C., to a solution of α-keto ester 2c (1.136 g, 6.38 mmol), nitromethane (3.4 mL) in CH$_2$Cl$_2$ (6.4 mL) was added catalyst QD-1d (132 mg, 5.0 mol %) The resulting mixture was kept at −20° C. for 40 hours when TLC showed 2c was completely consumed. The reaction mixture was directly subjected to silica gel flash chromatography (EA/Hexanes=1/15) to furnish 3c as a clear oil (1.503 g, 98% yield) and in 95% ee. The column was washed with MeOH and the catalyst 1d was recovered almost quantitatively (>131 mg). The recovered catalyst was shown to be identical to that before the reaction by NMR analysis.

To a solution of 3c (1.04 g, 4.35 mmol) obtained from reactions using QD-1d in EtOH (25 mL) was added Raney nickel (1.0 g in 10 mL). The resulting reaction mixture was stirred under H$_2$ at atmospheric pressure for 4 h at room temperature. After the starting material was completely consumed (monitored by TLC), the reaction mixture was passed through a short pad of celite and the celite was then washed with EtOH (2×10 mL). The filtrate was concentrated in vacuo and the residue 4c was used in next step without further purification (864 mg, 95% yield).

At 0° C., to a solution of 4c (113 mg, 0.54 mmol) in anhydrous THF (2.0 mL) was added $^i$PrMgCl (2.0 M in THF, 1.35 mL, 2.7 mmol) dropwisely via a synringe. The resulting reaction mixture was stirred at room temperature for 19 hours. The reaction was quenched with NH$_4$Cl aq. (sat. 10.0 mL) and extracted with ethyl acetate (50 mL). The organic phase was washed with brine and dried over anhydrous Na$_2$SO$_4$. The solvent was removed in vacuo and the residue was purified by flash chromatography (ethyl acetate:hexanes=1.5:1) to give 5c as a white powder (36 mg, 37% yield over 3 steps from 2c). The ee of 5c was determined to be 95% by HPLC analysis (chiralcel OD, IPA/Hexane=95/5, 1.0 mL/min, 220 nm, t(major)=32.27 min, t(minor)=28.73 min). $[\alpha]_D^{25}=107°$ (c: 0.27 in CHCl$_3$) {lit.$^5$ $[\alpha]_D^{23}=-57.4°$, (c: 0.25 in CHCl$_3$) for 80% ee, S isomer}. The absolute configuration of 5c is therefore determined to be S, which indicate that the absolute configuration of 3c obtained with QD-1d is S. $^1$H NMR (400 MHz, CDCl$_3$) δ 7.48-7.45 (m, 2H), 7.36-7.26 (m, 3H), 6.89 (br, 1H), 3.56 (d, J=5.6 Hz, 1H), 3.47 (d, J=5.6 Hz, 1H); $^{13}$C NMR (100 MHz, CDCl$_3$) δ 171.9, 138.0, 128.6, 128.4, 125.3, 86.9, 54.1. The data is consistent with those reported in the literature.

Example 5

Synthesis of Azide 6c

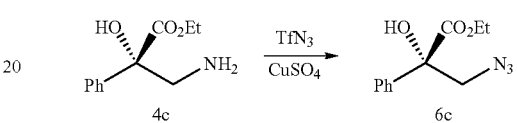

See Liu, Q.; Tor, Y. *Org. Lett.* 2003, 5, 2571-2572; and Nyffeler, P. T.; Liang, C.-H.; Koeller, K. M.; Wong, C.-H *J. Am. Chem. Soc.* 2002, 124, 10773-10778.

A mixture of NaN$_3$ (1.76 g, 27 mmol), water (4 mL) and CH$_2$Cl$_2$ (2 mL) was cooled to 0° C. in an ice-water bath. To this mixture under vigorous stirring, Tf$_2$O (0.75 mL, 4.5 mmol) was added dropwise via a syringe. The resulting mixture was stirred at 0° C. for 3 h and 1 mL of water was added to the reaction mixture, after which the aqueous and organic phase was separated. The organic phase was collected, and the aqueous phase was extracted with CH$_2$Cl$_2$ (2 mL). The combined organic phase was washed with sat. aqueous NaHCO$_3$ (5 mL), after which it was used for the reaction with 4c.

At room temperature, to a solution of crude 4c (341 mg, 1.6 mmol, derived from hydrogenation of 3c as described above) in CH$_2$Cl$_2$ (1.5 mL) was added Et$_3$N (0.63 mL, 4.8 mmol) and an aqueous solution of CUSO$_4$ (12 mg in 0.25 mL of water) consecutively. To the resulting mixture, a solution of TfN$_3$ in CH$_2$Cl$_2$ freshly prepared as described above was added. This is followed by the addition of MeOH (around 1 mL), and the reaction mixture became homogenous. The reaction mixture was stirred at room temperature for 2.5 hours, afterwhich it was poured into sat. NaHCO$_3$ aq. (20 mL). The resulting mixture was extracted with CH$_2$Cl$_2$ (2×40 mL). The combined organic phase was washed with brine and dried over anhydrous Na$_2$SO$_4$. The solvent was removed in vacuo and the residue was purified by chromatography (silica gel, ethyl acetate/hexanes=1/20) to give 6c as a clear oil (339 mg, 88% yield, 84% yield over 2 steps from 3c). The ee of 6c was determined to be 96% by HPLC analysis (chiralcel OJ, IPA/Hexanes=90/10, 1.0 mL/min, 220 nm, t(minor)=10.03 min, t(major)=13.17 min). $[\alpha]_D^{25}=30°$ (c: 1.1 in CHCl$_3$), $^1$H NMR (400 MHz, CDCl$_3$) δ 7.60 (d, J=6.8 Hz, 2H), 7.40-7.32 (m, 3H), 4.39-4.25 (m, 2H), 4.01 (s, 1H), 3.84 (d, J=12.4 Hz, 1H), 3.62 (d, J=12.4 Hz, 1H), 1.33 (t, J=7.2 Hz, 3H); $^{13}$C NMR (100 MHz, CDCl$_3$) δ 172.8, 138.3, 128.5, 125.3, 79.3, 63.1, 58.4, 14.0; IR (CHCl$_3$) ν 3496, 3063, 2984, 2102, 1732, 1448, 1250; HRMS (ESI) m/z calcd for (C$_{11}$H$_{13}$N3O$_3$+Na$^+$): 258.0855, found: 258.0860.

Example 6

Synthesis of Aziridine 7c

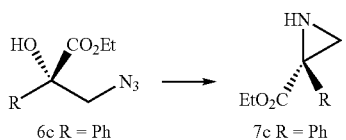

See Shao, H.; Zhu, Q.; Goodman, M. *J. Org. Chem.* 1995, 60, 790-791.

To a solution of 6c (300 mg, 1.27 mmol) in anhydrous $CH_3CN$ (8.0 mL) was added $PPh_3$ (501 mg, 1.9 mmol) at room temperature. The mixture was stirred at room temperature for 1.0 h and then refluxed for 14 h under Ar atmosphere. The solvent was removed in vacuo and the residue was purified by chromatography (ethyl acetate/hexanes=1/15) to give 7c as a clear oil (196 mg, 80% yield). The ee of 7c was determined to be 91% ee by HPLC (chiralpak AS plus R,R-Whelko, IPA/Hexanes=90/10, 1.0 mL/min, 220 nm, t(major)=11.20 min, t(minor)=12.59 min). $[\alpha]_D^{25}$=7.4 (c: 1.0 in $CHCl_3$); $^1$H NMR (400 MHz, $CDCl_3$) δ 7.49-7.44 (m, 2H), 7.35-7.27 (m, 3H), 4.26-4.12 (m, 2H), 2.51 (dd, J=2.0 Hz, 10.4 Hz, 1H), 2.00-1.91 (m, 2H), 1.22 (t, J=7.2 Hz, 3H); $^{13}$C NMR (100 MHz, $CDCl_3$) δ 173.0, 136.3, 129.1, 127.9, 127.6, 62.2, 41.2, 35.2, 13.9; 3290, 2984, 1717, 1306, 1195; HRMS (CI) m/z calcd for $(C_{11}H_{13}NO_2+H^+)$: 192.1024, found: 192.1018.

Example 7

Synthesis of Azide 6j

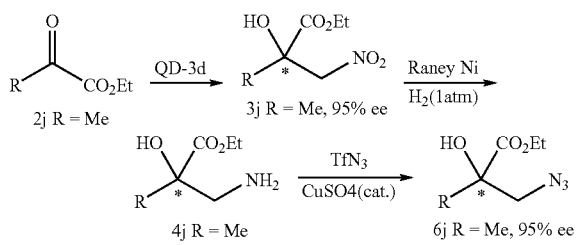

See Christensen, C.; Juhl, K.; Jørgensen, K. A.; *Chem. Commun.* 2001, 2222-2223; Christensen, C.; Juhl, K.; Hazell, R. G.; Jørgensen, K. A. *J. Org. Chem.* 2002, 67, 4875-4881; Liu, Q.; Tor, Y. *Org. Lett.* 2003, 5, 2571-2572; and Nyffeler, P. T.; Liang, C.-H.; Koeller, K. M.; Wong, C.-H *J. Am. Chem. Soc.* 2002, 124, 10773-10778.

At −20° C., to a solution of α-keto ester 2j (580 mg, 5 mmol), nitromethane (2.7 mL) in $CH_2Cl_2$ (5 mL) was added catalyst QD-1d (104 mg, 5 mol %). The resulting mixture was kept at −20° C. for 13 hours and TLC showed 2j is completely consumed. The reaction mixture was directly subjected to silica gel flash chromatography (EA/Hexanes=1/15) to give 3j as a clear oil (830 mg, 94% yield). The ee of 3j was determined to be 95%. The column was washed with MeOH and the catalyst was recovered almost quantitatively (>103 mg). The recovered catalyst was shown to be identical to that before the reaction by NMR analysis.

To a solution of 3j (800 mg, obtained with QD-1d in 95% ee) in EtOH (20 mL) was added Raney nickel (1.5 g in 10 mL). The reaction mixture was stirred under $H_2$ at atmospheric pressure for 4 h at room temperature. After the starting material was completely consumed (monitored by TLC), the reaction mixture was passed through a short pad of celite and celite was washed with EtOH (2×10 mL). The filtrate was concentrated in vacuo and the residue 4j was used directly in next step (600 mg, 90% crude yield).

A solution of $NaN_3$ (3.5 g, 54 mmol) in water (8 mL) and $CH_2Cl_2$ (3 mL) was cooled to 0° C. in an ice-water bath. To this solution under vigorous stirring, $Tf_2O$ (1.51 mL, 9 mmol) was added dropwise via a syringe. The reaction mixture was stirred at 0° C. for 3 h, afterwhich the mixture was diluted with water (2 mL). The aqueous and organic phases were separated. The organic phase was collected and the aquous phase was extracted with $CH_2Cl_2$ (3 mL). The combined organic phase was washed with sat. $NaHCO_3$ aq. (10 mL). This solution was used for the next step.

At room temperature, to a solution of 4j (475 mg, crude from 3j as described before) in $CH_2Cl_2$ (3 mL) was added $Et_3N$ (1.25 mL) and a solution of $CuSO_4$ (24 mg in 0.5 mL $H_2O$) consecutively. To the resulting mixture, a freshly prepared solution of $TfN_3$ in $CH_2Cl_2$ as described above was added. This is followed by the addition of MeOH (around 2.0 mL) afterwhich the solution became homogenous. The resulting mixture was stirred at room temperature for 2.5 hours. The reaction mixture was poured into sat. $NaHCO_3$ aq. (30 mL). The resulting mixture was extracted with $CH_2Cl_2$ (2×50 mL). The combined organic phase was washed with brine and dried over anhydrous $Na_2SO_4$. The solvent was removed in vacuo and the residue was purified by chromatography (silica gel, petroleum ether/ether=9/1) to give 6j as a clear oil (390 mg, 70% yield, 59% yield over 3 steps from 2j). The ee of 6j was determined to be 95% by HPLC analysis: Daicel chiralpak AS, Hexane:IPA, 97:3, 1.0 mL/min, λ 215 nm t(major)=8.40 min, t(minor)=9.52 min); $[\alpha]_D^{25}$=−83.3° (c: 1.0 in $CHCl_3$); $^1$H NMR (400 MHz, $CDCl_3$) δ 4.31-4.25 (m, 2H), 3.51 (s, 1H), 3.47-3.40 (m, 2H), 1.41 (s, 3H), 1.32 (t, J=6.8 Hz, 3H); $^{13}$C NMR (100 MHz, $CDCl_3$) δ 174.7, 75.1, 62.5, 58.4, 23.3, 14.0; IR ($CHCl_3$) ν 3503, 2985, 2939, 2105, 1733, 1456, 1258. (Caution: the product is very volatile, care needed when removing solvent in vacuo.)

Example 8

Synthesis of Aziridine 7l

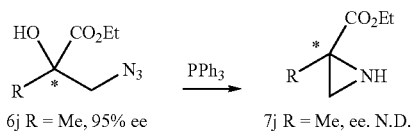

See Shao, H.; Zhu, Q.; Goodman, M. *J. Org. Chem.* 1995, 60, 790-791.

To a solution of 6j (188 mg, 1.09 mmol) in anhydrous $CH_3CN$ (4 mL) was added $PPh_3$ (427 mg, 1.6 mmol) at room temperature. The mixture was stirred at r.t. for 1 h and then refluxed for 9 h under Ar atmosphere. The solvent was removed in vacuo and the residue was purified by chromatography (silica gel, petroleum ether/ether=5/1) to give 7j as a clear oil (99 mg, 71% yield). $[\alpha]_D^{25}$=−28 (c: 0.5 in $CHCl_3$); $^1$H NMR (400 MHz, $CDCl_3$) δ 4.20 (dq, J=1.6 Hz, 7.2 Hz, 2H), 2.17 (d, J=10.4 Hz, 1H), 1.64 (d, J=4.8 Hz, 1H), 1.42 (s, 3H), 1.29 (t, J=7.2 Hz, 3H); $^{13}$C NMR (100 MHz, $CDCl_3$) δ 174.2, 53.4, 34.7, 34.1, 17.9, 14.0; IR ($CHCl_3$) ν 3294, 3070, 2983, 2940, 1724, 1325, 1199; HRMS (CI) m/z calcd for ($C_6H_{11}NO_2+H^+$): 130.0868, found: 130.0867. (Caution: the product is very volatile, care needed when removing solvent in vacuo.)

Example 9

Synthesis of α-Methylcysteine 81

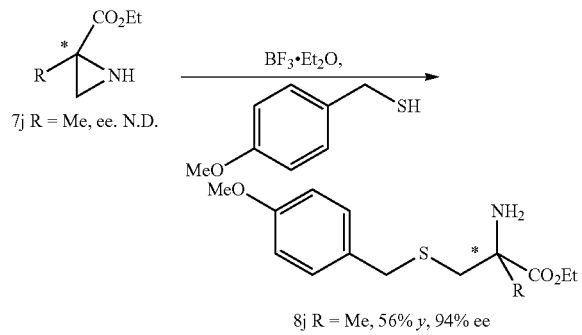

7j R = Me, ee. N.D.

8j R = Me, 56% y, 94% ee

See Shao, H.; Zhu, Q.; Goodman, M. *J. Org. Chem.* 1995, 60, 790-791.

At 0° C., to the solution of 7j (65 mg, 0.5 mmol) in $CH_2Cl_2$ (1.5 mL) was added p-methoxybenzyl mercaptan (0.21 mL, 1.5 mmol) and boron trifluoride diethyl etherate (0.11 mL). The resulting mixture was stirred at 0° C. for 12 h followed by stirring at room temperature for 24 h. The reaction mixture was poured into sat. $NaHCO_3$ aq. (20 mL) and the mixture was extracted with ethyl acetate (2×30 mL). The combined organic phase was washed with brine, dried over anhydrous $Na_2SO_4$. The solvent was removed and the residue was purified by chromatography (silica gel, petroleum ether/ethyl acetate=2/1) to give 8j as a clear oil (80 mg, 56% yield) in 94% ee (determined by HPLC: Daicel chiralcel OD, Hexane: IPA, 80:20, 0.5 mL/min, λ 254 nm, t (minor)=14.56 min, t (major)=15.22 min). $[\alpha]_D^{25}$=12° (c: 1.05 in $CHCl_3$); $^1H$ NMR (400 MHz, $CDCl_3$) δ 7.23 (d, J=8.4 Hz, 2H), 6.84 (d, J=8.4 Hz, 2H), 4.20-4.14 (m, 2H), 3.79 (s, 3H), 3.70 (s, 2H), 2.92 (d, J=13.2 Hz, 1H), 2.59 (d, J=13.2 Hz, 1H), 1.85 (br, 2H), 1.34 (s, 3H), 1.28 (t, J=7.2 Hz, 3H); $^{13}C$ NMR (100 MHz, $CDCl_3$) δ176.3, 158.6, 130.1, 129.9, 113.8, 61.2, 58.6, 55.2, 42.0, 37.1, 26.3, 14.1; IR ($CHCl_3$) ν 3373, 2978, 2933, 1731, 1610, 1512, 1249; HRMS (ESI) m/z calcd for ($C_{14}H_{21}NO_3S+H^+$): 284.1320, found: 284.1315.

INCORPORATION BY REFERENCE

U.S. patent application Ser. No. 11/140,574, filed May 27, 2005 is hereby incorporated by reference in its entirety. Moreover, all of the other U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound represented by formula I:

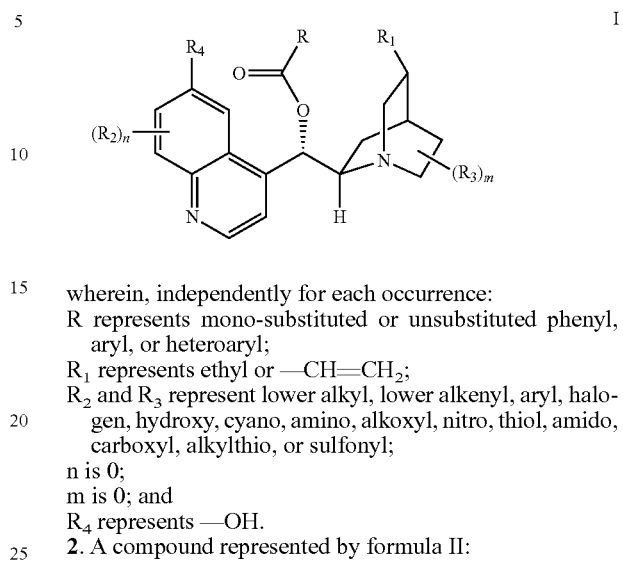

wherein, independently for each occurrence:
R represents mono-substituted or unsubstituted phenyl, aryl, or heteroaryl;
$R_1$ represents ethyl or —CH=$CH_2$;
$R_2$ and $R_3$ represent lower alkyl, lower alkenyl, aryl, halogen, hydroxy, cyano, amino, alkoxyl, nitro, thiol, amido, carboxyl, alkylthio, or sulfonyl;
n is 0;
m is 0; and
$R_4$ represents —OH.

2. A compound represented by formula II:

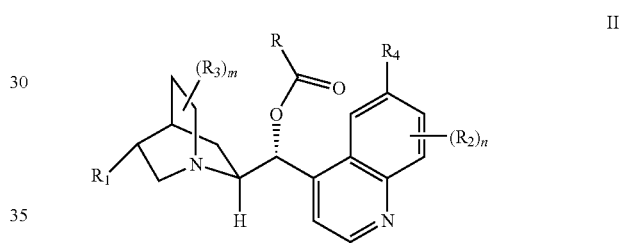

wherein, independently for each occurrence:
R represents mono-substituted or unsubstituted phenyl, aryl, or heteroaryl;
$R_1$ represents ethyl or —CH=$CH_2$;
$R_2$ and $R_3$ represent lower alkyl, lower alkenyl, aryl, halogen, hydroxy, cyano, amino, alkoxyl, nitro, thiol, amido, carboxyl, alkylthio, or sulfonyl;
n is 0;
m is 0; and
$R_4$ represents —OH.

3. The compound of claim 1 or 2, wherein R represents aryl or heteroaryl.

4. The compound of claim 1 or 2, wherein R represents aryl.

5. The compound of claim 1 or 2, wherein R represents mono-substituted or unsubstituted phenyl.

6. The compound of claim 1 or 2, wherein R represents mono-substituted phenyl.

7. The compound of claim 1 or 2, wherein R represents unsubstituted phenyl.

8. The compound of claim 1 or 2, wherein $R_1$ is ethyl.

9. The compound of claim 1 or 2, wherein $R_1$ is —CH=$CH_2$.

10. The compound of claim 1 or 2, wherein R is aryl and $R_1$ is ethyl.

11. The compound of claim 1 or 2, wherein R is mono-substituted or unsubstituted phenyl and $R_1$ is ethyl.

12. The compound of claim 1 or 2, wherein R is unsubstituted phenyl; and $R_1$ is ethyl.

13. The compound of claim 1 or 2, wherein R is aryl and $R_1$ is —CH=$CH_2$.

14. The compound of claim 1 or 2, wherein R is mono-substituted or unsubstituted phenyl and $R_1$ is —CH=CH$_2$.
15. The compound of claim 1 or 2, wherein R is unsubstituted phenyl; and $R_1$ is —CH=CH$_2$.
16. A compound, selected from the group consisting of:
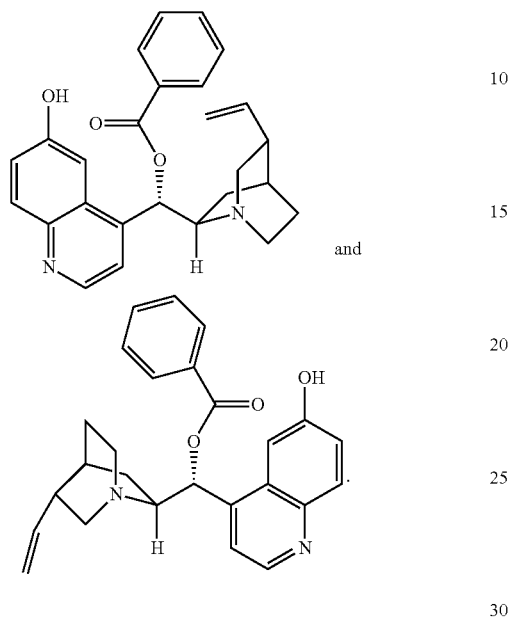
* * * * *